US010376593B2

(12) United States Patent
Mulard et al.

(10) Patent No.: US 10,376,593 B2
(45) Date of Patent: Aug. 13, 2019

(54) GLYCOCONJUGATES AND THEIR USE AS POTENTIAL VACCINES AGAINST INFECTION BY *SHIGELLA FLEXNERI*

(71) Applicants: INSTITUT PASTEUR, Paris (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR); UNIVERSITE PARIS DESCARTES, Paris (FR)

(72) Inventors: Laurence Mulard, Le Kremlin Bicetre (FR); Pierre Chassagne, Beaumont (FR); Philippe Sansonetti, Paris (FR); Armelle Phalipon, Paris (FR); Francois Traincard, Issy-les-moulineaux (FR); Farida Nato, Antony (FR)

(*) Notice: Subject to any disclaimer, the term of this patent is extended or adjusted under 35 U.S.C. 154(b) by 0 days.

(21) Appl. No.: 14/438,750

(22) PCT Filed: Oct. 29, 2013

(86) PCT No.: PCT/EP2013/072651
§ 371 (c)(1),
(2) Date: Apr. 27, 2015

(87) PCT Pub. No.: WO2014/067970
PCT Pub. Date: May 8, 2014

(65) Prior Publication Data
US 2015/0290331 A1 Oct. 15, 2015

(30) Foreign Application Priority Data
Oct. 29, 2012 (EP) ..................... 12306351

(51) Int. Cl.
*A61K 47/64* (2017.01)
*A61K 9/127* (2006.01)
*A61K 38/16* (2006.01)
*C07K 17/10* (2006.01)
*A61K 47/54* (2017.01)

(52) U.S. Cl.
CPC .......... *A61K 47/646* (2017.08); *A61K 9/1271* (2013.01); *A61K 38/164* (2013.01); *A61K 47/549* (2017.08); *C07K 17/10* (2013.01); *C07K 2317/76* (2013.01); *Y02A 50/475* (2018.01)

(58) Field of Classification Search
None
See application file for complete search history.

(56) References Cited

U.S. PATENT DOCUMENTS

2008/0112951 A1* 5/2008 Phalipon ............ A61K 39/0283
424/133.1
2010/0239584 A1* 9/2010 Mulard .............. A61K 47/4833
424/137.1

FOREIGN PATENT DOCUMENTS

| EP | 2369345 A1 | 9/2011 |
| WO | 2008155487 A2 | 12/2008 |
| WO | 2009104074 A2 | 8/2009 |
| WO | 2011062615 A1 | 5/2011 |

OTHER PUBLICATIONS

Dmitriev, B. A., Knirel, Y. A., Sheremet, O. K., Shashkov, A. A., Kochetkov, N. K., & Hofman, I. L. (1979). Somatic antigens of Shigella. European Journal of Biochemistry, 98(1), 309-316.*
IUPAC. Compendium of Chemical Terminology, 2nd ed. (the "Gold Book"). Compiled by A. D. McNaught and A. Wilkinson. Blackwell Scientific Publications, Oxford (1997).*
Pinto, B. M., Reimer, K. B., Morissette, D. G., & Bundle, D. R. (1989). Oligosaccharides corresponding to biological repeating units of Shigella flexneri variant Y polysaccharide. 2. Synthesis and two-dimensional NMR analysis of a hexasaccharide hapten. The Journal of Organic Chemistry, 54(11), 2650-2656.*
Greene'S Protective Groups in Organic Synthesis, Fourth Edition, Wuts and Green Eds., 2007 by John Wiley & Sons, Inc.*
Rochepeau-Jobron, L., & Jacquinet, J. C. (1997). Diastereoselective hydroboration of substituted exo-glucals revisited. A convenient route for the preparation of L-iduronic acid derivatives. Carbohydrate research, 303(4), 395-406.*
Perepelov, A. V., Shekht, M. E., Liu, B., Shevelev, S. D., Ledov, V. A., Senchenkova, S. Y. N., ... & Wang, L. (2012). Shigella flexneri O-antigens revisited: final elucidation of the O-acetylation profiles . . . FEMS Immunology & Medical Microbiology, 66(2), 201-210. (Year: 2012).*
Carlin, N. I. A., et al., Infection and Immunity, vol. 55, No. 6, pp. 1412-1420 (1987).
Chassagne, P., et al., Eur. J. Org. Chem., pp. 4085-4106 (2013).
Kubler-Kielb, J., et al., Carbohydrate Research, vol. 345, pp. 1600-1608 (2010).
Pozsgay, V., J. Org. Chem., vol. 63, pp. 5983-5999 (1998).
Pozsgay, V., et al., Synlett, No. 6, pp. 743-767 (2003).
Wright, K., et al., Organic & Biomolecular Chemistry, vol. 2, No. 10, pp. 1518-1527 (2004).

* cited by examiner

*Primary Examiner* — Shaojia A Jiang
*Assistant Examiner* — Dale R Miller
(74) *Attorney, Agent, or Firm* — Arrigo, Lee, Gutman & Mouta-Bellum, LLP

(57) ABSTRACT

The present invention relates to a conjugate comprising an oligo- or polysaccharide selected from the group consisting of: $(X)_x$-$\{BCDA\}_n$-$(Y)_y$, $(X)_x$-$\{CDAB\}_n$-$(Y)_y$, $(X)_x$-$\{DABC\}_n$-$(Y)_y$, $(X)_x$-$\{ABCD\}n$-$(Y)_y$, wherein A, B, C, D, X and Y, x, y and n are as defined in claim 1, said oligo- or polysaccharide being bound to a carrier.

18 Claims, No Drawings

GLYCOCONJUGATES AND THEIR USE AS POTENTIAL VACCINES AGAINST INFECTION BY *SHIGELLA FLEXNERI*

This invention relates to compositions and methods for eliciting an immunogenic response in mammals, including responses that provide protection against, or reduce the severity of bacterial infections. More particularly it relates to the use of oligo- or polysaccharides obtained through synthesis, and conjugates thereof to induce serum antibodies having protective activity against *Shigella flexneri*, in particular *S. flexneri* serotype 6 (SF6) or serotype 6a (SF6a). These saccharides and/or conjugates thereof are useful as vaccines to induce serum antibodies which have protective activity against *S. flexneri*, in particular SF6, or SF6a and are useful to prevent and/or treat shigellosis caused by *S. flexneri*. More generally these antibodies are useful for preventing or treating infections by bacteria from the *Escherichia* or *Shigella* genus, particularly infections by *S. flexneri* and *Escherichia coli*, in particular SF6, SF6a, or *E. coli* O147.[1]

The present invention also relates to diagnostic tests for shigellosis using one or more of the oligo- or polysaccharides, or conjugates described above.

Shigellosis, an invasive infection of the human colon, is identified as one of the major diarrhoeal diseases worldwide:[2] In its most classical expression, it is characterized by a triad of fever, intestinal cramps and bloody diarrhea.[3] Also known as bacillary dysentery, this highly contagious infection is associated with increased antibiotic-resistance.[4] In its endemic form, it remains a major health concern especially in the pediatric population living in the most impoverished areas.[4-5] *S. flexneri*—one out of the four species of *Shigella*—prevails in developing countries, where it accounts for endemic disease.[4-6] Numerous *S. flexneri* serotypes—varying in geographical and temporal distributions—are isolated from patients. In recent years, SF6 was identified as a serotype of increasing prevalence in several settings worldwide,[4, 7] and evidences strongly support the inclusion of SF6 as one of the key valences to be included in a broad-coverage *Shigella* vaccine.[5, 8]

*S. flexneri* serotypes are defined on the basis of the carbohydrate repeating unit of the surface O-antigen (O—Ag), that is the polysaccharide part of the bacterial lipopolysaccharide (LPS).[9] Protection against reinfection by the homologous serotype, suggesting serotype-specific natural immunity, was established following *Shigella* and *E. coli* O147 infection.[7a] [10] These observations provided strong evidence for *S. flexneri* O—Ags being major targets of the host adaptive immunity. Accordingly, several vaccine candidates, derived from LPS[7b] or fragments thereof, have been developed against shigellosis and some of them have been evaluated during clinical trials.[5,12]

The inventors have now focused on the development of well-defined neoglycoconjugates targeting infections caused by SF6. The target neoglycoconjugates were notably constructed by covalently linking an immunocarrier, serving as T-helper epitope(s), to appropriate carbohydrate (oligo- or polysaccharide) haptens, bringing in B epitopes mimicking the SF6 O—Ag. Neoglycoconjugates according to the invention are useful for obtaining an immune response directed against SF6 and can as such be included in a *Shigella* vaccine composition.

Conjugates

In a first object, the present invention provides a conjugate comprising an oligo- or polysaccharide selected from the group consisting of:

$(X)_x\text{-}\{BCDA\}_n\text{-}(Y)_y$ $(X)_x\text{-}\{CDAB\}_n\text{-}(Y)_y$ $(X)_x\text{-}\{DABC\}_n\text{-}(Y)_y$ $(X)_x\text{-}\{ABCD\}_n\text{-}(Y)_y$ wherein:

A is a beta-D-Galacturonic acid (1,3) residue,

B is a N-acetyl-beta-D-Galactosamine (1,2) residue,

C is independently, at each occurrence, an alpha-L-Rhamnose (1,2) residue, wherein at most one of its $3_C$ or $4_C$ positions is OAc (i.e O—C(=O)CH$_3$), provided that when C is a non reducing end residue, its $2_C$ position may be acetylated or not.

D is an alpha-L-Rhamnose (1,4) residue, x and y are independently selected among 0 and 1, X and Y are independently selected among A, B, C, D, AB, BC, CD, DA, ABC, BCD, CDA, DAB, and wherein n is an integer comprised between 0 and 10, provided that x, y and n are not null simultaneously, Said oligo- or polysaccharide being bound to a carrier, in particular covalently bound to a carrier.

Methods for linking oligo- and/or polysaccharides to a non-toxic non-host protein are well known in the art. The oligo- or polysaccharide can be covalently bound to a carrier with or without a linking molecule or spacer. The linking molecule or spacer does not contain any carbohydrate residue; thus, it is neither a carbohydrate residue nor an oligosaccharide- or a polysaccharide compound. The oligo- or polysaccharide is preferably conjugated to a carrier using a linking molecule. A linker or crosslinking agent, as used in the present invention, is preferably a small molecule, linear or not, having a molecular weight of approximately <500 daltons and is non-pyrogenic and non-toxic in the final product form.

Advantageously, in addition to ensuring product homogeneity and avoiding microbial contamination, the use of synthetic oligo- or polysaccharides is fully compatible with their site selective attachment onto the carrier, thus opening the way to a reproducible conjugation process. On the one hand, the uncontrolled masking of epitopes important for protection is avoided, and on the other hand it becomes possible to eliminate side effects generated from neoepitopes formed during conjugation.

To conjugate with a linker or crosslinking agent, either or both of the oligo- or polysaccharide and the carrier may be covalently bound to a linker first. The linkers or crosslinking agents are homobifunctional or heterobifunctional molecules,[14] adipic dihydrazide, ethylenediamine, cystamine, N-succinimidyl 3-(2-pyridyldithio)propionate (SPDP), N-succinimidyl-[N-(2-iodoacetyl)-β-alanyl]propionate-propionate (SIAP), 3,3'-dithiodipropionic acid, and the like. According to the type of linkage between the oligo- or polysaccharide and the carrier, there is the possibility of preparing a conjugate wherein the ratio of the oligo- or polysaccharide versus the carrier can vary between 1:1 and 30:1. Preferably, this ratio is comprised between 5:1 and 20:1.

A carrier can be a natural, modified-natural, synthetic, semi-synthetic or recombinant material containing one or more functional groups, for example primary and/or secondary amino groups, azido groups, thiol, or carboxyl group. The carrier can be water soluble or insoluble. Carriers that fulfil these criteria are well-known to those of ordinary skill in the art.

Suitable carriers according to the present invention notably include proteins, peptides, lipopeptides, zwitterionic polysaccharides, lipid aggregates (such as oil droplets or liposomes), and inactivated virus particles.

Immunocarriers are carriers chosen to increase the immunogenicity of the oligo- or polysaccharide and/or to raise antibodies against the carrier which are medically beneficial.

Suitable immunocarriers according to the present invention notably include proteins, peptides, lipopeptides, lipid aggregates containing T-helper peptides (at least one), and inactivated virus particles.

According to an advantageous embodiment, the glycoconjugate of the invention is covalently bound to a protein or a peptide comprising at least one T-helper epitope, for use as a vaccine against *S. flexneri* infection.

Protein carriers known to have potent T-helper epitopes, include but are not limited to bacterial toxoids such as tetanus, diphtheria and cholera toxoids, *Staphylococcus* exotoxin or toxoid, *Pseudomonas aeruginosa* Exotoxin A and recombinantly produced, genetically detoxified variants thereof, outer membrane proteins (OMPs) of *Neisseria meningitidis* and *Shigella* proteins. The recombinantly-produced, non-toxic mutant strains of *P. aeruginosa* Exotoxin A (rEPA) are described and used in polysaccharide-protein conjugate vaccines.[15] The CMR197 carrier is a well characterized non-toxic diphtheria toxin mutant that is useful in glycoconjugate vaccine preparations intended for human use.[16] Other exemplary protein carriers include the Fragment C of tetanus toxin.[17] Also CRM9 carrier has been disclosed for hum an immunisation.[18]

Synthetic peptides bearing immunodominant T-helper cell epitopes can also act as carriers in polysaccharide and oligosaccharide conjugates. The peptide carriers include polypeptides containing multiple T-helper epitopes addressing the extensive polymorphism of HLA molecules,[19] and universal T-helper epitopes compatible with human use. Exemplary T-helper epitopes, include but are not limited to natural epitopes characterized from tetanus toxoid,[20] and non-natural epitopes or engineered epitopes such as the pan HLA DR-binding epitope PADRE.[21]

In a particular embodiment of the present invention, the immunocarrier is selected among a protein or a peptide comprising at least one T-helper epitope, or a derivative thereof. In a particular aspect, the immunocarrier is the peptide PADRE. In another aspect, the immunocarrier is tetanus toxoid (TT) or a fragment thereof.

Other types of carrier include but are not limited to biotin or liposomes. The oligo- or polysaccharides conjugated to biotin or to a label are especially designed for diagnosing *S. flexneri* infections. As regards the use of a liposome as a carrier, in particular those which do not imply covalent links, reference could be made to the International Application WO 2010/136947.

In a particular embodiment, the conjugate comprises an oligo- or polysaccharide liable to be bound by an anti-*Shigella flexneri* serotype 6 and/or 6a antibody, also called anti-SF6 and/or anti-SF6a antibody, in particular a specific anti-*Shigella flexneri* serotype 6 and/or 6a antibody. Preferably, the anti-*Shigella flexneri* serotype 6 and/or 6a antibody binds, in particular specifically, to the LPS of *Shigella flexneri* serotype 6 and/or 6a.

In a particular embodiment, the half maximal inhibitory concentration, i.e. the $IC_{50}$ value, of said oligo- or polysaccharide with respect to the binding of the anti-*Shigella flexneri* serotype 6 and/or 6a antibody to its target, in particular the LPS of *Shigella flexneri* serotype 6 and/or 6a, is inferior or equal to 500 µM, preferably inferior or equal to 250 µM, more preferably inferior or equal to 100 µM, most preferably inferior or equal to 10 µM.

As used herein, the $IC_{50}$ value is defined as the concentration of oligosaccharide or polysaccharide of the invention required to inhibit 50% of an anti-SF6 and/or anti-SF6a antibody binding to its target, in particular to the LPS from *Shigella flexneri* serotype 6 (SF6) or 6a (SF6a). It can be determined by any conventional method, such as that disclosed in the reference Phalipon A. et al (J. Immunol. 176 1686 (2006) or in the following example section. In particular, the $IC_{50}$ value can be determined by performing a enzyme-linked immunosorbent assay (ELISA).

In a particular embodiment, the antibody is an antibody, in particular a monoclonal antibody, which has been obtained by immunizing an animal, in particular a mouse, by the *Shigella flexneri* SF6 Sc544 strain.

In another particular embodiment, the antibody is a monoclonal antibody secreted by the hybridoma deposited at the Collection Nationale de Culture de Microorganismes (CNCM, Paris, France) according to the Budapest Treaty under number I-4813, on Oct. 28, 2013. In this regard, the present invention also relates to the monoclonal antibody secreted by the hybridoma deposited at the Collection Nationale de Culture de Microorganismes (CNCM, Paris, France) according to the Budapest Treaty under number I-4813, on Oct. 28, 2013.

Anti SF6 and/or SF6a antibodies can be obtained according to conventional methods, such as that disclosed by Carlin NI and Lindbergh AA in *Monoclonal antibodies specific for Shigella flexneri lipopolysaccharides: clones binding to type IV, V, and VI antigens, group* 3,4 *antigen, and an epitope common to all Shigella flexneri and Shigella dysenteriae type* 1 *stains*. Infect Immun. 1987 June; 55(6): 1412-20, or in the following example section. In particular, anti SF6 and/or SF6a antibodies can be obtained by immunizing mice with heat-killed bacteria *Shigella flexneri* serotype 6 (SF6) Sc544 strain, producing hybridoma from spleen cells of immunized mice, and selecting hybridomas which secrete antibodies binding to purified LPS from *Shigella flexneri* serotype 6 (SF6) Sc544 strain.

In a particular embodiment, there are included conjugates as defined herein, wherein X and Y are independently selected among AB, BC, CD, DA, ABC, BCD, CDA, DAB.

In a particular embodiment, there are included conjugates as defined herein wherein x is 0 or y is 0, notably wherein both x and y are 0.

In another particular embodiment, n is an integer comprised between 1 and 10.

In a particular embodiment, there are included conjugates as defined herein, wherein the oligo- or polysaccharide is selected from the group consisting of:

$\{BCDA\}_n$ $\{CDAB\}_n$ $\{DABC\}_n$ $\{ABCD\}_n$

A, B, C, D and n is an integer comprised between 1 and 10.

In a preferred aspect, there are included conjugates as defined herein wherein n is comprised between 1 and 6.

In certain aspects, there are included conjugates as defined herein wherein the ratio of $3_C$-OAc/$4_C$-OAc is superior to 1, provided that when C is a non reducing end residue, its $2_C$ position may be acetylated or not.

As used herein, the term 3$_C$-OAc (respectively 4$_C$-OAc) refers to the number of repeating units, per chain, containing an OH group located at position 3 (respectively at position 4) of the alpha-L-Rhamnose residue (C residue) which is acetylated.

In a particular aspect, the oligo- or polysaccharide is {CDAB}$_n$, wherein A, B, C, D and n are as defined above. These oligo- or polysaccharides are advantageously obtained by chemical synthesis.

Immunogenic Compositions

In a second object, the invention provides an immunogenic composition comprising a conjugate according to the invention and a physiologically acceptable vehicle.

The vaccine composition includes one or more pharmaceutically acceptable excipients or vehicles such as water, saline, glycerol, ethanol. Additionally, auxiliary substances, such as wetting or emulsifying agents, pH buffering substances, and the like, may be present in such vehicles.

The glycoconjugates of the present invention which induce protective antibodies against *S. flexneri* infection, in particular SF6 and SF6a, are administered to a mammal subject, preferably a human, in an amount sufficient to prevent or attenuate the severity, extent of duration of the infection by *S. flexneri*, in particular SF6 and SF6a.

Each vaccine dose comprises a therapeutically effective amount of oligo- or polysaccharide conjugate. Such amount will vary depending on the capacity of the subject to synthesize antibodies against the oligo- or polysaccharide, the degree of protection desired, the particular oligo- or polysaccharide conjugate selected and its mode of administration, among other factors. An appropriate effective amount can be readily determined by one of skill in the art. A therapeutically effective amount may vary in a wide range that can be determined through routine trials.

More particularly the oligo- or polysaccharide conjugate of the invention will be administered in a therapeutically effective amount that comprises from 1 mg to 100 µg, notably from 1 µg to 50 µg of oligo- or polysaccharide, preferably 1 µg to 10 µg. An optimal amount for a particular vaccine can be ascertained by standard studies involving measuring the anti-SF6 and/or SF6a LPS antibody titers in subjects, more accurately protective antibody titers.

Following an initial administration, subjects may receive one or two booster injections at about four week intervals. For infants less than 12 months of age, two doses at not less than two month intervals can be administered, the first dose not being administered before 2 months of age.

The immunogenic composition of the invention may be administered with or without adjuvant. Adjuvants generally combined with glycoconjugate vaccines allow to strengthen the antibody response and hence the B response. Adjuvants can be added directly to the vaccine compositions or can be administered separately, either concurrently with or shortly after, administration of the vaccine. Such adjuvants include but are not limited to aluminium salts (aluminium hydroxide), oil-in-water emulsion formulations with or without specific stimulating agents such as muramyl peptides, saponin adjuvants, cytokines, detoxified mutants of bacterial toxins such as the cholera toxin, the pertussis toxin, or the *E. coli* heatlabile toxin.

The immunogenic composition of the invention may be administered with other immunogens or immunoregulatory agents, for example, immunoglobulins, cytokines, lymphokines and chemokines.

In a particular aspect, the immunogenic composition further comprises an immunogen which affords protection against another pathogen, such as for example, *S. flexneri* serotype 1b, 2a and 3a, members of other *Shigella* species such as *S. sonnei* and *S. dysenteriae* type 1, or pathogens responsible for diarrhoeal disease in humans.

Typically, the vaccine compositions are prepared as injectables either as liquid solutions or suspensions; or as solid forms suitable for solution or suspension in a liquid vehicle prior to injection. The preparation may be emulsified or encapsulated in liposomes for enhanced adjuvant effect. In this respect, reference could be made to International Application WO 2010/136947.

Once formulated, the vaccine compositions may be administered parenterally, by injection, either subcutaneous, intramuscular or intradeiuial.

Alternative formulations suitable for other mode of administration include oral and intranasal formulations.

Oligo- or Polysaccharides (Ia)

In an additional aspect, the invention provides oligo- or polysaccharide (Ia) selected from the group consisting of:

$(X)_x\text{-}\{BCDA\}_n\text{-}(Y)_y\text{-}OQ$ $(X)_x\text{-}\{CDAB\}_n\text{-}(Y)_y\text{-}OQ$ $(X)_x\text{-}\{DABC\}_n\text{-}(Y)_y\text{-}OQ$ $(X)_x\text{-}\{ABCD\}_n\text{-}(Y)_y\text{-}OQ$ Wherein:

A, B, C, D, X, Y, x, y and n are as defined above,

O is the $C_1$ oxygen atom of the reducing end residue of the oligo- or polysaccharide, Q is H, or a group LZ, L is a divalent $C_1$-$C_{12}$ alkyl or alkenyl chain optionally interrupted by one or more heteroatoms, notably selected from an oxygen atom, a sulphur atom or a nitrogen atom, said nitrogen and sulphur atoms being optionally oxidized, and the nitrogen atom being optionally involved in a divalent acetamide bond (—NHC(=O)—), and Z is a terminal reactive function, optionally protected, able to form a covalent bond with a carrier and/or a solid support.

Preferably, the oligo- or polysaccharide (Ia) is not {CDAB} —OH.

In a preferred aspect, Z is Hal, biotin, $C_2$-$C_6$ alkenyl, $C_2$-$C_6$ alkynyl, azido, alkoxy, epoxyde, acetal, C(=O)H, $SR_1$, $NH_2$ or NHC(=O)$CH_2$Hal, $R_1$ being H, C(=O)$CH_3$ or $SR_2$, and $R_2$ being a $C_1$-$C_6$ alkyl, a $C_6$-$C_{10}$ aryl, or a 5 to 7 membered heteroaryl, such as pyridyl, or any group allowing to convert $SSR_2$ into SH.

In another aspect, the oligo- or polysaccharide defined above is immobilized on a solid support.

Kits for the Diagnostic of SF6 Infection

In a further object, the invention provides a kit for the in vitro diagnostic of SF6 infection, wherein said kit comprises an oligo- or polysaccharide (Ia) as defined herein, optionally bound to a label or a solid support.

In a particular embodiment, the oligo- or polysaccharide (Ia) according to the present invention are used, in vitro, as SF6 specific diagnostic reagents in standard immunoassays.

Alternatively, the oligo- or polysaccharides (Ia) according to the present invention are used to test the presence of SF6-specific antibodies. Oligo- or polysaccharides may be used for epidemiological studies, for example for determining the geographic distribution and/or the evolution of SF6 infection worldwide, as well as for evaluating the SF6-specific antibody response induced by an immunogen.

The oligo- or polysaccharides (Ia) according to the present invention may be advantageously labelled and/or immobilized onto a solid phase, according to standard protocols known to the man skilled in the art. Such labels include, but are not limited to, enzymes (alkaline phosphatase, peroxydase), luminescent or fluorescent molecules. For example an oligo- or polysaccharide conjugated to biotine, according to the present invention may be immobilized onto a solid phase, to detect the presence of SF6-specific antibodies in biological samples.

Such immunoassays include, but are not limited to, agglutination assays, radioimmunoassay, enzyme-linked immunosorbent assays, fluorescence assays, western-blots and the like.

Such assays may be for example, of direct format (where the labelled oligo- or polysaccharide (Ia) is reactive with the antibody to be detected), an indirect format (where a labelled secondary antibody is reactive with said oligo- or polysaccharide (Ia)), or a competitive format (addition of a labelled oligo- or polysaccharide (Ia)).

For all therapeutic, prophylactic and diagnostic uses, the oligo- or polysaccharides (Ia) of the invention, alone or linked to a carrier, as well as antibodies and other necessary reagents and appropriate devices and accessories may be provided in kit form so as to be readily available and easily used.

Oligo- or Polysaccharide (Ib)

In a further object, the invention provides oligo- or polysaccharide (Ib) selected from the group consisting of:

$(X)_x$-$\{BCDA\}_n$-$(Y)_y$-W $(X)_x$-$\{CDAB\}_n$-$(Y)_y$-W $(X)_x$-$\{DABC\}_n$-$(Y)_y$-W $(X)_x$-$\{ABCD\}_n$-$(Y)_y$-W

Wherein:

A is a beta-D-Galacturonic (1,3) acid residue,

B is a N-protected-beta-D-Galactosamine (1,2) residue, wherein said N-protecting group is an acetyl group, or a precursor thereof such as a N-trichloroacetyl group, C is an alpha-L-Rhamnose (1,2) residue, wherein at most one of $3_C$ or $4_C$ is OAc, D is an alpha-L-Rhamnose (1,4) residue, x and y are independently selected among 0 and 1, n is an integer comprised between 0 and 10, provided that x, y and n are not null simultaneously, X and Y are independently selected among A, B, C, D, AB, BC, CD, DA, ABC, BCD, CDA, DAB, wherein each OH and/or $CO_2H$ group of said residues are optionally protected by a protecting group, W is $OR^i$, $SR^{ii}$ or Hal, wherein said O, S and Hal are the $C_1$ heteroatom of the reducing end residue of the oligo- or polysaccharide chain, S being optionally oxidized, $R^i$ is H, a hydroxyl protecting group, an anomeric hydroxyl activating group, or a LZ group, L and Z being as defined above for formula (h), $R^{ii}$ is $C_1$-$C_{12}$ alkyl, $C_6$-$C_{10}$ aryl, an imidate leading preferably to S-thiazolinyl (STaz) or S-benzoxazolyl (SBox),[22]

and wherein n is an integer comprised between 0 and 10 provided that x, y and z are not null simultaneously.

As used herein, the wording "acetyl precursor group" refers to a chemical group that can be converted into a $CH_3$—CO— radical, notably by reduction. Examples of such acetyl precursors notably include the trichloroacetyl group.

Alternatively, the N-protecting group may be chosen among those well known from those skilled in the art, provided that anchimeric assistance is ensured during construction of the B-C linkage.[23]

The OH groups of the residues may be protected by hydroxyl protecting groups. Suitable hydroxyl protecting groups are well known from those skilled in the art.[24] Examples of suitable hydroxyl protecting groups notably include benzyl (Bn), levulinoyl (Lev), para-methoxybenzyl (PMB), pivaloyl (Ply), chloroacetyl (ClAc), tert-butyldiphenylsilyl (TBDPS), 2-naphthylmethyl NAP, acetals in particular benzylidene acetal (Bzl).

More specifically, OH groups other than those at positions $3_C$, or those involved in a glycosidic linkage—that is those located at positions $4_A$, $3_B$, $2_C$ and $2_D$ of the corresponding non reducing terminal residue (acceptor site), may be protected in a so-called "permanent fashion", for example in the form of a benzyl ether (Bn) or benzylidene acetal (Bzl), whereas the aforementioned hydroxyl groups are protected by a so-called temporary/orthogonal protecting group, that is a protecting group that is selectively cleavable in the presence of the other protecting groups in place. Such temporary protecting groups are well known by the person skilled in the art,[24] and may in particular be independently selected from the group consisting of acetyl (Ac), chloro- or bromoacetyl (BrAc, ClAc), levulinoyl (Lev), benzoyl (Bz) possibly substituted, pivaloyl (PIV), para-methoxybenzyl (PMB), 2-naphthylmethyl (NAP), tert-butyldimethylsilyl (TBDMS), tert-butyldiphenylsilyl (TBDPS).

More specifically, hydroxyl groups located at position 2 of residues A, C and D—involved in the construction of the A-B, C-D and D-A glycosidic linkages, respectively—are selected among those able to ensure anchimeric assistance during the glycosylation step. Such protecting groups are well known of the person skilled in the art, and may in particular be independently selected from groups resulting in the formation of an ester, in particular from the set consisting of acetyl (Ac), chloro- or bromoacetyl (BrAc, ClAc), levulinoyl (Lev), benzoyl (Bz) possibly substituted, and pivaloyl (PIV).

In a certain aspect, there are included oligo- or polysaccharides (Ib) as defined herein, wherein $3_C$ is either 0-para-methoxybenzyl (i.e OPMB) or O-acetyl (i.e OAc), and $4_C$ is O-benzyl (i.e OBn).

In another embodiment, there are included oligo- or polysaccharides (Ib) as defined herein, wherein $4_A$, $3_B$, $2_C$ and $2_D$ of the homologous non reducing terminal residue (acceptor site) is OH, and the unique OH in the molecule, in fact an acceptor site.

In yet another embodiment, there are included oligo- or polysaccharides (Ib) as defined herein, wherein the $CO_2H$ moiety of the A residue(s) is(are) protected in the form of an ester orthogonal to an acetate, in particular a benzyl ester ($CO_2Bn$).

As used herein, the expression "ester orthogonal to an acetate", means that under specific reaction conditions, it is possible to chemo selectively cleave that ester function to unmask the $CO_2H$ moiety of the A residue(s)—within the oligo- or polysaccharides (Ib)—in the presence of an O-acetyl group at any of the $3_C$ or $4_C$-positions thereof.

$R^i$ of the reducing end residue may be a hydroxyl protecting group, notably selected from methyl (Me), allyl (All), para-methoxyphenyl (PMP), or a silyl moiety, preferably a 2-(trimethylsilyl)ethyl (SE), tert-butyldimethylsilyl (TBDMS) or tert-butyldiphenylsilyl (TBDPS).

As used herein, the wording "anomeric hydroxyl activating group" refers to a group able to make the anomeric hydroxyl group more reactive towards a nucleophile under appropriate conditions.[25] Examples of hydroxyl activating groups notably include imidates, such as trichloroacetimidoyl (TCA) or N-phenyltrifluoroacetimicloyl (PTFA), pentenyl, allyl, propargyl, phosphate, acetate, or an orthoester or oxazoline involving the O or N at position 2, in the case of residues A, C, or D and residue B, respectively.

These oligo- or polysaccharides are useful as intermediates for preparing the conjugates or the oligo- or polysaccharides (Ia) as defined above.

In a particular aspect there are included oligo- or polysaccharides (Ib) as defined herein, wherein n is 0 or 1.

In another aspect there are included oligo- or polysaccharides (Ib) as defined herein, wherein x and/or y is/are 0.

In a preferred aspect, there are included oligo- or polysaccharides (Ib) as defined herein, wherein W is $OR^i$ and $R^i$ is H, propyl, allyl, N-phenyltrifluoroacetimidoyl (PTFA).

In a preferred embodiment, there are included oligo- or polysaccharides (Ib) as defined herein selected from the group consisting of:

Propyl 2-acetamido-2-deoxy-β-D-galactopyranosyl-(1→2)-α-L-rhamnopyranosyl-(1→2)-α-L-rhamnopyranosyl-(1→4)-β-D-galactopyranosiduronic acid (XXX);

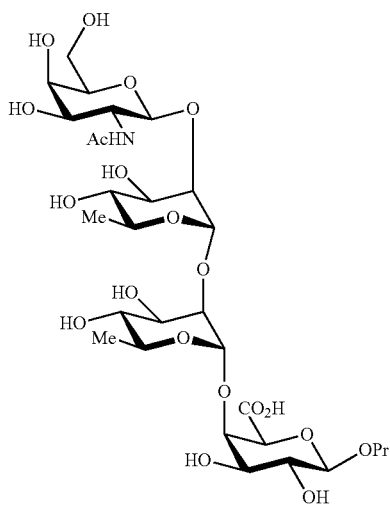

Propyl 2-acetamido-2-deoxy-β-D-galactopyranosyl-(1→2)-(3-O-acetyl-α-L-rhamnopyranosyl)-(1→2)-α-L-rhamnopyranosyl-(1→4)-β-D-galactopyranosiduronic acid (XXXI);

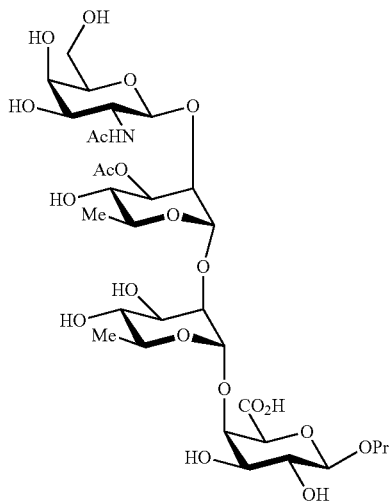

Propyl α-L-rhamnopyranosyl-(1→2)-α-L-rhamnopyranosyl-(1→4)-β-D-galactopyranosyluronic acid-(1→3)-2-acetamido-2-deoxy-β-D-galactopyranoside (XXXV);

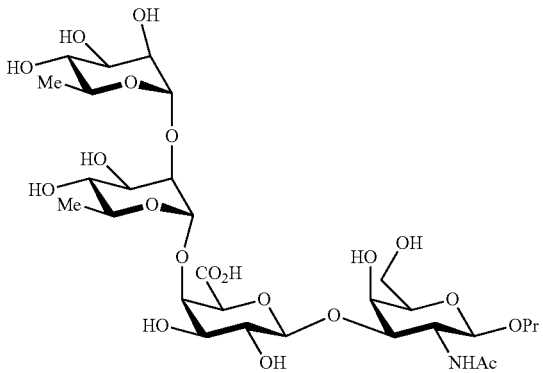

Propyl 3-O-acetyl-α-L-rhamnopyranosyl-(1→2)-α-L-rhamnopyranosyl-(1→4)-β-D-galactopyranosyluronic acid-(1→3)-2-acetamido-2-deoxy-β-D-galactopyranoside (XXXVI);

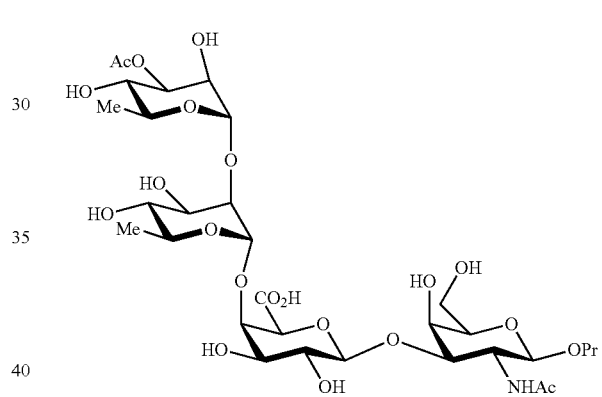

Propyl α-L-rhamnopyranosyl-(1→2)-α-L-rhamnopyranosyl-(1→4)-β-D-galactopyranosyluronic acid-(1→3)-2-acetamido-2-deoxy-β-D-galactopyranosyl-(1→2)-α-L-rhamnopyranoside (XX)

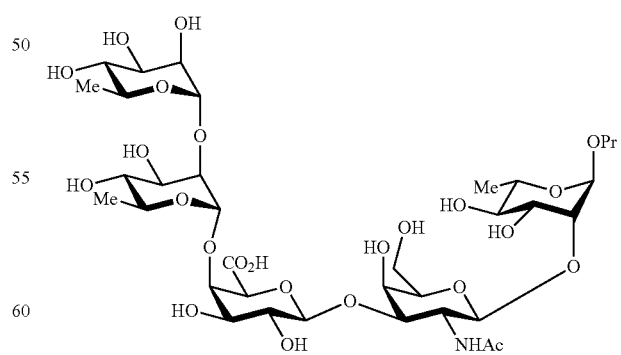

Propyl 3-O-acetyl-α-L-rhamnopyranosyl-(1→2)-α-L-rhamnopyranosyl-(1→4)-β-D-galactopyranosyluronic acid-(1→3)-2-acetamido-2-deoxy-β-D-galactopyranosyl-(1→2)-3-O-acetyl-α-L-rhamnopyranoside (XIX);

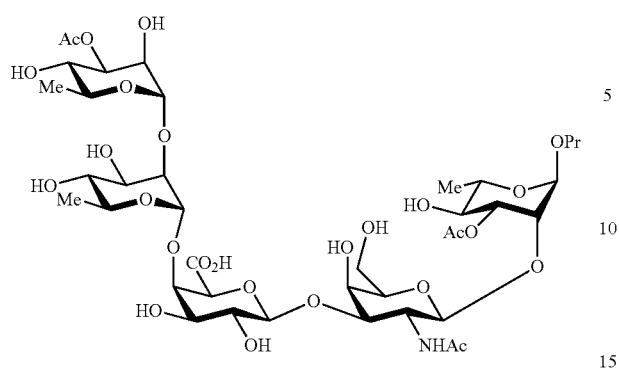

Propyl 2-O-acetyl-α-L-rhamnopyranosyl-(1→2)-α-L-rhamnopyranosyl-(1→4)-β-D-galactopyranosyluronic acid-(1→3)-2-acetamido-2-deoxy-β-D-galactopyranosyl-(1→2)-3-O-acetyl-α-L-rhamnopyranoside (XIX′)

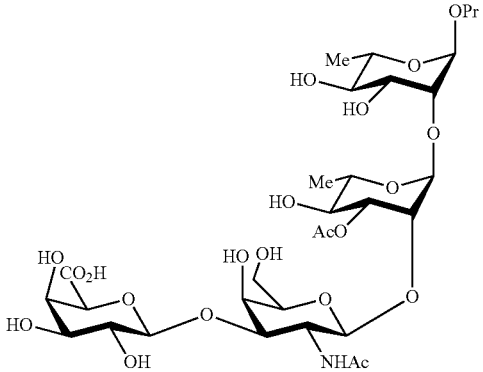

Propyl β-D-galactopyranosyluronic acid-(1→3)-2-acetamido-2-deoxy-3-D-galactopyranosyl-(1→2)-4-O-acetyl-α-L-rhamnopyranosyl-(1→2)-α-L-rhamnopyranoside (XII′);

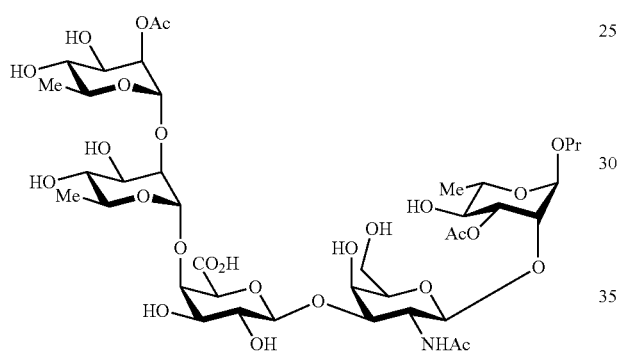

Propyl 4-O-acetyl-α-L-rhamnopyranosyl-(1→2)-α-L-rhamnopyranosyl-(1→4)-β-D-galactopyranosyluronic acid-(1→3)-2-acetamido-2-deoxy-β-D-galactopyranosyl-(1→2)-3-O-acetyl-α-L-rhamnopyranoside (XIX″).

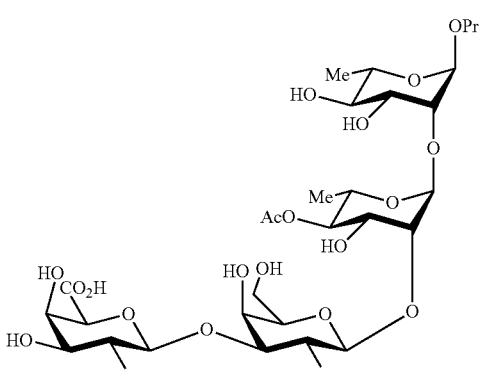

Propyl β-D-galactopyranosyluronic acid-(1→3)-2-acetamido-2-deoxy-β-D-galactopyranosyl-(1→2)-α-L-rhamnopyranosyl-(1→2)-α-L-rhamnopyranoside (XIV);

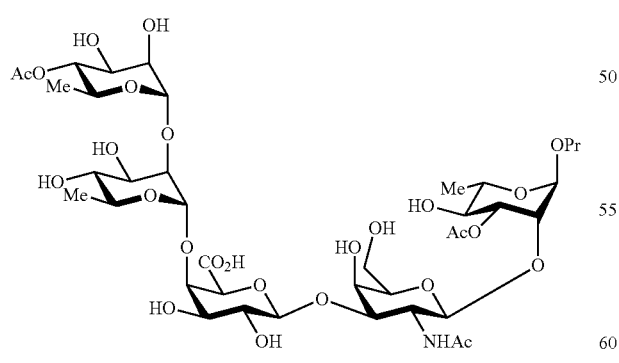

Propyl β-D-galactopyranosyluronic acid-(1→3)-2-acetamido-2-deoxy-β-D-galactopyranosyl-(1→2)-3-O-acetyl-α-L-rhamnopyranosyl-(1→2)-α-L-rhamnopyranoside (XII);

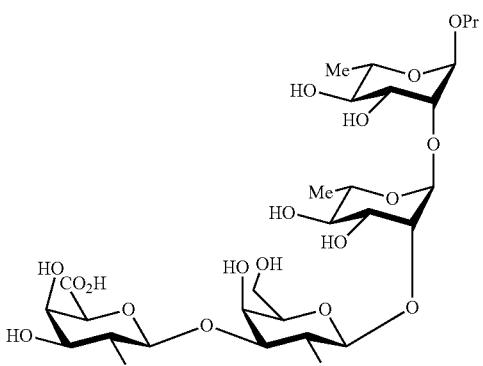

Propyl α-L-rhamnopyranosyl-(1→4)-β-D-galactopyranosyluronic acid-(1→3)-2-acetamido-2-deoxy-β-D-galactopyranosyl-(1→2)-3-O-acetyl-α-L-rhamnopyranoside (XV);

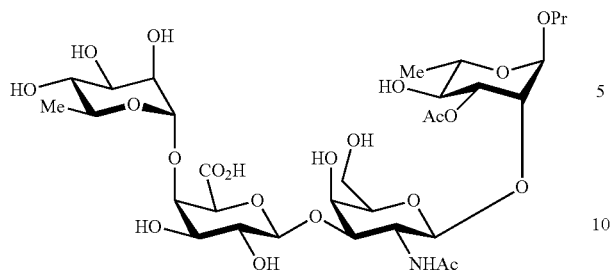

Propyl α-L-rhamnopyranosyl-(1→4)-3-D-galactopyranosyluronic acid-(1→3)-2-acetamido-2-deoxy-β-D-galactopyranosyl-(1→2)-4-O-acetyl-α-L-rhamnopyranoside (XV');

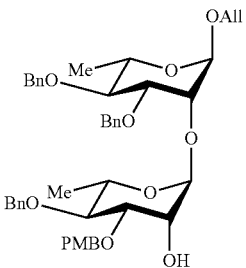

Benzyl (4-O-benzyl-3-O-para-methoxybenzyl-α-L-rhamnopyranosyl)-(1→2)-(3,4-di-O-benzyl-α-L-rhamnopyranosyl)-(1→4)-(allyl 2,3-di-O-benzyl-β-D-galactopyranosid)uronate (169), also designated HO-CDA,

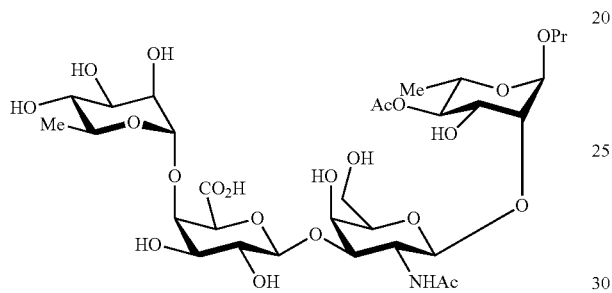

Propyl α-L-rhamnopyranosyl-(1→4)-β-D-galactopyranosyluronic acid-(1→3)-2-acetamido-2-deoxy-β-D-galactopyranosyl-(1→2)-α-L-rhamnopyranoside (XVI);

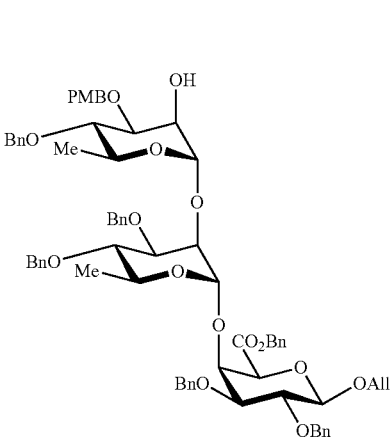

Allyl (4-O-benzyl-3-O-para-methoxybenzyl-α-L-rhamnopyranosyl)-(1→2)-(3,4-di-O-benzyl-α-L-rhamnopyranosyl)-(1→4)-(benzyl 2,3-di-O-benzyl-β-D-galactopyranosyluronate)-(1→3)-4,6-di-O-benzyl-2-deoxy-2-trichloroacetamido-β-D-galactopyranoside (280), also designated HO-CDAB,

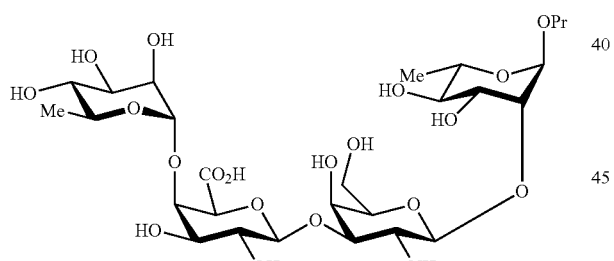

In a further object, it is herein disclosed oligosaccharides (ft) selected from the group consisting of:

Allyl 4-O-benzyl-3-O-para-methoxybenzyl-α-L-rhamnopyranoside (9), also designated HO-C,

Allyl (4-O-benzyl-3-O-para-methoxybenzyl-α-L-rhamnopyranosyl)-(1→2)-3,4-di-O-benzyl-α-L-rhamnopyranoside (48), also designated HO-CD, Phenyl 3,4,6-tri-O-benzyl-2-deoxy-2-trichloroacetamido-1-thio-β-D-galactopyranoside (24), also designated B-SPh,

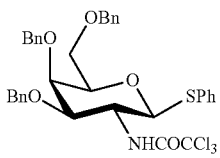

3,4,6-Tri-O-benzyl-2-deoxy-2-trichloroacetamido-α/β-D-galactopyranosyl N-phenyltrifluoroacetimidate (181), also designated B-PTFA,

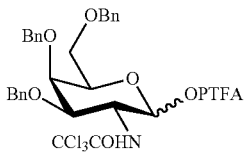

Chemical Formula: $C_{37}H_{34}Cl_3F_3N_2O_6$
Exact Mass: 764,1435
Molecular Weight: 766,0299
Allyl (2,3-di-O-benzyl-β-D-galactopyranosyl)-(1→3)-4,6-di-O-benzyl-2-deoxy-2-trichloroacetamido-β-D-galactopyranoside (241), also designated (HO)$_2$-AB

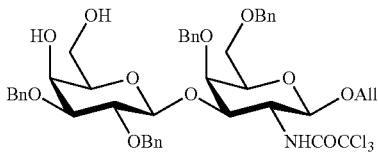

Chemical Formula: $C_{45}H_{50}Cl_3NO_{11}$
Exact Mass: 885,2449
Molecular Weight: 887,2376
(Benzyl 2,3-di-O-benzyl-4-O-levulinoyl-β-D-galactopyranosyluronate)-(1→3)-4,6-di-O-benzyl-2-deoxy-2-trichloroacetamido-α-D-galactopyranosyl trichloroacetimidate (246), also designated AB-TCA,

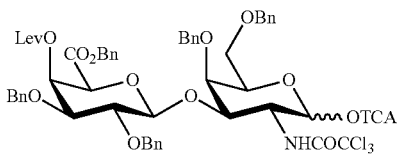

Chemical Formula: $C_{56}H_{56}Cl_6N_2O_{14}$
Exact Mass: 1190,1863
Molecular Weight: 1193,7668
Benzyl 2,3-di-O-benzyl-4-O-levulinoyl-β-D-galactopyranosyluronate-(1→3)-4,6-di-O-benzyl-2-deoxy-2-trichloroacetamido-α/β-D-galactopyranosyl N-phenyltrifluoroacetimidate (247), also designated AB-PTFA,

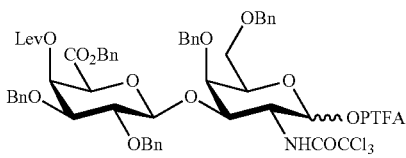

Chemical Formula: $C_{62}H_{60}Cl_3F_3N_2O_{14}$
Exact Mass: 1218,3062
Molecular Weight: 1220,4990

(3,4-Di-O-benzyl-2-O-levulinoyl-α-L-rhamnopyranosyl)-(1→4)-(benzyl 2,3-di-O-benzyl-β-D-galactopyranosyluronate)-(1→3)-4,6-di-O-benzyl-2-deoxy-2-trichloroacetamido-α/β-D-galactopyranosyl N-phenyltrifluoroacetimidate (283), also designated DAB-PTFA,

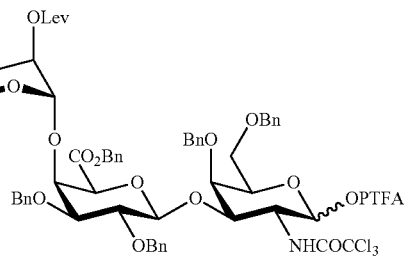

Chemical Formula: $C_{82}H_{82}Cl_3F_3N_2O_{18}$
Exact Mass: 1544,4580
Molecular Weight: 1546,8853
(4-O-Benzyl-3-O-para-methoxybenzyl-2-O-levulinoyl-α-L-rhamnopyranosyl)-(1→2)-(3,4-di-O-benzyl-α-L-rhamnopyranosyl)-(1→4)-(benzyl 2,3-di-O-benzyl-β-D-galactopyranosyluronate)-(1→3)-4,6-di-O-benzyl-2-deoxy-2-trichloroacetamido-α/β-D-galactopyranosyl N-phenyltrifluoroacetimidate (284), also designated CDAB-PTFA,

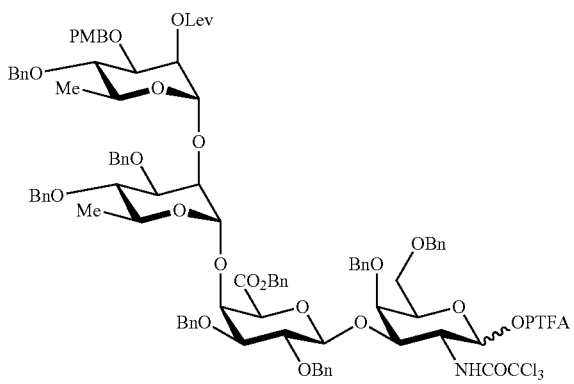

Chemical Formula: $C_{103}H_{106}Cl_3F_3N_2O_{23}$
Exact Mass: 1900,6204
Molecular Weight: 1903,2975
Allyl (benzyl 2,3-di-O-benzyl-4-O-levulinoyl-β-D-galactopyranosyluronate)-(1→3)-4,6-di-O-benzyl-2-deoxy-2-trichloroacetamido-β-D-galactopyranoside (244), also designated AB

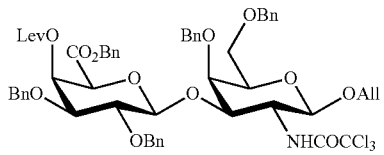

Chemical Formula: $C_{57}H_{60}Cl_3NO_{14}$
Exact Mass: 1087,3079
Molecular Weight: 1089,4436
Allyl (benzyl 2,3-di-O-benzyl-β-D-galactopyranosyluronate)-(1→3)-4,6-di-O-benzyl-2-deoxy-2-trichloroacetamido-β-D-galactopyranoside (242), also designated HO-AB,

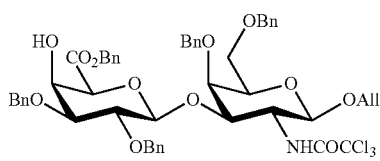

Chemical Formula: $C_{52}H_{54}Cl_3NO_{12}$
Exact Mass: 989,2712
Molecular Weight: 991,3437
(Benzyl 2,3-di-O-benzyl-4-O-levulinoyl-β-D-galactopyranosyluronate)-(1→3)-4,6-di-O-benzyl-2-deoxy-2-trichloroacetamido-α/β-D-galactopyranose (245), also designated AB-OH.

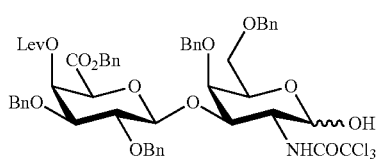

Chemical Formula: $C_{54}H_{56}Cl_3NO_{14}$
Exact Mass: 1047,2766
Molecular Weight: 1049,3797

Oligo- or polysaccharides (Ic) are particularly advantageous as they provide an efficient access to oligo- or polysaccharides having more than one repeating unit (Ib) and (Ia) in a reduced number of steps, according to a convergent synthesis. In particular, oligo- or polysaccharides (Ic) can be divided into two groups: acceptors, which define the reducing end of the polysaccharide chain and donors, which are generally involved in chain elongation and, in particular, which set the non reducing end of the polysaccharide chain. Selected exemples of preferred donors and acceptors are listed in Table I.

As used herein, the term "donor" more particularly refers to a mono-, oligo- or polysaccharide bearing a leaving group at the anomeric position.

As used herein, the term "acceptor" more particularly refers to a mono-, oligo- or polysaccharide having at least a free hydroxyl group, in general other than the anomeric hydroxyl, preferably a single free hydroxyl group corresponding to the elongation site of the growing chain.

TABLE I

DONORS

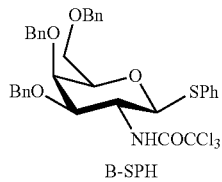

24

B-SPH

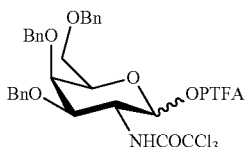

181

B-PTFA

TABLE I-continued

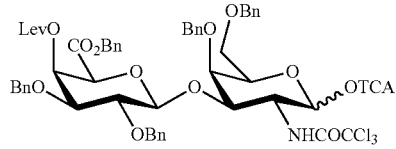

246

AB-TCA

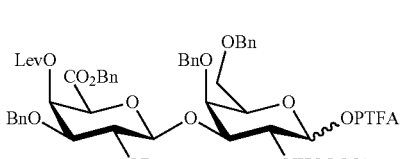

247

AB-PTFA

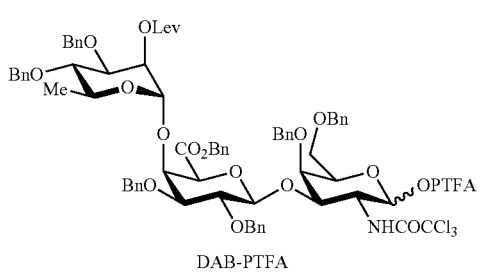

283

DAB-PTFA

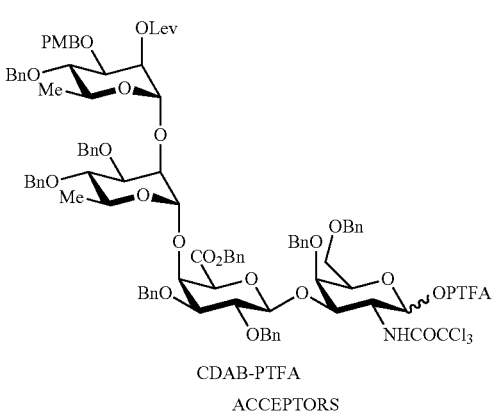

284

CDAB-PTFA

ACCEPTORS

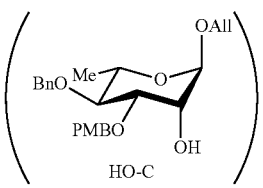

9

HO-C

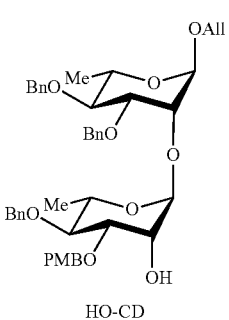

48

HO-CD

TABLE I-continued

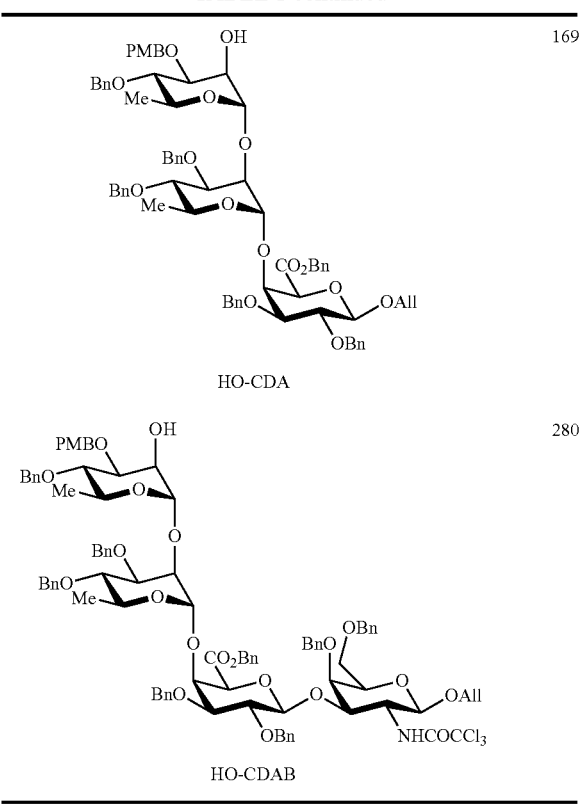

169 HO-CDA

280 HO-CDAB (acceptor HO-C (9) is a known precursor[26])

As a theoretical example which follows, the octasaccharide bearing a C residue at the reducing end may be prepared by coupling selected acceptor and donor building blocks among those (ft) listed above (Table I). Alternatively, oligo- or polysaccharides (h) bearing a D residue at their reducing end may be obtained by use of an appropriate set of donors (Ic) listed in table I in combination with the HO-CD acceptor (48). In this case, the CDAB-PTFA donor is used iteratively as many time as needed (γ) to reach the appropriate chain length:

As a further example, the octasaccharide [CDAB]$_2$ (300) may be prepared according to a method comprising a step of coupling the tetrasaccharide acceptor HO-CDAB (280) with the tetrasaccharide donor CDAB-PTFA (284). Such a method may be illustrated by the following scheme.

Scheme 1

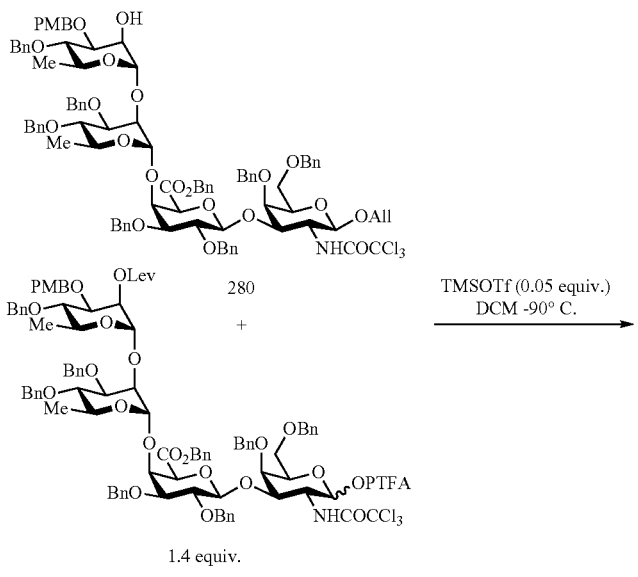

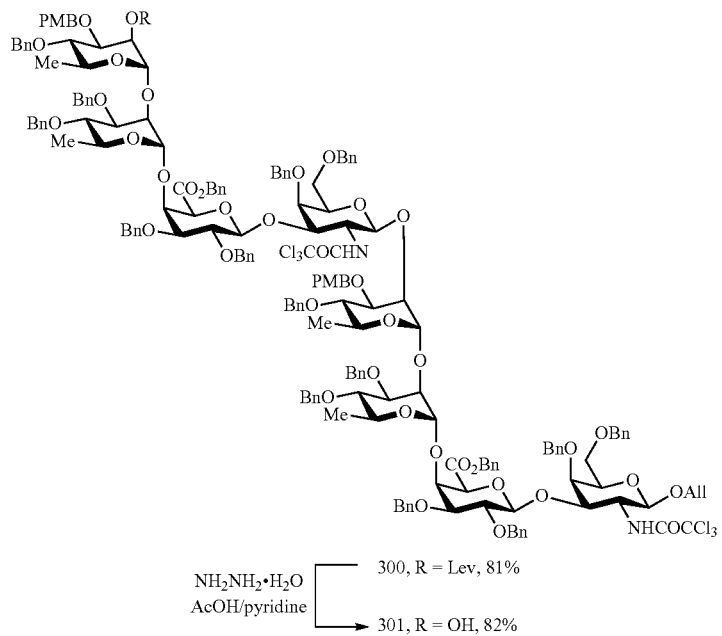
NH$_2$NH$_2$·H$_2$O
AcOH/pyridine
300, R = Lev, 81%
301, R = OH, 82%
As a further example, the dodecasaccharide [CDAB]$_3$ (302) may be prepared according to a method comprising a step of coupling the octasaccharide acceptor HO-[CDAB]$_2$ (301) with the tetrasaccharide donor CDAB-PTFA (284). Such a method may be illustrated by the following scheme.
Scheme 2
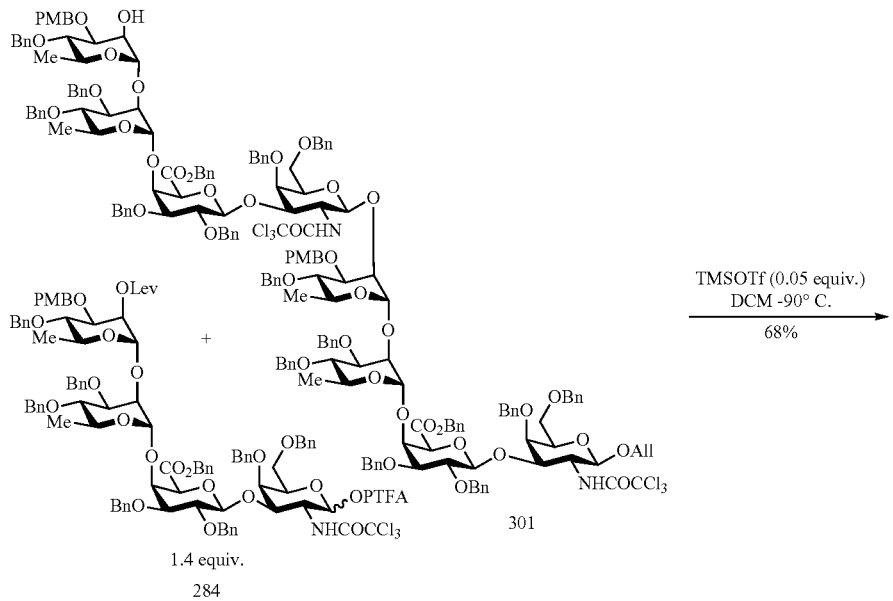
TMSOTf (0.05 equiv.)
DCM -90° C.
68%

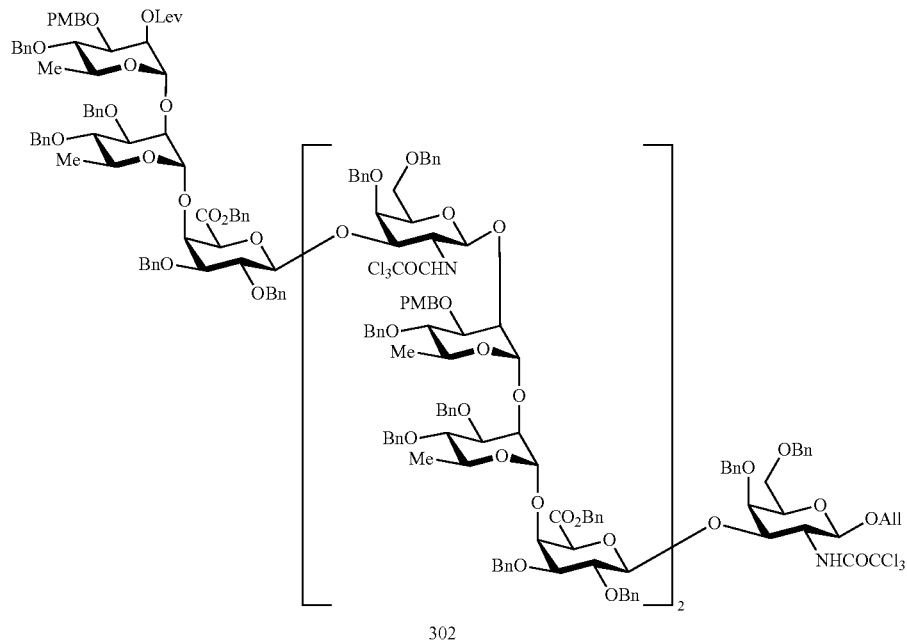
302
As a further example, the pentasaccharide ABCDA (248) may be prepared according to a method comprising a step of coupling the trisaccharide acceptor HO-CDA (169) with the disaccharide donor AB-TCA (246) or AB-PTFA (247). Such a method may be illustrated by the following scheme.
Scheme 3
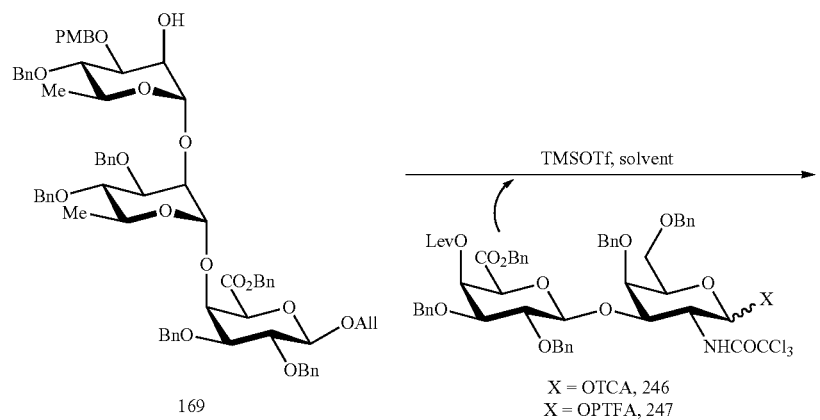

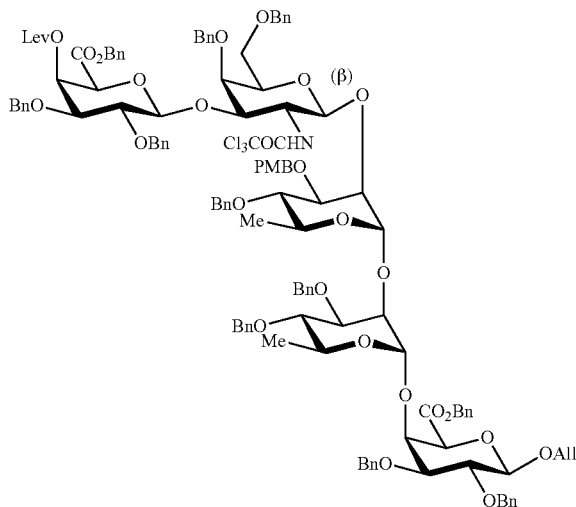
248
77%-87%
As a further example, the heptasaccharide DABCDAB (294) may be prepared according to a method comprising a step of coupling the tetrasaccharide acceptor HO-CDAB (280) with the trisaccharide donor DAB-PTFA (283). Such a method may be illustrated by the following scheme.
Scheme 4
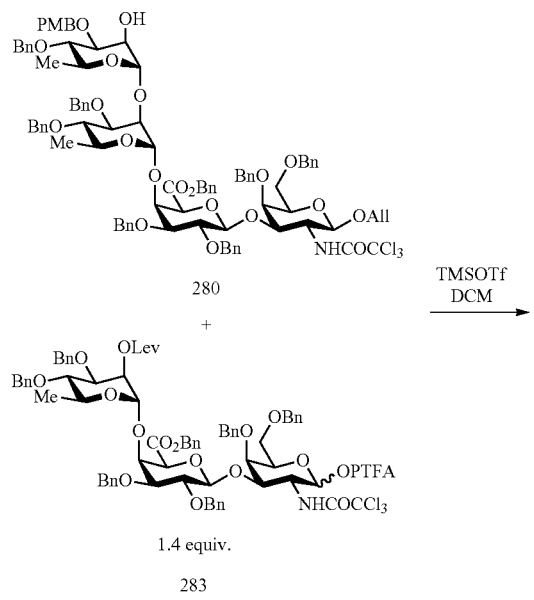

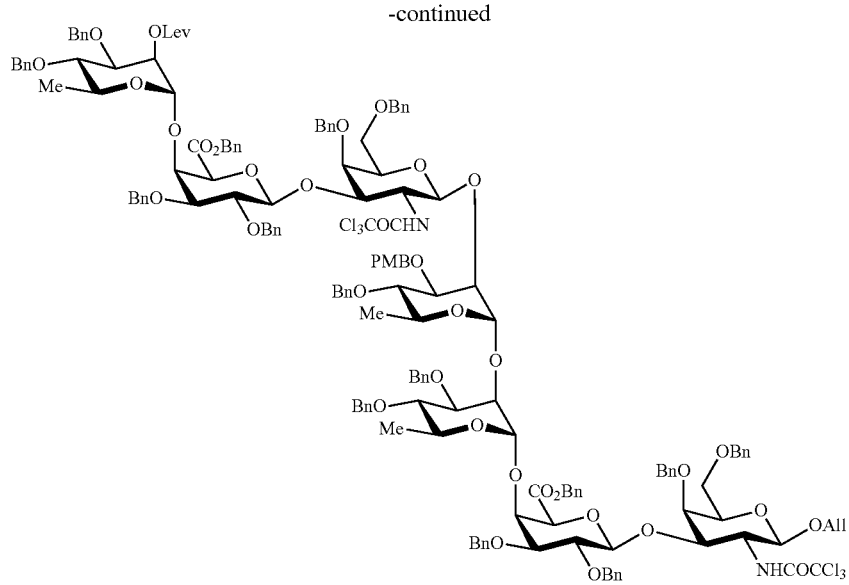

294

In a further aspect, the invention provides a disaccharide of formula (II):

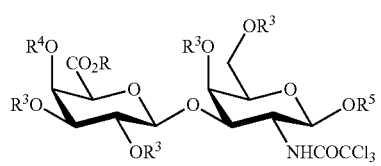

(II)

Wherein:

R is an ester protecting group, preferentially cleavable upon hydrogenolysis, such as a benzyl, $R^3$ is a permanent hydroxyl protecting group, preferentially a benzyl ether, $R^4$ is H or a temporary protecting group, in particular orthogonal to allyl and a benzyl ester ($CO_2Bn$), which may be independently selected amongst the following non exhaustive set consisting of levulinoyl, chloroacetyl, substituted benzoyl—such as for example AZMB—silyl ether, $R^5$ is allyl, H, N-trichloroacetimidoyl (TCA), or Nphenyltrifluoroacetimidoyl (PTFA), provided that $R^4$ and $R^5$ are not H simultaneously.

Disaccharides of formula (II), notably disaccharides 242, 244, 245, 246 and 247 are particularly advantageous as key intermediates to access oligo- and polysaccharides (Ib) and (Ia).

In a further aspect, the invention provides a use of an oligo- or polysaccharide (Ib) or (Ic) as defined herein, as an intermediate for the preparation of an oligo- or polysaccharide (Ia) as defined herein, or of a conjugate as defined above.

Definitions

The following terms and expressions used herein have the indicated meanings.

"Oligosaccharide" as defined herein, is a carbohydrate containing from two to twenty monosaccharide units linked together, "oligosaccharide" is used herein in a liberal manner to denote the saccharides described herein; this usage differs from the standard definition that oligosaccharides may contain up to and including ten monosaccharide units (Joint Commission on Biological Nomenclature, Eur. J. Biochem. 1982, 126, 433-437).

"Polysaccharide" as defined herein, is a carbohydrate containing more than twenty monosaccharide subunits linked together.

"Reducing end" as defined herein, refers to the end of an oligo- or polysaccharide with an anomeric carbon ($C_1$) that is not involved in a glycosidic bond with another sugar residue.

"Carrier" refers to any molecule which can be covalently or uncovalently bound to an oligo- or polysaccharide of the invention to form a glycoconjugate of the invention. It includes immunocarriers for use as vaccines and other carriers for preparing diagnostic reagents.

"Immunocarrier" refers to an immunogenic molecule or a fragment of a molecule, which is recognized by T-helper cells and is able to contribute to the antibody response by inducing antibody affinity maturation, IgM to IgG isotype switch, and B cell memory.

"Other carriers for preparing diagnostic reagents" refers to agents commonly used to immobilize molecules onto a solid phase, to generate a multivalent display, or to label molecules.

"Label" refers to any substance which can produce a signal which can be detected by any appropriate mean.

"Glycoconjugate" refers to a conjugate as defined herein.

"Prevention and treatment" refers to the prevention of infection or reinfection, reduction or elimination of the symptoms, and reduction or complete elimination of the pathogen. Treatment may be effected prophylactically (prior to infection) or therapeutically (following infection).

"Alkyl" refers to a linear-chain, or branched alkyl group having 1 to 6 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, etc.

"Alkoxy" refers to an Alkyl-O— group, wherein the alkyl group is as defined herein.

"Aryl" refers to a mono- or bicyclic hydrocarbon aromatic ring system having 6 to 10 ring carbon atoms. Examples include phenyl and naphthyl.

"Hal" refers to an halogen atom, namely F, Cl, Br and I.

The following abbreviations used herein have the indicated meanings.

Ac: acetyl
All: allyl
anhyd.: anhydrous
aq.: aqueous
Ar: argon
AW: acid washed
Bn: benzyl
calcd: calculated
CAN: cerium ammonium nitrate
Chex: cyclohexane
DBU: 1,8-diazabicyclo[5.4.0]undec-7-ene
DCC: 1,3-dicyclohexylcarbodiimide
DCE: 1,2-dichloroethane
DCM: dichloromethane
DMAP: N,N-dimethylaminopyridine
ESI: electrospray ionization
h: hour
HPLC: high performance liquid chromatography
HRMS: high resolution mass spectrometry
Lev: levulinoyl
LC-MS: Liquid chromatography mass spectrometry
LPS: lipopolysaccharide
Me: methyl
min: minute
MS: molecular sieves
NMR: nuclear magnetic resonance
O—Ag: O-antigen
Ph: phenyl
PMB: para-methoxybenzyl
PTFA: N-phenyltrifluoroacetimidoyl
Rf: retardation factor
Rt: Retention time
RP: reverse phase
rt: room temperature
SF6: *Shigella flexneri* serotype 6
SF6a: *Shigella flexneri* serotype 6a
TBAI: tetrabutylammonium bromide
TCA: trichloroacetimidate
TEMPO: (2,2,6,6-tetramethylpiperidin-1-yl)oxyl
TFA: trifluoroacetic acid
THF: tetrahydrofuran
TLC: thin layer chromatography
TMSOTf: trimethylsilyl trifluoromethanesulfonate
Tol: toluene Other features of the invention will become apparent in the course of the following description of exemplary embodiments. These examples are given for illustration of the invention and are not intended to be limiting thereof.

EXAMPLES

I. Synthesis of Oligo- and/or Polysaccharides

General Methods:

Nuclear magnetic resonance (NMR) spectra were recorded at 303 K on a Bruker Avance spectrometer at 400 MHz ($^1$H) and 100 MHz ($^{13}$C) equipped with a BBO probe. Signals are reported as m (multiplet), s (singlet), d (doublet), t (triplet), dd (doublet of doublet), q (quadruplet), qt (quintuplet), sex (sextuplet), dt (doublet of triplet), dq (doublet of quadruplet), ddd (doublet of doublet of doublet), m (multiplet). The signals can also be described as broad (prefix b), pseudo (prefix p), overlapped (suffix $_o$) or partially overlapped (suffix $_{po}$) The coupling constants are reported in hertz (Hz). The chemical shifts are reported in ppm (δ) relative to residual solvent peak. Of the two magnetically non-equivalent geminal protons at C-6, the one resonating at lower field is denoted H-6a, and the one at higher field is denoted H-6b. Interchangeable assignments are marked with an asterisk. Sugar residues are lettered according to the lettering of the repeating unit of the SF6 O—Ag (A, B, C and D) and identified by a subscript in the listing of signal assignments. For oligosaccharides larger than one repeating unit, the A, B, C, D lettering is turned into A', B', C', if and A", B", C", D", starting with A, B, C, D from the reducing end.

HRMS spectra were recorded on a WATERS QTOF Micromass instrument in the positive-ion electrospray ionisation (ESI$^+$) mode. Solutions were prepared using 1:1 MeCN/H$_2$O containing 0.1% formic acid.

Analytical RP-HPLC analyses of the final compounds were run on an Agilent 1200 Series instrument equipped with a UV detector (λ=215 nm) and a Symmetry 3.5 μm C$_{18}$ 100 Å 2.1×100 mm analytical column eluting with a 0-35% linear gradient of MeCN in 0.01 N aq. TFA over 20 min at a flow rate of 0.3 mL·min$^{-1}$).

A. Linear Synthetic Strategy

Linear synthesis stands for a process whereby the chain elongation required to obtain the oligo- or polysaccharide target involves the predetermined ordered glycosylation of an acceptor with one residue at a time in alternance with the selective unmasking of the site of subsequent glycosylation within the newly introduced residue.

Example of a Linear Synthesis: Access to Tetrasaccharides BCDA-Pr (XXX) and B$_{Ac}$CDA-Pr (XXXI)

Scheme 5

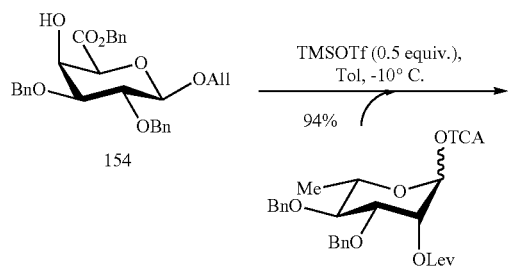

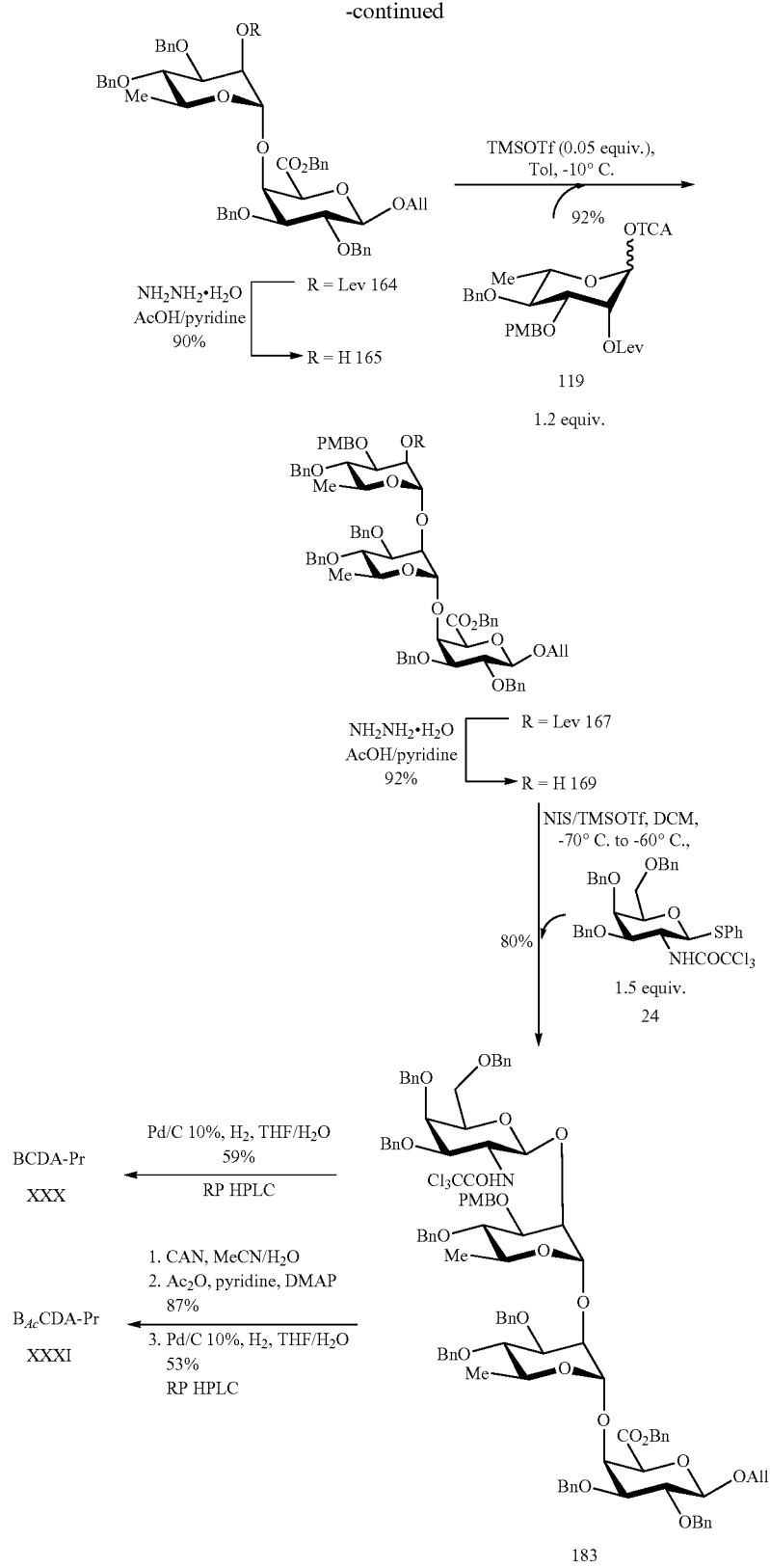
The galacturonate acceptor 154 (A) is first glycosylated with the rhamnosyl trichloroacetimidate donor 92 (D) to give the fully protected disaccharide 164. The site of elongation is selectively deprotected, turning this disaccharide into an acceptor (165). The newly synthesized 165 is reacted, under selected imidate-based glycosylation conditions, with a second rhamnosyl donor 119 that is a precursor to residue C. Interestingly, its 3-OH is orthogonally protected in the form of a para-methoxybenzyl ether. Hydrazinolysis of the single levulinoyl ester of the resulting trisaccharide allowed the selective unmasking of the $2_C$-OH, thus turning the glycosylation product 167 into acceptor 169. Glycosylation of trisaccharide 169 with the galactosaminyl residue 24 (B), in this case a thioglycoside donor, provided the β-linked glycosylation product 183 as required. The fully protected tetrasaccharide 183 was submitted to a two step process involving first the oxidative cleavage of the PMB ether, and then the acetylation of the thus unmasked $3_C$-OH to give the 3-OAc analogue 187. Treatment of tetrasaccharides 183 and 187 with Pd/C in a hydrogen atmosphere led to propyl glycosides XXX and XXXI, issued from the hydrogenolysis of the benzyl ester, benzyl and when needed para-methoxybenzyl ethers in concomitance with the trichloroacetamide to acetamide and allyl to propyl reduction. Tetrasaccharide XXX and its $3_C$-OAc analogue XXXI are synthetic frame-shifted mimics of the biological repeating unit of SF6, SF6a and/or E. coli O147 O-antigens.

Benzyl (3,4-di-O-benzyl-2-O-levulinoyl-α-L-rhamnopyranosyl)-(1→4)-(allyl 2,3-di-O-benzyl-β-D-galactopyranoside)uronate (164)

A suspension of acceptor 154[27] (300 mg, 595 μmol), trichloroacetimidate 92[28] (419 mg, 713 μmol) and freshly activated 4 AW 300 MS (450 mg) in anhyd. toluene (5.9 mL) was stirred for 1 h at rt under an Ar atmosphere. The reaction mixture was cooled to −10° C., and TMSOTf (5 μL, 30 μmol) was added. The reaction mixture was stirred at that temperature for 30 min. The reaction was quenched by adding Et$_3$N. The resulting mixture was filtered and the filtrate was concentrated. The residue was purified by flash chromatography (Tol/Acetone 97:3 to 96:4) to give disaccharide 164 (519 mg, 94%) as a white oil.

$^1$H NMR (CDCl$_3$), δ 7.41-7.23 (m, 25H, H$_{Ar}$), 5.99 (m, 1H, CH$_{All}$), 5.55 (dd, 1H, J$_{1,2}$=2.1 Hz, J$_{2,3}$=3.3 Hz, H-2$_D$), 5.36 (m, 1H, J$_{trans}$=17.2 Hz, J$_{gem}$=1.5 Hz, =CH$_{2All}$), 5.28 (d, 1H, J=12.3 Hz, H$_{CO2Bn}$) 5.24-5.20 (m, 2H, H-1$_D$, =CH$_{2All}$), 5.12 (d, 1H, H$_{CO2Bn}$), 4.94 (d, 1H, J=11.0 Hz, H$_{Bn}$), 4.91 (d, 1H, J=11.2 Hz, H$_{Bn}$), 4.79 (d, 1H, J=11.0 Hz, H$_{Bn}$), 4.77 (d, 1H, J=12.1 Hz, H$_{Bn}$), 4.74 (d, 1H, J=12.1 Hz, H$_{Bn}$), 4.64 (d, 1H, J=11.1 Hz, H$_{Bn}$), 4.61 (d, 1H, J=11.2 Hz, H$_{Bn}$), 4.50 (m, 1H, H$_{All}$), 4.45 (d, 1H, J=11.0 Hz, H$_{Bn}$), 4.43-4.39 (m, 2H, H-4$_A$, H-1$_A$), 4.17 (m, 1H, H$_{All}$), 4.05 (bs, 1H, H-5$_A$), 3.88 (dd, 1H, J$_{3,4}$=9.4 Hz, H-3$_D$), 3.80-3.71 (m, 2H, H-2$_A$, H-5$_D$), 3.56 (dd, 1H, J$_{2,3}$=9.7 Hz, J$_{3,4}$=2.9 Hz, H-3$_A$), 3.37 (pt, 1H, J$_{4,5}$=9.4 Hz, H-4$_D$), 2.72-2.62 (m, 4H, CH$_{2Lev}$), 2.16 (s, 3H, CH$_{3Lev}$), 1.30 (d, 3H, J$_{5,6}$=6.2 Hz, H-6$_D$).

$^{13}$C NMR (CDCl$_3$) partial, δ 206.4 (CO$_{Lev}$), 171.6 (CO$_{2Lev}$), 167.4 (C-6$_A$), 102.6 (C-1$_A$, $^1$J$_{CH}$=161.3 Hz), 98.9 (C-1$_D$, $^1$J$_{CH}$=172.7 Hz), 67.4 (C$_{CO2Bn}$), 38.1 (COCH$_{2Lev}$), 29.9 (CH$_{3Lev}$), 28.2 (CO$_2$CH$_{2Lev}$).

HRMS (ESI$^+$): m/z 951.3846 (calcd for C$_{55}$H$_{60}$O$_{13}$Na [M+Na]$^+$: m/z 951.3932).

Benzyl (3,4-di-O-benzyl-α-L-rhamnopyranosyl)-(1→4)-(allyl 2,3-di-O-benzyl-β-D-galactopyranosid) uronate (165)

To a solution of disaccharide 164 (1.25 g, 1.35 mmol) in dry pyridine (8.3 mL) stirred at 0° C. under an Ar atmosphere was slowly added acetic acid (5.6 mL) followed by hydrazine monohydrate (326 μL, 6.73 mmol). The reaction mixture was stirred at rt for 1.5 h. Volatiles were evaporated and co-evaporated twice with toluene. The residue was taken up in DCM and washed with water. The aq. layer was re-extracted twice with DCM, and the combined organic phases were washed with brine, passed through a phase separator filter and concentrated. The residue was purified by flash chromatography (Chex/EtOAc 8:2 to 7:3) to give alcohol 165 (1.05 g, 90%) as a light yellow oil.

$^1$H NMR (CDCl$_3$), δ 7.42-7.27 (m, 25H, H$_{Ar}$), 6.01 (m, 1H, CH$_{All}$), 5.39 (d$_o$, 1H, J$_{1,2}$=1.7 Hz, H-1$_D$), 5.38 (m, 1H, J$_{trans}$=17.2 Hz, J$_{gem}$=1.6 Hz, =CH$_{2All}$), 5.32 (d, 1H, J=12.2 Hz, H$_{CO2Bn}$), 5.25 (m, 1H, J$_{cis}$=10.5 Hz, =CH$_{2All}$), 5.14 (d, 1H, H$_{CO2Bn}$), 4.96 (d, 1H, J=11.0 Hz, H$_{Bn}$), 4.90 (d, 1H, J=11.3 Hz, H$_{Bn}$), 4.80 (d$_{po}$, 1H, J=11.9 Hz, H$_{Bn}$), 4.76 (d$_{po}$, 1H, J=10.9 Hz, H$_{Bn}$), 4.75 (d$_{po}$, 1H, J=11.9 Hz, H$_{Bn}$), 4.67-4.64 (m, 3H, H$_{Bn}$), 4.54 (m, 1H, H$_{All}$), 4.49 (dd, 1H, H-4$_A$), 4.43 (d, 1H, J$_{1,2}$=7.8 Hz, H-1$_A$), 4.23-4.16 (m, 2H, H-2$_D$ H$_{All}$), 4.08 (d, 1H, J$_{4,5}$=1.2 Hz, H-5$_A$), 3.89 (dd, 1H, J$_{2,3}$=3.2 Hz, J$_{3,4}$=9.0 Hz, H-3$_D$), 3.80-3.71 (m, 2H, H-2$_A$, H-5$_D$), 3.58 (dd, 1H, J$_{2,3}$=9.8 Hz, J$_{3,4}$=3.0 Hz, H-3$_A$), 3.47 (pt, 1H, J$_{4,5}$=9.3 Hz, H-4$_D$), 2.43 (bs, 1H, OH), 1.32 (d, 3H, J$_{5,6}$=6.2 Hz, H-6$_D$).

$^{13}$C NMR (CDCl$_3$) partial, δ 167.3 (C-6$_A$), 102.7 (C-1$_A$, $^1$J$_{CH}$=159.4 Hz), 100.4 (C-1$_D$, $^1$J$_{CH}$=172.7 Hz), 67.3 (C$_{CO2Bn}$)

HRMS (ESI$^+$): m/z 853.3478 (calcd for C$_{50}$H$_{54}$O$_{11}$Na [M+Na]$^+$: m/z 853.3564).

Benzyl (4-O-benzyl-3-O-para-methoxybenzyl-2-O-levulinoyl-α-L-rhamnopyranosyl)-(1→2)-(3,4-di-O-benzyl-α-L-rhamnopyranosyl)-(1→4)-(allyl 2,3-di-O-benzyl-β-D-galactopyranosid)uronate (167)

A mixture of acceptor 165 (300 mg, 361 μmol), trichloroacetimidate 119 (267 mg, 433 μmol) and freshly activated 4 powdered MS (750 mg) in anhyd. toluene (10.8 mL) was stirred for 1 h at rt under an Ar atmosphere. The reaction mixture was cooled to −10° C., and TMSOTf (3.3 μL, 18 μmol) was added. The reaction mixture was stirred at that temperature for 20 min. The reaction was quenched by adding Et$_3$N. The resulting suspension was filtered and concentrated. The residue was purified by flash chromatography (Tol/EtOAc 95:5 to 85:15) to give trisaccharide 167 (426 mg, 91%) as a light yellow oil.

$^1$H NMR (CDCl$_3$), δ 7.43-7.17 (m, 32H, H$_{Ar}$), 6.86 (d, 2H, J=8.5 Hz, H$_{ArPMB}$), 5.99 (m, 1H, CH$_{All}$), 5.52 (dd, 1H, J$_{1,2}$=1.9 Hz, J$_{2,3}$=3.1 Hz, H-2$_C$), 5.36 (m, 1H, J$_{trans}$=17.2 Hz, J$_{gem}$=1.6 Hz, =CH$_{2All}$), 5.33 (bs$_o$, 1H, H-1$_D$), 5.27 (d, 1H, J=12.2 Hz, H$_{CO2Bn}$), 5.22 (m, 1H, J$_{cis}$=10.5 Hz, =CH$_{2All}$), 5.12 (d, 1H, H$_{CO2Bn}$), 4.94 (d$_{po}$, 1H, J=11.1 Hz, H$_{Bn}$), 4.92-4.88 (m$_o$, 3H, H-1$_C$, 2H$_B$), 4.80 (d, 1H, J=12.1 Hz, H$_{Bn}$), 4.75 (d, 1H, J=12.1 Hz, H$_{Bn}$), 4.70-4.57 (m, 6H, H$_{Bn}$), 4.50 (m$_{po}$, 1H, H$_{All}$), 4.48 (d, 1H, J=10.9 Hz, H$_{Bn}$), 4.39 (m$_o$, 1H, H-4$_A$), 4.38 (d$_o$, 1H, J$_{1,2}$=7.8 Hz, H-1$_A$), 4.17 (m, 1H, H$_{All}$), 4.11 (pt, 1H, H-2$_D$), 4.02 (d, 1H, J$_{4,5}$=1.0 Hz, H-5$_A$), 3.94 (dd, 1H, J$_{3,4}$=9.3 Hz, H-3$_C$), 3.86 (dd$_{po}$, 1H, J$_{2,3}$=2.9 Hz, J$_{3,4}$=9.4 Hz, H-3$_D$), 3.82 (dq, 1H, H-5$_C$), 3.78 (s, 3H, CH$_{3PMB}$), 3.75-3.64 (m, 2H, H-2$_A$, H-5$_D$), 3.51 (dd, 1H, J$_{2,3}$=9.8 Hz, J$_{3,4}$=2.8 Hz, H-3$_A$), 3.42 (pt, 1H, J$_{4,5}$=9.5 Hz, H-4$_D$), 3.37 (pt, 1H, J$_{4,5}$=9.5 Hz, H-4$_C$), 2.77-2.66 (m, 4H, CH$_{2Lev}$), 2.18 (s, 3H, CH$_{3Lev}$), 1.28 (d, 3H, J$_{5,6}$=6.2 Hz, H-6$_D$), 1.20 (d, 3H, J$_{5,6}$=6.2 Hz, H-6$_C$).

$^{13}$C NMR (CDCl$_3$) partial, δ 206.1 (CO$_{Lev}$), 171.7 (CO$_{2Lev}$), 167.3 (C-6$_A$), 159.2 (C$_{IVPMB}$), 113.7 (2C, C$_{ArPMB}$), 102.7 (C-1$_A$, $^1$J$_{CH}$=157.6 Hz), 100.0 (C-1$_D$, $^1J_{CH}$=178.6 Hz), 99.2 (C-1$_C$, $^1J_{CH}$=171.6 Hz), 67.3 (C$_{CO2Bn}$), 55.1 (CH$_{3PMB}$), 38.2 (COCH$_{2Lev}$), 29.8 (CH$_{3Lev}$), 28.3 (CO$_2$CH$_{2Lev}$).

HRMS (ESI$^+$): m/z 1307.5554 (calcd for C$_{76}$H$_{84}$O$_{18}$Na [M+Na]$^+$: m/z 1307.5555).

Benzyl (4-O-benzyl-3-O-para-methoxybenzyl-α-L-rhamnopyranosyl)-(1→2)-(3,4-di-O-benzyl-α-L-rhamnopyranosyl)-(1→4)-(allyl 2,3-di-O-benzyl-β-D-galactopyranosid)uronate (169)

Acetic acid (11.3 mL) followed by hydrazine monohydrate (492 µL, 10.1 mmol) were slowly added to a solution of the fully protected 167 (2.60 g, 2.0 mmol) in dry pyridine (16.8 mL) stirred at 0° C. under an Ar atmosphere. The reaction mixture was stirred at rt for 30 min. Volatiles were evaporated and co-evaporated twice with toluene. The residue was taken up in DCM and washed with water. The aq. layer was re-extracted twice with DCM, and the combined organic phases were washed with brine, passed through a phase separator filter, and concentrated. The residue was purified by flash chromatography (Tol/EtOAc 9:1 to 7:3) to give alcohol 169 (2.23 g, 93%) as a white foam.

$^1$H NMR (CDCl$_3$), δ 7.45-7.16 (m, 32H, H$_{Ar}$), 6.89 (d, 2H, J=8.6 Hz, H$_{ArPMB}$), 6.00 (m, 1H, CH=$_{All}$), 5.37 (m, 1H, J$_{trans}$=17.3 Hz, J$_{gem}$=1.6 Hz, =CH$_{2All}$), 5.35 (bs$_o$, 1H, H-1$_B$), 5.28 (d, 1H, J=12.1 Hz, H$_{CO2Bn}$), 5.23 (m, 1H, J$_{cis}$=10.5 Hz, =CH$_{2All}$), 5.13 (d, 1H, H$_{CO2Bn}$), 5.02 (d, 1H, J$_{1,2}$=1.4 Hz, H-1$_C$), 4.94 (d$_{po}$, 1H, J=10.9 Hz, H$_{Bn}$), 4.90 (d$_{po}$, 1H, J=11.2 Hz, H$_{Bn}$), 4.89 (d$_{po}$, 1H, J=10.9 Hz, H$_{Bn}$), 4.81 (d, 1H, J=12.1 Hz, H$_{Bn}$), 4.75 (d, 1H, 1=10.9 Hz, H$_{Bn}$), 4.70-4.59 (m, 7H, H$_{Bn}$), 4.51 (m, 1H, H$_{All}$), 4.40 (m$_o$, 1H, H-4$_A$), 4.39 (d$_o$, 1H, J$_{1,2}$=7.7 Hz, H-1$_A$), 4.17 (m$_{po}$, 1H, H$_{All}$), 4.15 (m$_o$, 1H, H-2$_D$), 4.12 (m, 1H, H-2$_C$), 4.03 (d, 1H, J$_{4,5}$=0.9 Hz, H-5$_A$), 3.91-3.86 (m, 2H, H-3$_C$, H-3$_D$), 3.84 (dq$_{po}$, 1H, H-5$_A$), 3.79 (s, 3H, CH$_{3PMB}$), 3.76-3.66 (m, 2H, H-2$_A$, H-5$_D$), 3.52 (dd, 1H, J$_{2,3}$=9.8 Hz, J$_{3,4}$=2.8 Hz, H-3$_A$), 3.45 (pt$_{po}$, 1H, J$_{4,5}$=9.5 Hz, H-4$_C$), 3.41 (pt, 1H, J$_{3,4}$=J$_{4,5}$=9.6 Hz, H-4$_D$), 1.30 (d, 3H, J$_{5,6}$=6.2 Hz, H-6$_D$), 1.21 (d, 3H, J$_{5,6}$=6.2 Hz, H-6$_C$).

$^{13}$C NMR (CDCl$_3$) partial, δ 167.3 (C-6$_A$), 159.2 (C$_{IVPMB}$), 114.0 (2C, C$_{ArPMB}$), 102.7 (C-1$_A$, $^1J_{CH}$=161.1 Hz), 100.8 (C-1$_D$, $^1J_{CH}$=169.0 Hz), 100.2 (C-1$_C$, $^1J_{CH}$=171.9 Hz), 67.3 (C$_{CO2Bn}$), 55.2 (CH$_{3PMB}$).

HRMS (ESI$^+$): m/z 1210.5117 (calcd for C$_{71}$H$_{78}$O$_{16}$Na [M+Na]$^+$: m/z 1210.5222), m/z 613.2374 (calcd for C$_{71}$H$_{79}$O$_{16}$K [M+H+K]$^{2+}$: m/z 613.2502).

Benzyl (3,4,6-tri-O-benzyl-2-deoxy-2-trichloroacetamido-β-D-galactopyranosyl)-(1→2)-(4-O-benzyl-3-O-para-methoxybenzyl-α-L-rhamnopyranosyl)-(1→2)-(3,4-di-O-benzyl-α-L-rhamnopyranosyl)-(1→4)-(allyl 2,3-di-O-benzyl-β-D-galactopyranosid)uronate (183)

A mixture of acceptor 169 (300 mg, 253 µmol), thioglycoside donor 24 (260 mg, 379 µmol), and freshly activated 4 powdered MS (750 mg) in anhyd. DCM (2.9 mL) was stirred for 1 h at rt under an Ar atmosphere. The reaction mixture was cooled to −78° C., then NIS (114 mg, 505 µmol) and TMSOTf (4.6 µL, 25 µmol) were added. The reaction mixture was stirred for 30 min allowing the bath to reach −60° C. A TLC control (Tol/EtOAc 9:1) indicated the absence of acceptor 169 (rf=0.18) and the presence of a new less polar product (rf=0.38). The reaction was quenched by addition of Et$_3$N. The resulting suspension was filtered and concentrated. The residue was purified by flash chromatography (Tol/EtOAc 98:2 to 92:8) to give tetrasaccharide 183 (356 mg, 80%) as a white foam.

$^1$H NMR (CDCl$_3$), δ 7.41-7.05 (m, 47H, H$_{Ar}$), 6.91 (d, 1H, J$_{NH,2}$=7.5 Hz, NH), 6.83 (d, 2H, J=8.6 Hz, H$_{ArPMB}$), 5.97 (m, 1H, CH=$_{All}$), 5.35 (m, 1H, J$_{trans}$=17.3 Hz, J$_{gem}$=1.6 Hz, =CH$_{2All}$), 5.26 (bs, 1H, H-1$_D$), 5.25 (d$_{po}$, 1H, H$_{CO2Bn}$), 5.21 (m, 1H, J$_{cis}$=10.5 Hz, =CH$_{2All}$), 5.10 (d, 1H, J=12.2 Hz, H$_{CO2Bn}$) 4.98-4.92 (m, 4H, H-1$_B$, H-1$_C$, 2H$_{Bn}$), 4.90 (d$_{po}$, 1H, J=10.9 Hz, H$_{Bn}$), 4.84 (d$_{po}$, 1H, J=11.1 Hz, H$_{Bn}$), 4.76 (d, 1H, J=12.1 Hz, H$_{Bn}$), 4.72 (d$_{po}$, 1H, J=10.5 Hz, H$_{Bn}$), 4.71-4.67 (m, 2H, H$_{Bn}$), 4.65-4.55 (m, 3H, H$_{Bn}$), 4.58-4.45 (m, 6H, 5H$_{Bn}$, H$_{All}$), 4.36 (d$_o$, 1H, J$_{1,2}$=7.7 Hz, H-1$_A$), 4.34 (bd$_o$, 1H, H-4$_A$), 4.27 (d, 1H, J=11.6 Hz, H$_{Bn}$), 4.22 (d, 1H, J=11.6 Hz, H$_{Bn}$), 4.18-4.10 (m, 2H, H-2$_B$, H$_{All}$), 4.08 (pt, 1H, H-2$_C$), 4.03-3.96 (m, 4H, H-5$_A$, H-3$_B$, H-4$_B$, H-2$_D$), 3.87 (dd, 1H, J$_{2,3}$=3.0 Hz, J$_{3,4}$=9.6 Hz, H-3$_C$), 3.81 (dd$_{po}$, 1H, J$_{2,3}$=3.0 Hz, J$_{3,4}$=9.5 Hz, H-3$_D$), 3.79 (dq$_{po}$, 1H, H-5$_C$), 3.71 (s, 3H, CH$_{3PMB}$), 3.70-3.59 (m, 3H, H-2$_A$, H-6a$_B$, H-5$_D$), 3.51-3.42 (m, 3H, H-3$_A$, H-5$_B$, H-4$_C$), 3.34 (pt$_{po}$, 1H, J$_{4,5}$=9.2 Hz, H-4$_D$), 3.31 (m$_o$, 1H, H-6b$_B$), 1.28 (d, 3H, J$_{5,6}$=6.2 Hz, H-6$_D$), 1.18 (d, 3H, J$_{5,6}$=6.2 Hz, H-6$_C$).

$^{13}$C NMR (CDCl$_3$) partial, δ 167.3 (C-6$_A$), 161.6 (NHCO), 159.4 (C$_{IVPMB}$), 113.9 (2C, C$_{ArPMB}$), 102.7 (C-1$_A$, $^1J_{CH}$=162.0 Hz), 101.3 (C-1$_C$, $^1J_{CH}$=173.5 Hz), 100.7 (C-1$_B$, $^1J_{CH}$=162.4 Hz), 100.4 (C-1$_D$, $^1J_{CH}$=175.4 Hz), 92.9 (CCl$_3$), 67.3 (C$_{CO2Bn}$), 55.2 (CH$_{3PMB}$).

HRMS (ESI$^+$): m/z 1784.6198 (calcd for C$_{100}$H$_{106}$Cl$_3$NO$_{21}$Na [M+Na]$^+$: m/z 1784.6221).

Benzyl (3,4,6-tri-O-benzyl-2-deoxy-2-trichloroacetamido-β-D-galactopyranosyl)-(1→2)-(3-O-acetyl-4-O-benzyl-α-L-rhamnopyranosyl)-(1→2)-(3,4-di-O-benzyl-α-L-rhamnopyranosyl)-(1→4)-(allyl 2,3-di-O-benzyl-β-D-galactopyranosid)uronate (187)

Water (1.6 mL) and CAN (870 mg, 1.59 mmol) were added to a solution of tetrasaccharide 183 (700 mg, 397 µmol) in MeCN (15.9 mL). The reaction mixture was stirred at rt for 30 min. The reaction was quenched with satd. aq. NaHCO$_3$. The reaction mixture was diluted with water and DCM and the aq. phase was extracted three times with DCM. The combined extracts were washed with brine, passed through a phase separator filter, and concentrated. The resulting crude oil was dissolved in pyridine (20 mL), and excess acetic anhydride (3.75 mL) and DMAP (48 mg, 397 µmol) were added to the solution kept under stirring at rt. Volatiles were evaporated and co-evaporated three times with toluene. The residue was purified by flash chromatography (Tol/EtOAc 95:5 to 9:1) to afford the monoacetylated tetrasaccharide 187 (582 mg, 87% over two steps) as a white foam.

$^1$H NMR (CDCl$_3$), δ 7.41-7.04 (m, 45H, H$_{Ar}$), 7.02 (d, 1H, J$_{NH,2}$=7.0 Hz, NH), 5.98 (m, 1H, CH=$_{All}$), 5.36 (dd$_{po}$, 1H, J$_{2,3}$=3.1 Hz, H-3$_C$), 5.35 (m, 1H, J$_{gem}$=1.6 Hz, =CH$_{2All}$), 5.32 (d, 1H, J$_{1,2}$=1.6 Hz, H-1$_D$), 5.26 (d, 1H, J=12.2 Hz H$_{CO2Bn}$), 5.22 (m, 1H, J$_{cis}$ 10.5 Hz, =CH$_{2All}$), 5.09 (d, 1H, H$_{CO2Bn}$), 5.03 (d$_{po}$, 1H, J$_{1,2}$=8.4 Hz, H-1$_B$), 5.01 (d$_{po}$, 1H, J$_{1,2}$=2.0 Hz, H-1$_C$), 4.89 (d$_{po}$, 1H, J 10.8 Hz, H$_{Bn}$), 4.88 (d, 2H, J=11.1 Hz, 2H$_{Bn}$), 4.77 (d, 1H, J=11.8 Hz, H$_{Bn}$), 4.70 (d, 2H, J=11.2 Hz, H$_{Bn}$), 4.66 (d, 1H, J=11.2 Hz, H$_{Bn}$), 4.62-4.52 (m$_{po}$, 7H, H$_{Bn}$), 4.50 (m$_{po}$, 1H, H$_{All}$), 4.40-4.35 (m, 4H, H-1$_A$, H-4$_A$, H-3$_B$, H-2$_C$), 4.26 (d, 1H, J=11.6 Hz, H$_{Bn}$), 4.20 (d, 1H, J=11.6 Hz, H$_{Bn}$), 4.16 (m, 1H, H$_{All}$), 4.05 (d, 1H, J$_{3,4}$=2.4 Hz, H-4$_B$), 4.01 (d, 1H, J$_{4,5}$=0.9 Hz, H-5$_A$), 4.00 (m, 1H, H-2$_D$), 3.92-3.82 (m, 2H, H-2$_B$, H-5$_C$), 3.80 (dd, 1H, J$_{2,3}$=2.9 Hz, J$_{3,4}$=9.5 Hz, H-3$_D$), 3.70-3.58 (m, 3H, H-2$_A$, H-6a$_B$, H-5$_D$), 3.56-3.47 (m, 4H, H-3$_A$, H-5$_B$, H-4$_C$, H-4$_D$), 3.35 (dd, 1H, J$_{5,6b}$=4.5 Hz, J$_{6a,6b}$=8.3 Hz, H-6b$_B$), 2.17 (s, 3H, H$_{Ac}$), 1.29 (d, 3H, J$_{5,6}$=6.2 Hz, H-6$_D$), 1.14 (d, 3H, J$_{5,6}$=6.2 Hz, H-6$_C$).

$^{13}$C NMR (CDCl$_3$) partial, δ 170.7 (CO$_{Ac}$) 167.2 (C-6$_A$), 161.5 (NHCO), 102.6 (C-1$_A$, $^1$J$_{CH}$=156.6 Hz), 101.3 (C-1$_C$, $^1$J$_{CH}$=176.3 Hz), 100.0 (C-1$_D$, $^1$J$_{CH}$=171.1 Hz), 99.6 (C-1$_B$, $^1$J$_{CH}$=163.3 Hz), 92.9 (CCl$_3$), 67.3 (C$_{CO2Bn}$), 21.3 (CH$_{3Ac}$).

HRMS (ESI$^+$): m/z 1684.5983 (calcd for C$_{94}$H$_{101}$Cl$_3$NO$_{21}$ [M+H]$^+$: m/z 1684.5931), m/z 1706.5928 (calcd for C$_{94}$H$_{100}$Cl$_3$NO$_{21}$Na [M+Na]$^+$: m/z 1706.5751).

Propyl 2-acetamido-2-deoxy-β-D-galactopyranosyl-(1→2)-α-L-rhamnopyranosyl-(1→2)-α-L-rhamnopyranosyl-(1→4)-β-D-galactopyranosiduronic acid (XXX)

To a stirred solution of tetrasaccharide 183 (254 mg, 140 μmol) in THF/H$_2$O (4:1, 10.2 mL), was added 10% Pd/C (200 mg). The suspension was stirred under a hydrogen atmosphere for 2 days. After this time, MS analysis indicated a single molecular weight corresponding to that of the target tetrasaccharide. The reaction mixture was filtered. Evaporation of the volatiles, freeze-drying furnished and purification of the crude material by preparative RP-HPLC (Kromasil 5 μm C18 100 Å 10×250 mm semi-preparative column, 0-20% linear gradient of CH$_3$CN in 0.08% aq. TFA over 20 min at a flow rate of 5.5 mL·min$^{-1}$) gave tetrasaccharide XXX (61.8 mg, 59%) as a white solid following repeated freeze-drying.

$^1$H NMR (D$_2$O), δ 5.24 (d, 1H, J$_{1,2}$=1.4 Hz, H-1$_D$), 5.08 (d, 1H, J$_{1,2}$=1.5 Hz, H-1$_C$), 4.55 (d, 1H, J$_{1,2}$=8.4 Hz, H-1$_B$), 4.38 (d, 1H, J$_{1,2}$=8.0 Hz, H-1$_A$), 4.35 (d, 1H, J$_{4,5}$=1.2 Hz, H-5$_A$), 4.27 (dd, 1H, J$_{3,4}$=2.8 Hz, H-4$_A$), 4.05 (dd, 1H, 1$_{2,3}$=3.0 Hz, H-2$_C$), 4.02 (dd, 1H, J$_{2,3}$=3.1 Hz, H-2$_D$), 3.87-3.74 (m, 6H, H-4$_B$, OCH$_{2Pr}$, H-2$_B$, H-3$_A$, H-3$_D$, H-3$_C$), 3.74-3.63 (m, 3H, H-6a$_B$, H-6b$_B$, H-3$_B$), 3.63-3.51 (m, 4H, H-5$_B$, H-5$_C$, OCH$_{2Pr}$, H-5$_D$), 3.50 (dd, 1H, J$_{2,3}$=9.9 Hz, H-2$_A$), 3.34 (pt, 1H, J$_{3,4}$=J$_{4,5}$=9.8 Hz, H-4$_D$), 3.27 (pt, 1H, J$_{3,4}$=J$_{4,5}$=9.7 Hz, H-4$_C$), 1.97 (s, 3H, CH$_{3NHAc}$), 1.57 (sex, 2H, J=7.4 Hz, CH$_{2Pr}$), 1.20-1.15 (m, 6H, H-6$_C$, H-6$_D$), 0.84 (t, 3H, CH$_{3Pr}$)

$^{13}$C NMR (D$_2$O), δ 175.1 (NHCO), 171.6 (C-6$_A$), 103.1 (C-1$_B$, $^1$J$_{CH}$=163.2 Hz), 102.3 (C-1$_A$, $^1$J$_{CH}$=161.7 Hz), 101.0 (C-1$_C$, J$_{CH}$=175.8 Hz), 99.9 (C-1$_D$, $^1$J$_{CH}$=174.7 Hz), 78.6 (C-2$_C$), 78.5 (C-2$_D$), 76.7 (C-4$_A$), 75.0 (C-5$_B$), 72.9 (C-3$_A$), 72.8 (C-5$_A$), 72.3 (2C, C-4$_C$, OCH$_{2Pr}$), 71.9 (C-4$_D$), 70.8 (C-3$_B$), 70.2 (C-2$_A$), 69.7 (2C, C-3$_D$, C-3$_C$), 69.2 (C-5$_D$), 69.1 (C-5$_C$), 67.7 (C-4$_B$), 60.9 (C-6$_B$), 52.8 (C-2$_B$), 22.0 (2C, CH$_{2Pr}$, CH$_{3NHAc}$), 16.6 (2C, C-6$_D$, C-6$_C$), 9.6 (CH$_{3Pr}$).

HRMS (ESI$^+$): m/z 754.2722 (calcd for C$_{29}$H$_{49}$NO$_{20}$Na [M+Na]$^+$: m/z 754.2745). RP-HPLC (215 nm): R$_t$=8.5 min.

Propyl 2-acetamido-2-deoxy-β-D-galactopyranosyl-(1→2)-(3-O-acetyl-α-L-rhamnopyranosyl)-(1→2)-α-L-rhamnopyranosyl-(1→4)-β-D-galactopyranosiduronic acid (XXXI)

To a stirred solution of tetrasaccharide 187 (187 mg, 110 μmol) in THF/H$_2$O (4:1, 8.4 mL), was added 10% Pd/C (150 mg). The suspension was stirred under a hydrogen atmosphere for 2 days. After this time, MS analysis indicated a molecular weight corresponding to that of the target tetrasaccharide. The reaction mixture was filtered. Evaporation of the volatiles, freeze-drying and purification by preparative RP-HPLC (Kromasil 5 μm C18 100 Å 10×250 mm semi-preparative column, 0-20% linear gradient of CH$_3$CN in 0.08% aq. TFA over 20 min at a flow rate of 5.5 mL·min$^{-1}$) gave tetrasaccharide XXXI (45.3 mg, 53%) as a white solid following repeated freeze-drying.

$^1$H NMR (D$_2$O), δ 5.23 (d, 1H, J$_{1,2}$=1.3 Hz, H-1$_D$), 5.03 (d, 1H, J$_{1,2}$=1.7 Hz, H-1$_C$), 4.92 (dd, 1H, J$_{2,3}$=3.0 Hz, J$_{3,4}$=10.0 Hz, H-3$_C$), 4.33 (d, 1H, J$_{1,2}$=8.0 Hz, H-1$_A$), 4.31 (bs$_o$, 1H, H-5$_A$), 4.30 (d$_{po}$, 1H, J$_{1,2}$=8.3 Hz, H-1$_B$), 4.22 (dd, 1H, J$_{3,4}$=2.8 Hz, J$_{4,5}$=1.1 Hz, H-4$_A$), 4.12 (pt, 1H, H-2$_C$), 3.99 (dd, 1H, J$_{2,3}$=3.1 Hz, H-2$_D$), 3.83-3.70 (m, 5H, H-4$_B$, OCH$_{2Pr}$, H-2$_B$, H-3$_A$, H-3$_D$), 3.70-3.57 (m, 4H, H-5$_C$, H-6a$_B$, H-6b$_B$, H-3$_B$), 3.52-3.46 (m, 3H, H-5$_B$, OCH$_{2Pr}$, H-5$_D$), 3.45 (dd$_{po}$, 1H, J$_{2,3}$=10.0 Hz, H-2$_A$), 3.34 (pt$_{po}$, 1H, J=9.3 Hz, J=9.8 Hz, H-4$_C$), 3.35 (pt$_{po}$, 1H, J=9.6 Hz, J=9.8 Hz, H-4$_D$), 2.09 (s, 3H, CH$_{3Ac}$), 1.97 (s, 3H, CH$_{3NHAc}$), 1.56 (sex, 2H, J=7.4 Hz, CH$_{2Pr}$), 1.16 (d, 3H, J$_{5,6}$=6.3 Hz, H-6$_D$), 1.14 (d, 3H, J$_{5,6}$=6.2 Hz, H-6$_C$), 0.80 (t, 3H, CH$_{3Pr}$) $^{13}$C NMR (D$_2$O), δ 174.5 (NHCO), 173.5 (CO$_{Ac}$), 171.5 (C-6$_A$), 103.2 (C-1$_B$, $^1$J$_{CH}$=163.2 Hz), 102.3 (C-1$_A$, $^1$J$_{CH}$=161.8 Hz), 101.0 (C-1$_C$, $^1$J$_{CH}$=174.7 Hz), 99.8 (C-1$_D$, $^1$J$_{CH}$=173.6 Hz), 78.8 (C-2$_D$), 76.7 (C-4$_A$), 76.4 (C-2$_C$), 74.8 (C-5$_B$), 72.8 (C-3$_A$), 72.7 (C-5$_A$), 72.6 (C-3$_C$), 72.2 (OCH$_{2Pr}$), 71.8 (C-4$_D$), 70.2 (C-3$_B$), 70.1 (C-2$_A$), 70.0 (C-4$_C$), 69.6 (C-3$_D$), 69.2 (C-5$_D$), 69.1 (C-5$_C$), 67.6 (C-4$_B$), 60.8 (C-6$_B$), 52.4 (C-2$_B$), 22.3 (CH$_{3NHAc}$), 22.1 (CH$_{2Pr}$), 20.5 (CH$_{3Ac}$), 16.6, 16.5 (2C, C-6$_D$, C-6$_C$), 9.6 (CH$_{3Pr}$)

HRMS (ESI$^+$): m/z 796.2866 (calcd for C$_{31}$H$_{51}$NO$_{21}$Na [M+Na]$^+$: m/z 796.2852).

HPLC (215 nm): R$_t$=9.0 min.

Characterization of Additional Propyl Tetrasaccharides Mimicking Frame-Shifted Repeating Units of SF6, SF6a and/or E. coli O147 O—Ags, Obtained According to a Linear Synthetic Strategy.

Propyl β-D-galactopyranosyluronic acid-(1→3)-2-acetamido-2-deoxy-β-D-galactopyranosyl-(1→2)-α-L-rhamnopyranosyl-(1→2)-α-L-rhamnopyranoside (XIX)

$^1$H NMR (D$_2$O), δ 5.01 (d, 1H, J$_{1,2}$=1.4 Hz, H-1$_C$), 4.76 (d, 1H, J$_{1,2}$=1.2 Hz, H-1$_D$), 4.55 (d, 1H, J$_{1,2}$=8.4 Hz, H-1$_B$), 4.36 (d, 1H, J$_{1,2}$=7.8 Hz, H-1$_A$), 4.23 (d, 1H, J$_{4,5}$=1.2 Hz, H-5$_A$), 4.12 (dd, 1H, J$_{3,4}$=3.4 Hz, H-4$_A$), 4.09 (d, 1H, J$_{3,4}$=3.1 Hz, H-4$_B$), 4.02 (dd, 1H, J$_{2,3}$=2.8 Hz, H-2$_C$), 3.89 (dd, 1H, J$_{2,3}$=10.9 Hz, H-2$_B$), 3.79 (dd, 1H, J$_{2,3}$=3.4 Hz, H-2$_D$), 3.77-3.69 (m, 3H, H-3$_B$, H-3$_C$, H-3$_D$), 3.66 (dd, 1H, J$_{5,6a}$=7.8 Hz, J$_{6a,6b}$=11.9 Hz, H-6a$_B$), 3.64-3.53 (m, 5H, H-6b$_B$, H-5$_C$, H-3$_A$, H-5$_B$, H-5$_D$), 3.51 (dt$_{po}$, 1H, J=7.0 Hz, J=9.8 Hz, OCH$_{2Pr}$), 3.41 (dd$_{po}$, 1H, J$_{2,3}$=9.9 Hz, H-2$_A$), 3.36 (dt$_{po}$, 1H, J=6.3 Hz, OCH$_{2Pr}$), 3.31 (pt$_{po}$, 1H, J$_{3,4}$=J$_{4,5}$=9.6 Hz, H-4$_D$), 3.22 (pt, 1H, J$_{3,4}$=J$_{4,5}$=9.7 Hz, H-4$_C$), 1.89 (s, 3H, CH$_{3NHAc}$), 1.47 (psex, 2H, CH$_{2Pr}$), 1.15 (d, 3H, J$_{5,6}$=6.2 Hz, H-6$_D$), 1.12 (d, 3H, J$_{5,6}$=6.2 Hz, H-6$_C$), 0.78 (t, 3H, J=7.4 Hz, CH$_{3Pr}$)

$^{13}$C NMR (D$_2$O), δ 174.9 (NHCO), 172.0 (C-6$_A$), 104.6 (C-1$_A$, $^1$J$_{CH}$=162.3 Hz), 102.7 (C-1$_B$, $^1$J$_{CH}$=163.4 Hz), 101.1 (C-1$_C$, $^1$J$_{CH}$=173.5 Hz), 98.1 (C-1$_D$, $^1$J$_{CH}$=171.8 Hz), 79.9 (C-3$_B$), 78.9 (C-2$_D$), 78.4 (C-2$_C$), 74.6 (C-5$_B$), 73.7 (C-5$_A$), 72.1 (C-4$_C$), 72.0 (C-4$_D$), 71.9 (C-3$_A$), 69.9 (C-3$_D$), 69.8 (C-2$_A$), 69.7 (OCH$_{2Pr}$), 69.6 (C-4$_A$), 69.4 (C-3$_C$), 69.1 (C-5$_C$), 68.6 (C-5$_D$), 67.6 (C-4$_B$), 60.9 (C-6$_B$), 51.5 (C-2$_B$), 22.3 (CH$_{3NHAc}$), 21.8 (CH$_{2Pr}$), 16.5 (2C, C-6$_D$, C-6$_C$), 9.7 (CH$_{3Pr}$).

HRMS (ESI$^+$): m/z 754.2789 (calcd for C$_{29}$H$_{49}$NO$_{20}$Na [M+Na]$^+$: m/z 754.2745).

HPLC (215 nm): R$_t$=12.5 min.

Propyl β-D-galactopyranosyluronic acid-(1→3)-2-acetamido-2-deoxy-β-D-galactopyranosyl-(1→2)-3-O-acetyl-α-L-rhamnopyranosyl-(1→2)-α-L-rhamnopyranoside (XII)

$^1$H NMR (D$_2$O), δ 5.03 (d, 1H, J$_{1,2}$=1.7 Hz, H-1$_C$), 4.93 (dd, 1H, J$_{2,3}$=3.0 Hz, J$_{3,4}$=10.0 Hz, H-3$_C$), 4.80 (d, 1H, J$_{1,2}$=1.1 Hz, H-1$_D$), 4.40 (d$_{po}$, 1H, J$_{1,2}$=7.7 Hz, H-1$_A$), 4.39 (d$_{po}$, 1H, J$_{1,2}$=8.2 Hz, H-1$_B$), 4.23 (d, 1H, J$_{4,5}$=1.2 Hz, H-5$_A$), 4.15 (pt, 1H, H-2$_C$), 4.13 (dd, 1H, J$_{3,4}$=3.4 Hz, H-4$_A$), 4.11 (d, 1H, J$_{3,4}$=2.9 Hz, H-4$_B$), 3.87 (dd$_{po}$, 1H, J$_{2,3}$=10.9 Hz, H-2$_B$), 3.83 (dd, 1H, J$_{2,3}$=3.3 Hz, H-2$_D$), 3.79 (dd, 1H, H-3$_B$), 3.75-3.68 (m, 2H, H-3$_D$, H-5$_C$), 3.68-3.56 (m, 4H, H-6a$_B$, H-6b$_B$, H-3$_A$, H-5$_D$), 3.56-3.47 (m, 2H, H-5$_B$, OCH$_{2Pr}$), 3.46-3.38 (m, 3H, H-2$_A$, H-4$_D$, H-4$_C$), 3.37 (dt$_{po}$, 1H, J=6.4 Hz, J=9.9 Hz, OCH$_{2Pr}$), 2.07 (s, 3H, CH$_{3Ac}$), 1.95 (s, 3H, CH$_{3NHAc}$), 1.48 (psex, 2H, CH$_{2Pr}$), 1.17 (d, 3H, J$_{5,6}$=6.2 Hz, H-6$_D$*), 1.16 (d, 3H, J$_{5,6}$=6.2 Hz, H-6$_C$*), 0.79 (t, 3H, J=7.4 Hz, CH$_{3Pr}$)

$^{13}$C NMR (D$_2$O), δ 174.7 (NHCO), 173.6 (CO$_{Ac}$), 172.2 (C-6$_A$), 104.6 (C-1$_A$, $^1$J$_{CH}$=162.1 Hz), 102.7 (C-1$_B$, $^1$J$_{CH}$=163.9 Hz), 101.1 (C-1$_C$, $^1$J$_{CH}$=176.5 Hz), 98.0 (C-1$_D$, $^1$J$_{CH}$=171.9 Hz), 79.4 (C-2$_D$), 79.1 (C-3$_B$), 76.3 (C-2$_C$), 74.5 (C-5$_B$), 73.9 (C-5$_A$), 72.6 (C-3$_C$), 72.0, 71.9 (2C, C-3$_A$, C-4$_D$), 69.9-69.8 (3C, C-4$_C$, C-2$_A$, C-3$_D$), 69.7 (OCH$_{2Pr}$), 69.5 (C-4$_A$), 69.2 (C-5$_C$), 68.6 (C-5$_D$), 67.4 (C-4$_B$), 60.8 (C-6$_B$), 51.4 (C-2$_B$), 22.3 (CH$_{3NHAc}$), 21.8 (CH$_{2Pr}$), 20.5 (CH$_{3Ac}$), 16.5 (2C, C-6$_D$, C-6$_C$), 9.7 (CH$_{3Pr}$).

HRMS (ESI$^+$): m/z 796.2831 (calcd for C$_{31}$H$_{51}$NO$_{21}$Na [M+Na]$^+$: m/z 796.2852).

HPLC (215 nm): R$_t$=13.5 min

Propyl β-D-galactopyranosyl uronic acid-(1→3)-2-acetamido-2-deoxy-β-D-galactopyranosyl-(1→2)-4-O-acetyl-α-L-rhamnopyranosyl-(1→2)-α-L-rhamnopyranoside (XII')

$^1$H NMR (D$_2$O), δ 5.06 (d, 1H, 1$_{1,2}$=1.6 Hz, H-1$_C$), 4.80 (d, 1H, J$_{1,2}$=1.1 Hz, H-1$_D$), 4.73 (pt, 1H, J$_{4,5}$=9.8 Hz, H-4$_C$), 4.63 (d, 1H, J$_{1,2}$=8.4 Hz, H-1$_B$), 4.39 (d, 1H, J$_{1,2}$=7.8 Hz, H-1$_A$), 4.20 (d, 1H, 1$_{4,5}$=1.1 Hz, H-5$_A$), 4.16-4.13 (m, 3H, H-2$_C$, H-4$_A$, H-4$_B$), 4.00 (dd, 1H, J$_{2,3}$=3.0 Hz, J$_{3,4}$=9.9 Hz, H-3$_C$), 3.94 (dd, 1H, J$_{2,3}$=10.9 Hz, H-2$_B$), 3.86 (dd, 1H, 1$_{2,3}$=3.3 Hz, H-2$_D$), 3.84-3.74 (m, 3H, H-3$_B$, H-3$_D$, H-5$_C$), 3.72 (dd$_{po}$, 1H, J$_{5,6a}$=7.7 Hz, J$_{6a,6b}$=12.0 Hz, H-6a$_B$), 3.67 (dd$_{po}$, 1H, 1$_{5,6b}$=4.7 Hz, H-6b$_B$), 3.64-3.56 (m, 3H, H-3$_A$, H-5$_D$, H-5$_B$), 3.55 (pt$_{po}$, 1H, J=6.9 Hz, J=9.8 Hz, OCH$_{2Pr}$), 3.46 (dd, 1H, J$_{2,3}$=10.0 Hz, H-2$_A$), 3.40 (dt, 1H, J=6.3 Hz, OCH$_{2Pr}$), 3.36 (pt, 1H, J$_{3,4}$=J$_{4,5}$=9.7 Hz, H-4$_D$), 2.06 (s, 3H, CH$_{3Ac}$), 1.93 (s, 3H, CH$_{3NHAc}$), 1.51 (psex, 2H, CH$_{2Pr}$), 1.20 (d, 3H, J$_{5,6}$=6.2 Hz, H-6$_D$), 1.06 (d, 3H, J$_{5,6}$=6.2 Hz, H-6$_C$), 0.82 (t, 3H, J=7.4 Hz, CH$_{3Pr}$).

$^{13}$C NMR (D$_2$O), δ 175.0 (NHCO), 173.7 (CO$_{Ac}$), 172.6 (C-6$_A$), 104.3 (C-1$_A$, $^1$J$_{CH}$=162.6 Hz), 102.4 (C-1$_B$, $^1$J$_{CH}$=164.1 Hz), 101.1 (C-1$_C$, $^1$J$_{CH}$=175.0 Hz), 98.1 (C-1$_D$, $^1$J$_{CH}$=171.4 Hz), 79.9 (C-3$_B$), 79.1 (C-2$_D$), 77.6 (C-2$_C$), 74.8 (C-5$_B$), 74.1 (2C, C-5$_A$, C-4$_C$), 72.2 (C-4$_D$), 72.1 (C-3$_A$), 70.0 (2C, C-2$_A$, C-3$_D$), 69.8 (OCH$_{2Pr}$), 69.7 (C-4$_A$), 68.6 (C-5$_D$), 68.1 (C-3$_C$), 67.7 (C-4$_B$), 67.1 (C-5$_C$), 61.0 (C-6$_B$), 51.6 (C-2$_B$), 22.3 (CH$_{3NHAc}$), 21.9 (CH$_{2Pr}$), 20.5 (CH$_{3Ac}$), 16.6, 16.5 (2C, C-6$_D$, C-6$_C$), 9.8 (CH$_{3Pr}$).

HRMS (ESI$^+$): m/z 796.2927 (calcd for C$_{31}$H$_{51}$NO$_{21}$Na [M+Na]$^+$: m/z 786.2852).

HPLC (215 nm): R$_t$=17.3 min.

Propyl α-L-rhamnopyranosyl-(1→4)-β-D-galactopyranosyluronic acid-(1→3)-2-acetamido-2-deoxy-β-D-galactopyranosyl-(1→2)-α-L-rhamnopyranoside (XVI)

$^1$H NMR (D$_2$O), δ 5.09 (d, 1H, J$_{1,2}$=1.6 Hz, H-1$_D$), 4.90 (d, 1H, J$_{1,2}$=1.5 Hz, H-1$_C$), 4.63 (d, 1H, J$_{1,2}$=8.4 Hz, H-1$_B$), 4.44 (d, 1H, J$_{1,2}$=7.7 Hz, H-1$_A$), 4.33 (d, 1H, J$_{4,5}$=1.1 Hz, H-5$_A$), 4.29 (dd, 1H, 1$_{3,4}$=3.1 Hz, H-4$_A$), 4.15 (d, 1H, J$_{3,4}$=3.1 Hz, H-4$_B$), 4.01 (dd, 1H, J$_{2,3}$=3.4 Hz, H-2$_D$), 3.96 (dd$_{po}$, 1H, J$_{2,3}$=10.8 Hz, H-2$_B$), 3.94 (dd$_o$, 1H, H-2$_C$), 3.83-3.73 (m, 3H, H-3$_A$, H-3$_B$, H-3$_C$), 3.73-3.67 (m, 3H, H-6a$_B$, H-6b$_B$, H-3$_D$), 3.64-3.49 (m, 5H, H-5$_C$, H-5$_B$, OCH$_{2Pr}$, H-5$_D$, H-2$_A$), 3.42 (dt, J=6.2 Hz, J=9.8 Hz, OCH$_{2Pr}$), 3.33 (pt, 1H, J$_{3,4}$=J$_{4,5}$=9.8 Hz, H-4$_D$), 3.27 (pt, 1H, J$_{3,4}$=J$_{4,5}$=9.6 Hz, H-4$_C$), 1.96 (s, 3H, CH$_{3NHAc}$), 1.53 (sex, 2H, CH$_{2Pr}$), 1.20 (d, 3H, J$_{5,6}$=6.2 Hz, H-6$_C$), 1.17 (d, 3H, J$_{5,6}$=6.2 Hz, H-6$_D$), 0.83 (t, 3H, J=7.5 Hz, CH$_{3Pr}$).

$^{13}$C NMR (D$_2$O), δ 175.0 (NHCO), 171.6 (C-6$_A$), 104.5 (C-1$_A$, $^1$J$_{CH}$=163.1 Hz), 102.7 (C-1$_B$, $^1$J$_{CH}$=163.5 Hz), 101.5 (C-1$_D$, $^1$J$_{CH}$=174.2 Hz), 98.5 (C-1$_C$, $^1$J$_{CH}$=174.6 Hz), 80.3 (C-3$_B$), 78.5 (C-2$_C$), 76.3 (C-4$_A$), 74.7 (C-5$_B$), 72.9 (C-5$_A$), 72.7 (C-3$_A$), 70.0 (C-4$_C$), 71.7 (C-4$_D$), 72.3 (C-2$_D$), 70.1 (C-3$_C$), 69.6 (C-3$_D$), 69.8 (C-2$_A$), 69.7 (OCH$_{2Pr}$), 69.2 (C-5$_D$), 68.6 (C-5$_C$), 67.7 (C-4$_B$), 60.9 (C-6$_B$), 51.6 (C-2$_B$), 22.4 (CH$_{3NHAc}$), 21.9 (CH$_{2Pr}$), 16.6, 16.5 (2C, C-6$_D$, C-6$_C$), 9.8 (CH$_{3Pr}$)

HRMS (ESI$^+$): m/z 754.2788 (calcd for C$_{29}$H$_{49}$NO$_{20}$Na [M+Na]$^+$: m/z 754.2745).

HPLC (215 nm): R$_t$=10.5 min.

Propyl α-L-rhamnopyranosyl-(1→4)-β-D-galactopyranosyluronic acid-(1→3)-2-acetamido-2-deoxy-β-D-galactopyranosyl-(1→2)-3-O-acetyl-α-L-rhamnopyranoside (XV)

$^1$H NMR (D$_2$O), δ 5.03 (d, 1H, J$_{1,2}$=1.5 Hz, H-1$_D$), 4.93 (dd, 1H, J$_{2,3}$=3.0 Hz, J$_{3,4}$ 10.0 Hz, H-3$_C$), 4.84 (d, 1H, J$_{1,2}$=1.7 Hz, H-1$_C$), 4.42 (d, 1H, J$_{1,2}$=7.8 Hz, H-1$_A$), 4.38 (d, 1H, J$_{1,2}$=8.2 Hz, H-1$_B$), 4.28 (d, 1H, J$_{4,5}$=1.1 Hz, H-5$_A$), 4.23 (dd, 1H, J$_{3,4}$=2.8 Hz, H-4$_A$), 4.10 (d, 1H, J$_{3,4}$=2.9 Hz, H-4$_B$), 4.00 (dd, 1H, H-2$_C$), 3.96 (dd, 1H, J$_{-2,3}$=3.3 Hz, H-2$_D$), 3.88 (dd, 1H, J$_{2,3}$=10.8 Hz, H-2$_B$), 3.78 (dd, 1H, H-3$_B$), 3.73 (dd, 1H, J$_{2,3}$=10.0 Hz, H-3$_A$), 3.69-3.59 (m, 4H, H-6a$_B$, H-6b$_B$, H-3$_D$, OCH$_{2Pr}$), 3.58-3.43 (m, 4H, H-5$_C$, H-5$_B$, H-5$_D$, H-2$_A$), 3.43-3.35 (m, 2H, OCH$_{2Pr}$, H-4$_C$), 3.27 (pt, 1H, J$_{3,4}$=J$_{4,5}$=9.7 Hz, H-4$_D$), 2.06 (s, 3H, CH$_{3Ac}$), 1.94 (s, 3H, CH$_{3NHAc}$), 1.48 (sex, 2H, CH$_{2Pr}$), 1.17 (d, 3H, J$_{5,6}$=6.2 Hz, H-6$_C$), 1.11 (d, 3H, J$_{5,6}$=6.2 Hz, H-6$_D$), 0.78 (t, 3H, J=7.5 Hz, CH$_{3Pr}$).

$^{13}$C NMR (D$_2$O), δ 174.5 (NHCO), 173.4 (CO$_{Ac}$), 171.6 (C-6$_A$), 104.3 (C-1$_A$, $^1$J$_{CH}$=163.6 Hz), 102.6 (C-1$_B$, $^1$J$_{CH}$=165.7 Hz), 101.4 (C-1$_D$, $^1$J$_{CH}$=174.6 Hz), 98.5 (C-1$_C$, $^1$J$_{CH}$=175.3 Hz), 79.8 (C-3$_B$), 76.4 (C-2$_C$), 76.3 (C-4$_A$), 74.4 (C-5$_B$), 72.8 (2C, C-3$_A$, C-3$_C$), 72.6 (C-5$_A$), 71.7 (C-4$_D$), 70.2 (2C, C-4$_C$, C-2$_D$), 69.8 (C-2$_A$), 69.7 (C-3$_D$), 69.6 (OCH$_{2Pr}$), 69.1 (C-5$_D$), 68.6 (C-5$_C$), 67.5 (C-4$_B$), 60.8 (C-6$_B$), 51.4 (C-2$_B$), 22.5 (CH$_{3NHAc}$), 21.9 (CH$_{2Pr}$), 20.5 (CH$_{3Ac}$), 16.5 (2C, C-6$_D$, C-6$_C$), 9.7 (CH$_{3Pr}$).

HRMS (ESI$^+$): m/z 796.5854 (calcd for C$_{31}$H$_{51}$NO$_{21}$Na [M+Na]$^+$: m/z 796.2852).

HPLC (215 nm): R$_t$=12.7 min.

Propyl α-L-rhamnopyranosyl-(1→4)-β-D-galactopyranosyluronic acid-(1→3)-2-acetamido-2-deoxy-β-D-galactopyranosyl-(1→2)-4-O-acetyl-α-L-rhamnopyranoside (XV')

$^1$H NMR (D$_2$O), δ 5.09 (d, 1H, J$_{1,2}$=1.6 Hz, H-1$_D$), 4.90 (d, 1H, J$_{1,2}$=1.6 Hz, H-1$_C$), 4.73 (pt, 1H, J$_{3,4}$=J$_{3,4}$=9.8 Hz,

H-4$_C$), 4.66 (d, 1H, J$_{1,2}$=8.4 Hz, H-1$_B$), 4.44 (d, 1H, J$_{1,2}$=7.8 Hz, H-1$_A$), 4.30 (d, 1H, J$_{4,5}$=1.2 Hz, H-5$_A$), 4.28 (dd, 1H, J$_{3,4}$=2.9 Hz, H-4$_A$), 4.16 (d, 1H, J$_{3,4}$=3.1 Hz, H-4$_B$), 4.04-4.00 (m, 2H, H-2$_C$, H-2$_D$), 4.00-3.94 (m, 2H, H-3$_C$, H-2$_B$), 3.83-3.67 (m, 6H, H-3$_B$, H-3$_A$, H-6a$_B$, H-6b$_B$, H-3$_D$, H-5$_C$), 3.62-3.50 (m, 4H, OCH$_{2Pr}$, H-5$_B$, H-5$_D$, H-2$_A$), 3.43 (dt, 1H, J=6.4 Hz, J=9.7 Hz, OCH$_{2Pr}$), 3.32 (pt, 1H, J$_{3,4}$=J$_{4,5}$=9.7 Hz, H-4$_D$), 2.07 (s, 3H, CH$_{3Ac}$), 1.95 (s, 3H, CH$_{3NHAc}$), 1.53 (sex, 2H, CH$_{2Pr}$), 1.16 (d, 3H, J$_{5,6}$=6.2 Hz, H-6$_D$), 1.09 (d, 3H, J$_{5,6}$=6.2 Hz, H-6$_C$), 0.83 (t, 3H, J=7.3 Hz, CH$_{3Pr}$).

$^{13}$C NMR (D$_2$O), δ 175.1 (NHCO), 173.7 (CO$_{Ac}$), 171.8 (C-6$_A$), 104.5 (C-1$_A$, $^1$J$_{CH}$=162.7 Hz), 102.3 (C-1$_B$, $^1$J$_{CH}$=164.9 Hz), 101.4 (C-1$_D$, $^1$J$_{CH}$=173.9 Hz), 98.7 (C-1$_C$, $^1$J$_{CH}$=174.4 Hz), 80.3 (C-3$_B$), 77.6 (C-2$_C$), 76.2 (C-4$_A$), 74.8 (C-5$_B$), 74.3 (C-4$_C$), 72.6 (C-5$_A$), 72.8 (C-3$_A$), 71.8 (C-4$_D$), 70.2 (C-2$_D$), 69.9 (C-3$_D$), 69.8 (2C, OCH$_{2Pr}$, C-2$_A$), 69.2 (C-5$_D$), 68.4 (C-3$_C$), 67.8 (C-4$_B$), 66.5 (C-5$_C$), 61.0 (C-6$_B$), 51.6 (C-2$_B$), 22.3 (CH$_{3NHAc}$), 22.0 (CH$_{2Pr}$), 20.5 (CH$_{3Ac}$), 16.6, 16.5 (2C, C-6$_D$, C-6$_C$), 9.8 (CH$_{3Pr}$).

HRMS (ESI$^+$): m/z 796.2884 (calcd for C$_{31}$H$_{51}$NO$_{21}$Na [M+Na]$^+$: m/z 798.2852).

HPLC (215 nm): =16.4 min.

Propyl α-L-rhamnopyranosyl-(1→2)-α-L-rhamnopyranosyl-(1→4)-β-D-galactopyranosyluronic acid-(1→3)-2-acetamido-2-deoxy-β-D-galactopyranoside (XXXV)

$^1$H NMR (D$_2$O), δ 5.20 (d, 1H, J$_{1,2}$=1.3 Hz, H-1$_D$), 4.80 (d, 1H, J$_{1,2}$=1.4 Hz, H-1$_C$), 4.36 (d, 2H, J$_{1,2}$=8.0 Hz, H-1$_A$, H-1$_B$), 4.36 (d, 1H, J$_{4,5}$=1.1 Hz, H-5$_A$), 4.20 (dd, 1H, J$_{3,4}$=2.8 Hz, H-4$_A$), 4.08 (dd, 1H, J$_{2,3}$=3.0 Hz, H-4$_B$), 3.93 (dd, 1H, H-2$_D$), 3.90 (dd, 1H, J$_{2,3}$=3.4 Hz, H-2$_C$), 3.86 (dd, 1H, J$_{1,2}$=8.6 Hz, J$_{2,3}$=10.8 Hz, H-2$_B$), 3.72 (dd$_{po}$, 1H, J$_{2,3}$=3.3 Hz, H-3$_D$), 3.71-3.63 (m, 5H, OCH$_{2Pr}$, H-3$_A$, H-3$_B$, H-6a$_B$, H-6b$_B$), 3.61 (dd$_{po}$, 1H, H-3$_C$), 3.57-3.50 (m, 2H, H-5$_C$, H-5$_B$), 3.46 (dd$_{po}$, 1H, J$_{2,3}$=9.8 Hz, H-2$_A$), 3.45-3.38 (m, 2H, OCH$_{2Pr}$, H-5$_D$), 3.29 (pt, 1H, J$_{3,4}$=J$_{4,5}$=9.7 Hz, H-4$_D$), 3.28 (pt, 1H, J$_{3,4}$=J$_{4,5}$=9.7 Hz, H-4$_C$), 1.86 (s, 3H, CH$_{3NHAc}$), 1.40 (sex, 2H, CH$_{2Pr}$), 1.10 (d, 3H, J$_{5,6}$=6.2 Hz, H-6$_C$), 1.09 (d, 3H, J$_{5,6}$=6.2 Hz, H-6$_D$), 0.72 (t, 3H, J=7.3 Hz, CH$_{3Pr}$).

$^{13}$C NMR (D$_2$O), δ 174.7 (NHCO), 171.5 (C-6$_A$), 104.5 (C-1$_A$, $^1$J$_{CH}$=164.1 Hz), 102.0 (C-1$_C$, $^1$J$_{CH}$=172.0 Hz), 101.1 (C-1$_B$, $^1$J$_{CH}$=161.8 Hz), 99.9 (C-1$_D$, $^1$H$_{CH}$=175.7 Hz), 80.7 (C-3$_B$), 78.2 (C-2$_D$), 76.3 (C-4$_A$), 74.6 (C-5$_B$), 72.7 (C-3$_A$), 72.5 (C-5$_A$), 72.1 (OCH$_{2Pr}$), 71.9, 71.7 (2C, C-4$_C$, C-4$_D$), 69.9 (2C, C-2$_C$, C-3$_C$), 69.7, 69.6 (2C, C-2$_A$, C-3$_D$), 69.2 (C-5$_D$), 68.9 (C-5$_C$), 67.7 (C-4$_B$), 60.8 (C-6$_B$), 51.2 (C-2$_B$), 22.1 (CH$_{3NHAc}$), 22.0 (CH$_{2Pr}$), 16.6, 16.5 (2C, C-6$_D$, C-6$_C$), 9.5 (CH$_{3Pr}$).

HRMS (ESI$^+$): m/z 754.2769 (calcd for C$_{29}$H$_{49}$NO$_{20}$Na [M+Na]$^+$: m/z 754.2745).

HPLC (215 nm): R$_t$=8.9 min.

Propyl 3-O-acetyl-α-L-rhamnopyranosyl-(1→2)-α-L-rhamnopyranosyl-(1→4)-β-D-galactopyranosyluronic acid-(1→3)-2-acetamido-2-deoxy-β-D-galactopyranoside (XXXVI)

$^1$H NMR (D$_2$O), δ 5.32 (d, 1H, J$_{1,2}$=1.4 Hz, H-1$_D$), 4.90 (dd$_{po}$, 1H, J$_{2,3}$=3.3 Hz, J$_{3,4}$=9.9 Hz, H-3$_C$), 4.90 (d$_o$, 1H, H-1$_C$), 4.44 (d, 1H, J$_{1,2}$=8.6 Hz, H-1$_B$), 4.43 (d, 1H, J$_{1,2}$=7.8 Hz, H-1$_A$), 4.34 (d, 1H, J$_{4,5}$=1.1 Hz, H-5$_A$), 4.28 (dd, 1H, J$_{3,4}$=2.8 Hz, H-4$_A$), 4.16 (d, 1H, J$_{3,4}$=3.0 Hz, H-4$_B$), 4.12 (dd, 1H, J$_{1,2}$=1.9 Hz, H-2$_D$), 4.02 (dd, 1H, J$_{2,3}$=3.2 Hz, H-2$_D$), 3.94 (dd, 1H, J$_{2,3}$=10.8 Hz, H-2$_B$), 3.80 (dd, 1H, H-3$_D$), 3.79-3.68 (m, 5H, H-3$_A$, H-3$_B$, OCH$_{2Pr}$, H-6a$_B$, H-6b$_B$), 3.61 (m, 1H, H-5$_B$), 3.56 (pt$_o$, 1H, J$_{3,4}$=J$_{4,5}$=9.9 Hz, H-4$_C$), 3.58-3.51 (m, 3H, H-5$_C$, H-5$_D$, H-2$_A$), 3.49 (dt, 1H, J=10.2 Hz, OCH$_{2Pr}$), 3.41 (pt, 1H, J$_{3,4}$=J$_{4,5}$=9.7 Hz, H-4$_D$), 2.09 (s, 3H, CH$_{3Ac}$), 1.94 (s, 3H, CH$_{3NHAc}$), 1.48 (sex, 2H, CH$_{2Pr}$), 1.22 (d, 3H, J$_{5,6}$=6.2 Hz, H-6$_C$), 1.19 (d, 3H, J$_{5,6}$=6.2 Hz, H-6$_D$), 0.79 (t, 3H, CH$_{3Pr}$).

$^{13}$C NMR (D$_2$O), δ 174.8 (NHCO), 173.6 (CO$_{Ac}$), 171.6 (C-6$_A$), 104.6 (C-1$_A$, $^1$J$_{CH}$=163.6 Hz), 101.7 (C-1$_C$, $^1$J$_{CH}$=172.6 Hz), 101.2 (C-1$_B$, $^1$J$_{CH}$=163.6 Hz), 99.9 (C-1$_D$, $^1$J$_{CH}$=173.5 Hz), 80.7 (C-3$_B$), 78.7 (C-2$_D$), 76.4 (C-4$_A$), 74.7 (C-5$_B$), 73.5 (C-3$_C$), 72.9 (C-5$_A$), 72.7 (C-3$_A$), 72.3 (OCH$_{2Pr}$), 71.8 (C-4$_D$), 69.8 (C-4$_C$), 69.7 (2C, C-3$_D$, C-2$_A$*), 69.3 (C-5$_C$*), 69.0 (C-5$_D$), 68.0 (C-2$_C$), 67.8 (C-4$_B$), 60.9 (C-6$_B$), 51.3 (C-2$_B$), 22.2 (CH$_{3NHAc}$), 22.1 (CH$_{2Pr}$), 20.4 (CH$_{3Ac}$), 16.7, 16.6 (2C, C-6$_D$, C-6$_C$), 9.6 (CH$_{3Pr}$)

HRMS (ESI$^+$): m/z 796.2878 (calcd for C$_{31}$H$_{51}$NO$_{21}$Na [M+Na]$^+$: m/z 796.2852).

HPLC (215 nm): R$_t$=9.5 min.

Characterization of Additional Propyl Pentasaccharides Mimicking Frame-Shifted Repeating Units of SF6, SF6a and/or E. coli O147 O-Ags, Obtained According to a Linear Synthetic Strategy.

Propyl 3-O-acetyl-α-L-rhamnopyranosyl-(1→2)-α-L-rhamnopyranosyl-(1→4)-β-D-galactopyranosyluronic acid-(1→3)-2-acetamido-2-deoxy-β-D-galactopyranosyl-(1→2)-3-O-acetyl-α-L-rhamnopyranoside (XIX)

$^1$H NMR (D$_2$O), δ 5.31 (d, 1H, J$_{1,2}$=1.2 Hz, H-1$_D$), 4.96 (dd, 1H, J$_{2,3}$=3.0 Hz, J$_{3,4}$=9.0 Hz, H-3$_C$), 4.88 (dd, 1H, J$_{2,3}$=3.0 Hz, J$_{3,4}$=9.8 Hz, H-3$_{C'}$), 4.88-4.87 (m, 2H, H-1$_C$, H-1$_{C'}$), 4.76 (d, 1H, J$_{1,2}$=7.9 Hz, H-1$_A$), 4.42 (d, 1H, J$_{1,2}$=8.2 Hz, H-1$_B$), 4.33 (d$_{po}$, 1H, J$_{4,5}$=1.2 Hz, H-5$_A$), 4.26 (dd$_o$, 1H, H-4$_A$), 4.14 (bd, 1H, J$_{3,4}$=2.6 Hz, H-4$_B$), 4.11 (dd, 1H, J$_{1,2}$=1.9 Hz, H-2$_{C'}$), 4.03 (pt, 1H, H-2$_C$), 4.01 (dd, 1H, J$_{2,3}$=3.3 Hz, H-2$_D$), 3.92 (bdd, 1H, J$_{2,3}$=10.6 Hz, H-2$_B$), 3.82 (dd, 1H, H-3$_B$), 3.80-3.64 (m, 6H, H-3$_D$, H-3$_A$, H-6a$_B$, H-6b$_B$, H-5$_C$, H-5$_{C'}$), 3.62-3.47 (m, 5H, H-5$_B$, H-5$_D$, OCH$_{2Pr}$, H-2$_A$, H-4$_{C'}$), 3.47-3.33 (m, 3H, OCH$_{2Pr}$, H-4$_D$, H-4$_C$), 2.10 (s, 3H, CH$_{3Ac-3C'}$), 2.07 (s, 3H, CH$_{3Ac-3C}$), 1.98 (s, 3H, CH$_{3NHAc}$), 1.52 (psex, 2H, J=7.0 Hz, CH$_{2Pr}$), 1.23-1.15 (m, 9H, H-6$_D$, H-6$_C$, H-6$_{C'}$), 0.83 (t, 3H, J=7.4 Hz, CH$_{3Pr}$).

$^{13}$C NMR (D$_2$O), δ 174.5 (NHCO), 173.6 (CO$_{Ac-3C'}$), 173.4 (CO$_{Ac-3C}$), 171.6 (C-6$_A$), 104.3 (C-1$_A$), 102.6 (C-1$_B$), 101.7 (C-1$_{C'}$), 99.9 (C-1$_D$), 98.5 (C-1$_C$), 79.8 (C-3$_B$), 78.7 (C-2$_D$), 76.4 (C-4$_A$), 76.2 (C-2$_C$), 74.5 (C-5$_B$), 73.5 (C-3$_{C'}$), 72.9 (2C, C-3$_C$, C-5$_A$), 72.6 (C-3$_A$), 71.8 (C-4$_D$), 70.9 (C-4$_C$), 69.8 (C-4$_{C'}$), 69.7-68.7 (6C, C-3$_D$, OCH$_{2Pr}$, C-2$_A$, C-5$_{C'}$, C-5$_D$, C-5$_C$), 68.0 (C-2$_{C'}$), 67.5 (C-4$_B$), 60.8 (C-6$_B$), 51.5 (C-2$_B$), 22.3 (CH$_{3NHAc}$), 21.9 (CH$_{2Pr}$), 20.5, 20.4 (2C, CH$_{3Ac}$), 16.6-16.4 (3C, C-6$_D$, C-6$_C$, C-6$_{C'}$), 9.8 (CH$_{3Pr}$).

Propyl 2-O-acetyl-α-L-rhamnopyranosyl-(1→2)-α-L-rhamnopyranosyl-(1→4)-β-D-galactopyranosyluronic acid-(1→3)-2-acetamido-2-deoxy-β-D-galactopyranosyl-(1→2)-3-O-acetyl-α-L-rhamnopyranoside (XIX')

$^1$H NMR (D$_2$O), δ 5.28 (d, 1H, J$_{1,2}$=1.7 Hz, H-1$_D$), 5.12 (dd, 1H, J$_{1,2}$=1.7 Hz, J$_{2,3}$=3,4 Hz, H-2$_{C'}$), 4.96 (dd, 1H, J$_{2,3}$=3.0 Hz, J$_{3,4}$=9.0 Hz, H-3$_C$), 4.92 (d, 1H, J$_{1,2}$=1.5 Hz, H-1$_{C'}$), 4.88 (d$_o$, 1H, H-1$_C$), 4.75 (d, 1H, J$_{1,2}$=7.9 Hz, H-1$_A$), 4.42 (d, 1H, J$_{1,2}$=8.2 Hz, H-1$_B$), 4.33 (d$_{po}$, 1H, J$_{4,5}$=1.2 Hz, H-5$_A$), 4.26 (dd$_o$, 1H, H-4$_A$), 4.14 (bd, 1H, J$_{3,4}$=2.6 Hz,

H-4$_B$), 4.03 (pt, 1H, H-2$_C$), 4.01 (dd, 1H, J$_{2,3}$=3.3 Hz, H-2$_D$), 3.92 (bdd, 1H, J$_{2,3}$=10.6 Hz, H-2$_B$), 3.87 (dd, 1H, J$_{3,4}$=9.8 Hz, H-3$_{C'}$), 3.82 (dd, 1H, H-3$_B$), 3.80-3.64 (m, 6H, H-3$_D$, H-3$_A$, H-6a$_B$, H-6b$_B$, H-5$_C$, H-5$_{C'}$), 3.62-3.47 (m, 4H, H-5$_B$, H-5$_D$, OCH$_{2Pr}$, H-2$_A$), 3.47-3.33 (m, 4H, OCH$_{2Pr}$, H-4$_D$, H-4$_C$, H-4$_{C'}$), 2.10 (s, 3H, CH$_{3Ac-3C}$), 2.06 (s, 3H, CH$_{3Ac-2C}$), 1.98 (s, 3H, CH$_{3NHAc}$), 1.52 (psex, 2H, J=7.0 Hz, CH$_{2Pr}$), 1.23-1.15 (m, 9H, H-6$_D$, H-6$_C$, H-6$_{C'}$), 0.83 (t, 3H, J=7.4 Hz, CH$_{3Pr}$).

$^{13}$C NMR (D$_2$O), δ 174.5 (NHCO), 173.4 (CO$_{Ac-3C}$), 173.1 (CO$_{Ac-2C}$), 171.6 (C-6$_A$), 104.3 (C-1$_A$), 102.6 (C-1$_B$), 99.9 (C-1$_D$), 99.1 (C-1$_{C'}$), 98.5 (C-1$_C$), 79.8 (C-3$_B$), 78.8 (C-2$_D$), 76.4 (C-4$_A$), 76.2 (C-2$_C$), 74.5 (C-5$_B$), 72.9 (2C, C-3$_C$, C-5$_A$), 72.6 (C-3$_A$), 72.3 (C-2$_{C'}$), 72.2 (C-4$_{C'}$), 71.8 (C-4$_D$), 70.9 (C-4$_C$), 69.7-68.7 (6C, C-3$_D$, OCH$_{2Pr}$, C-2$_A$, C-5$_{C'}$, C-5$_D$, C-5$_C$), 68.5 (C-3$_{C'}$), 67.5 (C-4$_B$), 60.8 (C-6$_B$), 51.5 (C-2$_B$), 22.3 (CH$_{3NHAc}$), 21.9 (CH$_{2Pr}$), 20.5, 20.3 (2C, CH$_{3Ac}$), 16.6-16.4 (3C, C-6$_D$, C-6$_C$, C-6$_{C'}$), 9.8 (CH$_{3Pr}$).

HRMS (ESI$^+$): m/z 984.3530 (calcd for C$_{36}$H$_{63}$NO$_{26}$Na [M+Na]$^+$: m/z 984.3530).

HPLC (215 nm): R$_t$=13.2 min.

Propyl 4-O-acetyl-α-L-rhamnopyranosyl-(1→2)-α-L-rhamnopyranosyl-(1→4)-β-D-galactopyranosyluronic acid-(1→3)-2-acetamido-2-deoxy-β-D-galactopyranosyl-(1→2)-3-O-acetyl-α-L-rhamnopyranoside (XIX")

$^1$H NMR (D$_2$O), δ 5.24 (d, 1H, 1$_{1,2}$=1.3 Hz, H-1$_D$), 4.93 (dd, 1H, J$_{2,3}$=3.0 Hz, J$_{3,4}$=10.0 Hz, H-3$_C$), 4.86 (d$_o$, 1H, J$_{1,2}$=1.7 Hz, H-1$_{C'}$), 4.85 (d$_o$, 1H, J$_{1,2}$=1.7 Hz, H-1$_C$), 4.75 (t, 1H, 1$_{3,4}$=J$_{4,5}$=9.9 Hz, H-4$_{C'}$), 4.41 (d, 1H, J$_{1,2}$=7.8 Hz, H-1$_A$), 4.38 (d, 1H, J$_{1,2}$=8.3 Hz, H-1$_B$), 4.21 (bs, 2H, H-4$_A$, H-5$_A$), 4.11 (d, 1H, J$_{3,4}$=3.0 Hz, H-4$_B$), 4.01 (dd, 1H, J$_{2,3}$=2.7 Hz, H-2$_C$), 3.97 (dd$_{po}$, 1H, J$_{2,3}$=3.5 Hz, H-2$_{C'}$), 3.96 (dd$_{po}$, 1H, H-2$_D$), 3.88 (dd$_{po}$, 1H, J$_{2,3}$=11.0 Hz, H-2$_B$), 3.85 (dd$_{po}$, 1H, J$_{2,3}$=3.4 Hz, J$_{3,4}$=9.9 Hz, H-3$_{C'}$), 3.79-3.69 (m, 4H, H-3$_A$, H-3$_B$, H-3$_D$, H-5$_{C'}$), 3.68-3.62 (m, 3H, H-5$_C$, H-6a$_B$, H-6b$_B$), 3.56-3.47 (m, 4H, H-5$_D$, OCH$_{2Pr}$, H-2$_A$, H-5$_B$), 3.40 (1, J$_{3,4}$=J$_{4,5}$=9.7 Hz, H-4$_C$), 3.39 (dt$_{po}$, 1H, J=6.3 Hz, J=9.8 Hz, OCH$_{2Pr}$), 3.41 (pt, 1H, J$_{3,4}$=J$_{4,5}$=9.8 Hz, H-4$_D$), 2.06 (s, 3H, CH$_{3Ac}$), 2.03 (s, 3H, CH$_{3Ac}$), 1.94 (s, 3H, CH$_{3NHAc}$), 1.49 (sex, 2H, J=7.1 Hz, CH$_{2Pr}$), 1.17 (d, 3H, J$_{5,6}$=6.3 Hz, H-6$_C$), 1.19 (d, 3H, J$_{5,6}$=6.2 Hz, H-6$_D$), 1.03 (d, 3H, J$_{5,6}$=6.2 Hz, H-6$_{C'}$), 0.79 (t, 3H, J=7.4 Hz, CH$_{3Pr}$).

$^{13}$C NMR (D$_2$O), δ 174.5 (NHCO), 173.7, 173.4 (2C, CO$_{Ac}$), 171.6 (C-6$_A$), 104.3 (C-1$_A$), 102.5 (C-1$_B$), 102.4 (C-1$_C$), 99.7 (C-1$_D$), 99.3 (C-1$_{C'}$), 79.8 (C-3$_B$), 78.6 (C-2$_D$), 76.2 (2C, C-2$_C$, C-4$_A$), 74.6 (C-5$_B$), 73.8 (C-4$_{C'}$), 73.2 (C-5$_A$), 73.7 (2C, C-3$_C$, C-3$_A$), 71.8 (C-4$_D$), 69.9-69.2 (5C, C, C-2$_{C'}$, C-4$_C$, C-2$_A$, C-3$_D$, OCH$_{2Pr}$), 68.4 (C-5$_D$), 68.1 (C-5$_C$), 67.5 (C-3$_{C'}$), 66.8 (2C, C-4$_B$, C-5$_{C'}$), 60.7 (C-6$_B$), 51.2 (C-2$_B$), 22.3 (CH$_{3NHAc}$), 21.9 (CH$_{2Pr}$), 20.5, 20.4 (2C, CH$_{3Ac}$), 16.5, 16.4 (3C, C-6$_D$, C-6$_C$, C-6$_{C'}$), 9.7 (CH$_{3Pr}$).

Propyl α-L-rhamnopyranosyl-(1→2)-α-L-rhamnopyranosyl-(1→4)-β-D-galactopyranosyluronic acid-(1→3)-2-acetamido-2-deoxy-β-D-galactopyranosyl-(1→2)-α-L-rhamnopyranoside (XX)

$^1$H NMR (D$_2$O), δ 5.28 (d, 1H, J$_{1,2}$=1.4 Hz, H-1$_D$), 4.90 (d, 1H, J$_{1,2}$=1.5 Hz, H-1$_C$), 4.88 (d, 1H, J$_{1,2}$=1.6 Hz, H-1$_{C'}$), 4.63 (d, 1H, J$_{1,2}$=8.4 Hz, H-1$_B$), 4.45 (d, 1H, J$_{1,2}$=7.9 Hz, H-1$_A$), 4.34 (d, 1H, J$_{4,5}$=1.1 Hz, H-5$_A$), 4.28 (dd, 1H, J$_{3,4}$=2.9 Hz, H-4$_A$), 4.16 (d, 1H, J$_{3,4}$=3.2 Hz, H-4$_B$), 4.01 (dd, 1H, J$_{3,4}$=3.2 Hz, H-2$_D$), 4.00-3.93 (m, 3H, H-2$_B$, H-2$_C$, H-2$_{C'}$), 3.83-3.67 (m, 7H, H-3$_A$, H-3$_B$, H-3$_C$, H-3$_{C'}$, H-6a$_B$, H-6b$_B$, H-3$_D$), 3.66-3.49 (m, 6H, H-5$_C$, H-5$_{C'}$, H-5$_B$, OCH$_{2Pr}$, H-5$_D$, H-2$_A$), 3.43 (dt, 1H, J=6.3 Hz, J=9.8 Hz, OCH$_{2Pr}$), 3.37 (pt, 1H, J$_{3,4}$=J$_{4,5}$=9.8 Hz, H-4$_D$), 3.36 (pt, 1H, 1$_{3,4}$=J$_{4,5}$=9.7 Hz, H-4$_{C'}$), 3.27 (pt, 1H, 1$_{3,4}$=J$_{4,5}$=9.6 Hz, H-4$_C$), 1.96 (s, 3H, CH$_{3NHAc}$), 1.53 (psex, 2H, CH$_{2Pr}$), 1.21-1.16 (m, 9H, H-6$_C$, H-6$_{C'}$, H-6$_D$), 0.83 (t, 3H, J=7.5 Hz, CH$_{3Pr}$).

$^{13}$C NMR (D$_2$O), δ 175.0 (NHCO), 171.6 (C-6$_A$), 104.5 (C-1$_A$, $^1$J$_{CH}$=163.1 Hz), 102.7 (C-1$_B$, $^1$J$_{CH}$=163.1 Hz), 102.1 (C-1$_{C'}$, $^1$J$_{CH}$=171.3 Hz), 100.0 (C-1$_D$, $^1$J$_{CH}$=175.3 Hz), 98.5 (C-1$_C$, $^1$J$_{CH}$=174.0 Hz), 80.4 (C-3$_B$), 78.5 (C-2$_C$), 78.3 (C-2$_D$), 76.3 (C-4$_A$), 74.7 (C-5$_B$), 72.9 (C-5$_A$), 72.6 (C-3$_A$), 72.3 (C-4$_C$), 72.1, 71.9 (2C, C-4$_D$, C-4$_{C'}$), 70.1 (C-2$_{C'}$), 70.0 (2C, C-3$_C$, C-3$_{C'}$), 69.8 (C-2$_A$), 69.7 (C-3$_D$), 69.6 (OCH$_{2Pr}$), 69.3 (C-5$_D$), 69.0 (C-5$_{C'}$), 68.6 (C-5$_C$), 67.7 (C-4$_B$), 60.9 (C-6$_B$), 51.6 (C-2$_B$), 22.4 (CH$_{3NHAc}$), 21.9 (CH$_{2Pr}$), 16.7-16.5 (3C, C-6$_D$, C-6$_C$, C-6$_{C'}$), 9.8 (CH$_{3Pr}$).

HRMS (ESI$^+$): m/z 900.3400 (calcd for C$_{35}$H$_{59}$NO$_{24}$Na [M+Na]$^+$: m/z 900.3325).

HPLC (215 nm): R$_t$=10.7 min.

B. Convergent Synthetic Strategy

Convergent synthesis stands for a process whereby chain elongation engaged to obtain the oligo- or polysaccharide target involves pre-defined building blocks comprising—at least in part—more than one residue. Building blocks of interest include acceptors (bearing the "reducing" endchain residue), donors (bearing the non reducing endchain residue), or donors acting as potential acceptors (designed to allow selective unmasking of the hydroxyl group involved in the next glycosylation step), which are often used repeatedly in the synthesis of targets larger than 1 repeating unit, preferentially more than 2 repeating unit. Selected building blocks are combined in a predetermined order. Convergent strategies are advantageously used on one hand to reach oligo- and polysaccharide targets comprising more than one repeating unit and on the other hand to avoid difficult glycosylations at an advanced stage.

The need for highly convergent routes to synthetic oligo- and polysaccharides mimicking large fragments of the O—Ag of SF6, SF6a and/or E. coli O147 (up to 10 repeating units), led us to design a set of building blocks (see Table I), the combination of which provides an access—in theory—to the required targets. Advantageously, the selected building blocks take into account the diversity of both endchain residues and chain length within the O—Ag fragments of interest. In the search for efficiency, they were designed according to a disconnection at the B-C linkage.

Synthesis of Selected Building Blocks Shown in Table I from Key Intermediates

One major achievement is that all selected building blocks derive from common precursors designed on purpose. In particular, disaccharide (HO)$_2$-AB (241) and rhamnosyl donors protected at position 3 in the form of a para-methoxybenzyl ether (43, 119, 166) were identified as important intermediates.

Disaccharide AB as a template: as seen in scheme 6, upon appropriate tuning encompassing the controlled oxidation/benzylation of its free primary hydroxyl group, the key diol 241 is converted to the HO-AB acceptor 242. On the one hand, masking the 4$_A$-OH of the later followed by appropriate anomeric deallylation/activation of the fully protected intermediate 244, provided the useful AB-TCA and AB-PTFA donors (246, 247), via hemiacetal 245. On the other hand, acceptor 242 was efficiently glycosylated at position 4$_A$, to give trisaccharide 277, which was converted to the corresponding DAB-PTFA donor (283). Selective delevulinoylation of the fully protected 277, and subsequent glycosylation at the 2$_D$-OH gave tetrasaccharide 279, which was advantageously converted to the HO-CDAB acceptor (280) and to the CDAB-PTFA donor (284), following appropriate protecting group manipulation.
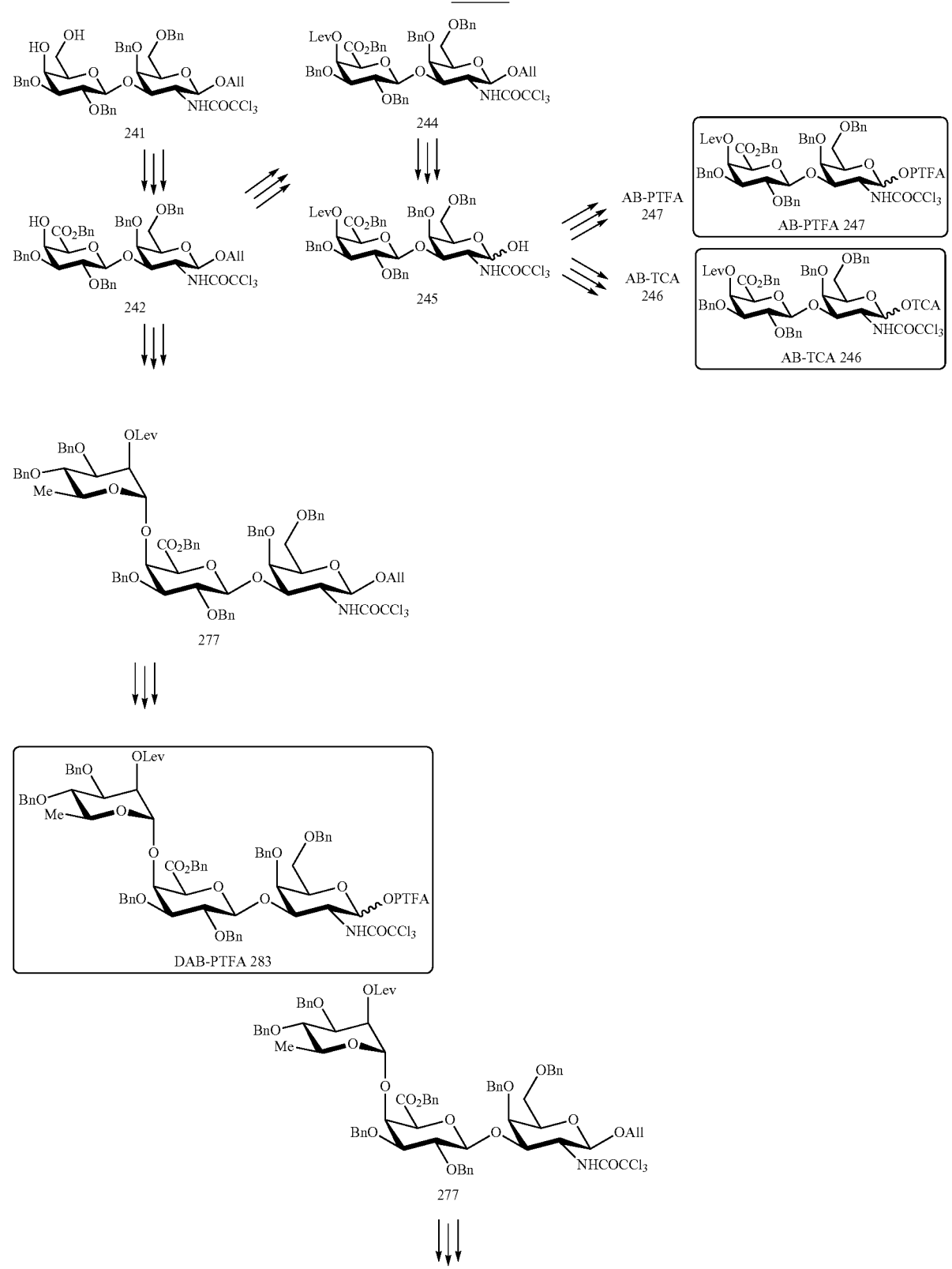
Scheme 6

-continued

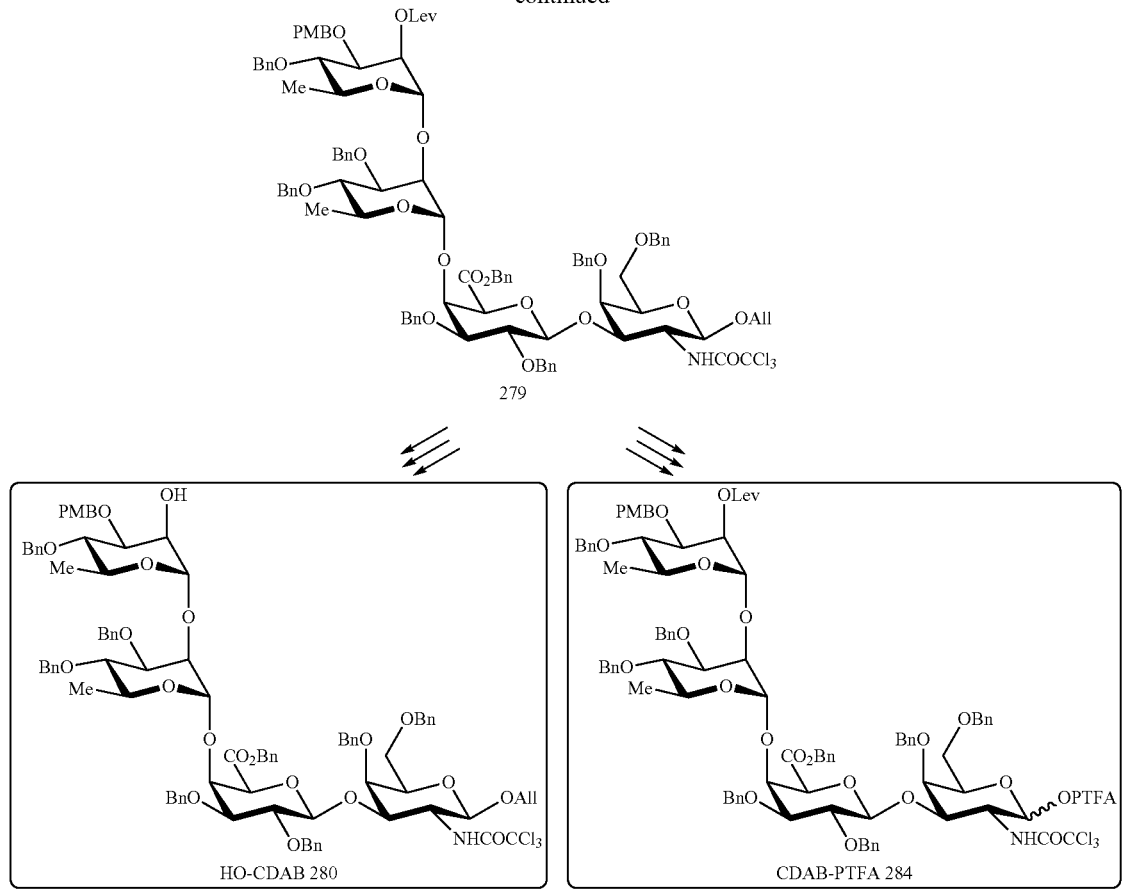

Rhamnosyl donors C as major intermediates: as seen in scheme 7, when reacted with the known allyl 3,4-di-O-benzyl-α-L-rhamnoside acceptor (D),[29] the trichloro-acetimidate donor 43 gave the fully protected rhamnobioside 47, which was easily turned into the corresponding acceptor 48, upon selective unmasking of OH-$2_C$ under transesterification conditions. Alternatively, when an appropriate HO-DA acceptor is used instead of the above mentioned D rhamnoside, for coupling to the C-TCA (119) or C-PTFA (166) donors, the fully protected CDA trisaccharide is isolated in yields above 90%, and next may be easily converted to the required HO-CDA acceptor (169), upon controlled hydrazinolysis of the levulinoyl ester at position $2_C$ in a buffered medium. In a similar fashion, changing the above mentioned HO-DA acceptor for a suitable HO-DAB acceptor in the glycosylation reaction, allowed chain elongation at the later to give the fully protected CDAB tetrasaccharide (279), which was advantageously converted either to the HO-CDAB acceptor (280) or to the CDAB-PTFA donor (284), as already mentioned.

Scheme 7

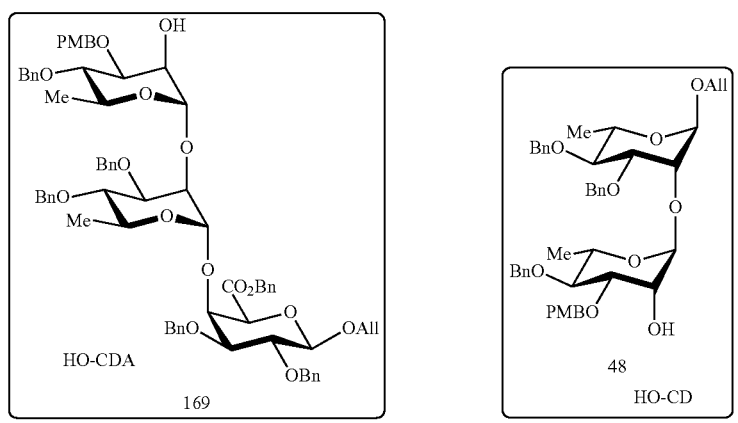

-continued
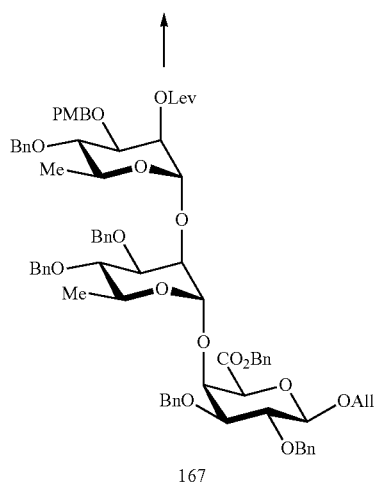
167
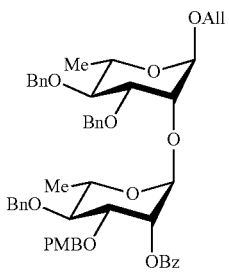
47
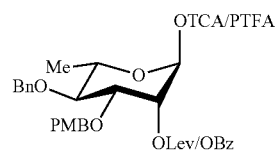
43, 119 or 166
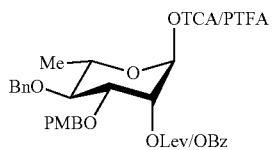
43, 119 or 166
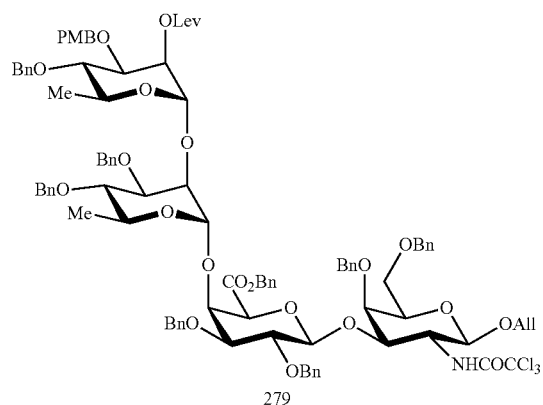
279

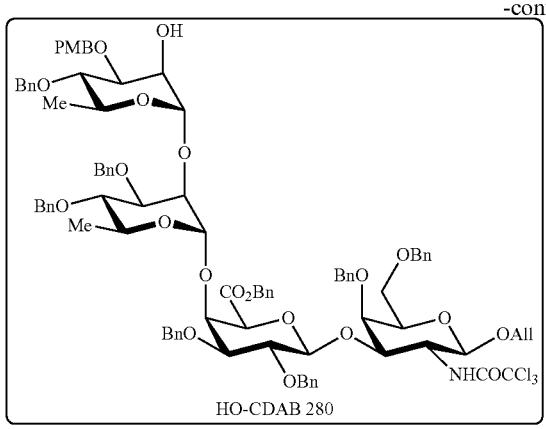

HO-CDAB 280

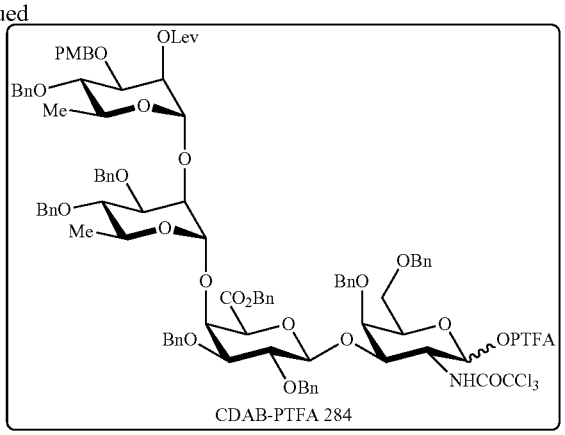

CDAB-PTFA 284

Synthetic Protocols and Characterization of Key Intermediates and all Novel Building Blocks Listed in Table 1

Phenyl 3,4,6-tri-O-benzyl-2-deoxy-2-trichloroacetamido-1-thio-β-D-galactopyranoside (24)

A solution of thioglycoside 21[30] (5.00 g, 9.21 mmol) in anhyd. MeOH (100 mL) was treated by MeONa (0.5 Min MeOH, 311 μL, 1.44 mmol). The solution was stirred for 2 h at rt under an Ar atmosphere. The reaction was quenched with Dowex-H$^+$ resin. The resin was filtered and the filtrate was evaporated. Benzyl bromide (6.6 mL, 55.3 mmol, 6.0 equiv.) and NaH (60% in oil, 2.21 g, 55.3 mmol, 6.0 equiv.) were successively added to a solution of the crude triol in anhyd. DMF (74 mL) cooled to −10° C. The mixture was stirred under an Ar atmosphere keeping the temperature below 0° C. After 1.5 h, the reaction was quenched with the minimum amount of MeOH. The reaction mixture was diluted with EtOAc, and washed with water and brine. The organic layer was dried over anhyd. Na$_2$SO$_4$, filtered and concentrated. The residue was purified by flash chromatography (Tol/EtOAc 98:2 to 95:5) to give the target tri-O-benzyl derivative (24, 4.90 g, 77%), as a white solid.

$^1$H NMR (CDCl$_3$), δ 7.56-7.22 (m, 2H, H$_{Ar}$), 7.40-7.20 (m, 18H, H$_{Ar}$), 6.84 (d, 1H, J$_{NH,2}$=7.5 Hz, NH), 5.30 (d, 1H, J$_{1,2}$=10.2 Hz, H-1), 4.90 (d, 1H, J=11.4 Hz, H$_{Bn}$), 4.68 (d, 1H, J=11.2 Hz, H$_{Bn}$), 4.58 (d, 1H, H$_{Bn}$), 4.54 (d, 1H, H$_{Bn}$), 4.53 (d, 1H, J 11.8 Hz, H$_{Bn}$), 4.48 (d, 1H, H$_{Bn}$), 4.28 (dd, 1H, J$_{2,3}$=10.5 Hz, J$_{3,4}$=2.7 Hz, H-3), 4.09 (d, 1H, H-4), 3.94 (pdt, 1H, H-2), 3.78-3.68 (m, 3H, H-5, H-6a, H-6b).

$^{13}$C NMR (CDCl$_3$), δ 161.7 (NHCO), 138.4, 137.8, 137.3 (3C, C$_{IVAr}$), 132.8 (2C, C$_{Ar}$), 132.2 (C$_{IVAr}$), 130.0-127.6 (18C, C$_{Ar}$), 92.5 (CCl$_3$), 84.3 (C-1), 78.2 (C-3), 77.6 (C-5), 74.5, 73.6 (2C, C$_{Bn}$), 72.4 (C-4), 72.3 (CBn), 68.4 (C-6), 53.7 (C-2).

HRMS (ESI$^+$): m/z 708.1128 (calcd for C$_{35}$H$_{34}$Cl$_3$NO$_5$SNa [M+Na]$^+$: m/z 708.1121).

3,4,6-Tri-O-benzyl-2-deoxy-2-trichloroacetamido-α/β-D-galactopyranosyl N-phenyltrifluoroacetimidate (181)

The hemiacetal (1.85 g, 3.11 mmol), obtained from the thioglycoside 24, was dissolved in acetone (31 mL). N-(phenyl)trifluoroacetimidoyl chloride (1.29 g, 6.22 mmol) and Cs$_2$CO$_3$ (1.12 g, 3.42 mmol, 1.1 equiv.) were added to the solution. The mixture was stirred for 4 h at rt. The reaction mixture was filtered and concentrated. The residue was purified by flash chromatography (Chex/EtOAc 85:15 to 7:3+1% Et$_3$N) to give N-phenyltrifluoroacetimidate 181 (2.10 g, 88%) as a light yellow oil.

$^1$H NMR (CDCl$_3$), δ 7.61-7.09 (m, 18H, H$_{Ar}$), 6.77 (d, 2H, J=7.6 Hz, H$_{Ar}$), 6.48 (d$_o$, 1H, J$_{NH,2}$=7.7 Hz, NH), 6.47 (bs$_o$, 1H, H-1), 4.97 (d, 1H, J=11.4 Hz, H$_{Bn}$), 4.76 (d$_{po}$, 1H, J=11.9 Hz, H$_{Bn}$), 4.73 (m, 1H, H-2), 4.64 (d, 1H, H$_{Bn}$), 4.57-4.48 (m, 3H, H$_{Bn}$), 4.20 (bs, 1H, H-4), 4.07 (pt, 1H, H-5), 3.88 (dd, 1H, J$_{2,3}$=11.0 Hz, J$_{3,4}$=1.4 Hz, H-3), 3.72 (pt, 1H, J$_{5,6a}$=7.8 Hz, H-6a), 3.62 (dd, 1H, J$_{5,6b}$=5.7 Hz, J$_{6a,6b}$=9.1 Hz, H-6b).

$^{13}$C NMR (CDCl$_3$), δ 161.8 (NHCO), 143.1, 138.0, 137.7, 137.0 (4C, C$_{IVAr}$), 129.4-119.3 (20C, C$_{Ar}$), 94.3 (C-1, $^1$J$_{CH}$=162.9 Hz), 92.3 (CCl$_3$), 75.5 (C-3), 74.8, 73.7 (2C, C$_B$), 72.5 (C-5), 71.6 (C-4), 71.3 (C$_{Bn}$), 68.1 (C-6), 50.6 (C-2).

Allyl 4-O-benzyl-3-O-para-methoxybenzyl-α-L-rhamnopyranoside (9).[26] Bu$_2$SnO (37.2 g, 149.5 mmol, 1.1 equiv.) was added to a solution of the known allyl 4-O-benzyl-α-L-rhamnopyranoside[31] (40.0 g, 135.8 mmol) in anhyd. toluene (1.1 L). The mixture was stirred for 5 h at reflux using a "Dean-Stark" apparatus and subsequently concentrated under reduced pressure to give a 0.4 M solution. After cooling to rt, dry CsF (21.05 g, 138.6 mmol, 1.0 equiv.), dry TBAI (65.25 g, 175.6 mmol, 1.3 equiv.) and PMBCl (20.3 mL, 149.5 mmol, 1.1 equiv.) were successively added. The reaction mixture was stirred for 5 h at reflux, at which time monitoring by TLC (Chex/EtOAc 6:4) showed the conversion of the starting material (rf=0.22) into a major less polar product (rf=0.51). The temperature was lowered to 0° C., salts were removed by filtration (toluene wash) and volatiles were evaporated under reduced pressure. The residue was purified by flash chromatography (Chex/EtOAc 9:1 to 7:3) to give acceptor 9 (48.1 g, 81%) as an orange-yellow oil. Analytical data were as deseribed.[26]

2-O-Benzoyl-4-O-benzyl-3-O-para-methoxybenzyl-α-L-rhamnopyranosyl trichloroacetimidate (43)

The hemiacetal (7.89 g, 16.49 mmol) obtained from the known allyl glycoside 9,[26] benzoylated at position 2, was dissolved in DCE (25 mL). Trichloroacetonitrile (6.6 mL, 66.0 mmol) and DBU (616 μL, 4.12 mmol) were added, and the solution was stirred under an Ar atmosphere at rt for 30 min. The mixture was directly purified by flash chromatography (Chex/EtOAc 8:2+1% Et$_3$N) to give donor 43 (9.71 g, 95%) as a yellow oil.

$^1$H NMR (CDCl$_3$), δ 8.70 (s, 1H, NH), 8.13-6.81 (m, 14H, H$_{Ar}$), 6.33 (d, 1H, J$_{1,2}$=1.9 Hz, H-1), 5.73 (dd, 1H, H-2), 4.95 (d, 1H, J=11.1 Hz, H$_{Bn}$), 4.76 (d, 1H, J=11.1 Hz, H$_{PMB}$), 4.68 (d, 1H, H$_{Bn}$), 4.57 (d, 1H, H$_{PMB}$), 4.11 (dd, 1H, J$_{2,3}$=3.3 Hz, J$_{3,4}$=9.6 Hz, H-3), 4.03 (dq, 1H, J$_{4,5}$=9.6 Hz, H-5), 3.80 (s, 3H, CH$_{3PMB}$), 3.64 (pt, 1H, H-4), 1.41 (d, 3H, J$_{5,6}$=6.0 Hz, H-6).

$^{13}$C NMR (CDCl$_3$), δ 165.8 (CO), 160.2 (C=NH), 159.4 (C$_{IVPMB}$), 138.2 (C$_{IVBn}$), 133.3 (C$_{Bz}$), 130.0 (C$_{IVPMB}$), 129.9, 129.7, 128.5, 128.4, 128.3, 127.8, (12C, 11C$_{Ar}$, C$_{IVBz}$), 113.8 (2C, C$_{ArPMB}$), 95.4 (C-1), 90.9 (CCl$_3$), 79.3 (C-4), 77.0 (C-3), 75.5 (C$_{Bn}$), 71.4 (C$_{PMB}$), 70.8 (C-5), 68.2 (C-2), 55.2 (CH$_{3PMB}$), 18.2 (C-6).

Allyl (2-O-benzoyl-4-O-benzyl-3-O-para-methoxybenzyl-α-L-rhamnopyranosyl)-(1→2)-3,4-di-O-benzyl-α-L-rhamnopyranoside (47)

A mixture of the known allyl 2,4-di-O-benzyl-α-L-rhamnoside acceptor[28] (3.00 g, 7.81 mmol), donor 43 (5.84 g, 9.37 mmol), and powdered MS 4 (6.0 g) in anhyd. toluene (78 mL) was stirred at rt under an Ar atmosphere for 1 h. The suspension was cooled to −40° C., and TMSOTf (71 μL, 0.39 mmol) was added. The reaction mixture was stirred for 20 min at this temperature and Et$_3$N was added to quench the reaction. The suspension was filtered and the filtrate was concentrated to dryness. The residue was purified by flash chromatography (Chex/EtOAc 9:1) to give disaccharide 47 (6.30 g, 95%) as a yellow oil.

$^1$H NMR (CDCl$_3$), δ 8.13-8.08 (m, 2H, H$_{Ar}$), 7.62 (m, 1H, H$_{Ar}$), 7.53-7.47 (m, 2H, H$_{Ar}$), 7.37-7.15 (m, 17H, H$_{Ar}$), 6.83-6.78 (m, 2H, H$_{ArPMB}$), 5.89 (m, 1H, CH=$_{All}$), 5.77 (dd, 1H, H-2$_C$), 5.27 (m, 1H, J$_{trans}$=17.2 Hz, J$_{gem}$=1.6 Hz, =CH$_{2All}$), 5.20 (m, 1H, J$_{cis}$=10.5 Hz, =CH$_{2All}$), 5.14 (d, 1H, J$_{1,2}$=1.8 Hz, H-1$_C$), 4.93 (d, 1H, J=10.9 Hz, H$_{Bn}$), 4.92 (d, 1H, J=10.9 Hz, H$_{Bn}$), 4.80 (d, 1H, J$_{1,2}$=1.7 Hz, H-1$_D$), 4.78 (d, 1H, J=11.0 Hz, H$_{Bn}$), 4.71 (bs, 2H, H$_{Bn}$), 4.67 (d, 1H, J=10.9 Hz, H$_{Bn}$), 4.63 (d, 1H, J=10.9 Hz, H$_{Bn}$), 4.54 (d, 1H, J=11.0 Hz, H$_{Bn}$), 4.15 (m, 1H, H$_{All}$), 4.08 (dd, 1H, J$_{2,3}$=3.2 Hz, J$_{3,4}$=9.3 Hz, H-3$_C$), 4.05 (dd, 1H, J$_{2,3}$=2.9 Hz, H-2$_D$), 3.99-3.86 (m, 3H, H$_{All}$, H-3$_D$, H-5$_D$), 3.76 (s, 3H, CH$_{3PMB}$), 3.73 (dq, 1H, J$_{4,5}$=9.2 Hz, J$_{5,6}$=6.2 Hz, H-5$_D$), 3.54 (pt, 1H, J$_{4,5}$=9.4 Hz, H-4$_C$), 3.48 (pt, 1H, J$_{3,4}$=9.4 Hz, H-4$_D$), 1.36 (d, 3H, J$_{5,6}$=6.2 Hz, H-6$_C$), 1.32 (d, 3H, H-6$_D$).

$^{13}$C NMR (CDCl$_3$) partial, δ 165.5 (CO$_{Bz}$), 159.2 (C$_{IVPMB}$), 113.7 (2C, C$_{arPMB}$), 99.4 (C-1$_C$, $^1$J$_{CH}$=171.0 Hz), 97.9 (C-1$_D$, $^1$J$_{CH}$=170.0 Hz), 55.2 (CH$_{3PMB}$).

HRMS (ESI$^+$): m/z 867.3601 (calcd for C$_{51}$H$_{56}$O$_{11}$Na [M+Na]$^+$: m/z 867.3720).

Allyl (4-O-benzyl-3-O-para-methoxybenzyl-α-L-rhamnopyranosyl)-(1→2)-3,4-di-O-benzyl-α-L-rhamnopyranoside (48)

A solution of disaccharide 47 (6.27 g, 7.42 mmol) in anhyd. MeOH (74 mL) was treated with 0.5 M methanolic MeONa (7.4 mL, 3.7 mmol) at 60° C. The mixture was stirred at this temperature under an Ar atmosphere for 3 h, then at rt for 16 h. The reaction mixture was neutralized by addition of Dowex-H$^+$ resin. The suspension was filtered and volatiles were evaporated. The residue was purified by flash chromatography (Tol/EtOAc 8:2) to give acceptor 48 (5.2 g, 94%) as a white foam.

$^1$H NMR (CDCl$_3$), δ 7.39-7.27 (m, 17H, H$_{Ar}$), 6.91-6.87 (m, 2H, H$_{ArPMB}$), 5.88 (m, 1H, CH=$_{All}$), 5.27 (m, 1H, J$_{trans}$=17.2 Hz, J$_{gem}$=1.6 Hz, =CH$_{2All}$), 5.19 (m, 1H, J$_{cis}$=10.4 Hz, =CH$_{2All}$), 5.09 (d, 1H, J$_{1,2}$=1.5 Hz, H-1$_C$), 4.89 (d, 2H, J=11.0 Hz, H$_{Bn}$), 4.78 (d, 1H, J$_{1,2}$=1.7 Hz, H-1$_D$), 4.71 (d, 1H, J=11.6 Hz, H$_{Bn}$), 4.67 (bs$_o$, 2H, H$_{Bn}$), 4.66 (d, 1H, J=11.6 Hz, H$_{Bn}$), 4.65 (d$_{po}$, 1H, J=11.3 Hz, H$_{Bn}$), 4.63 (d, 1H, J=10.9 Hz, H$_{Bn}$), 4.17-4.10 (m, 2H, H$_{All}$, H-2$_C$), 4.05 (dd, 1H, J$_{2,3}$=2.9 Hz, H-2$_D$), 3.98-3.86 (m, 3H, H-3$_C$, H$_{All}$, H-3$_D$), 3.82 (dq, 1H, J$_{4,5}$=9.6 Hz, J$_{5,6}$=6.2 Hz, H-5$_C$), 3.80 (s, 3H, CH$_{3PMB}$), 3.71 (dq, 1H, J$_{4,5}$=9.4 Hz, J$_{5,6}$=6.2 Hz, H-5$_D$), 3.46 (pt$_{po}$, 1H, J$_{3,4}$=9.3 Hz, H-4$_C$), 3.41 (pt, 1H, J$_{3,4}$=9.7 Hz, H-4$_D$), 2.46 (d, 1H, J$_{OH,2}$=1.8 Hz, OH-2$_C$), 1.32 (d, 3H, H-6$_D$), 1.31 (d, 3H, H-6$_C$).

$^{13}$C NMR (CDCl$_3$) partial, δ 159.4 (C$_{IVPMB}$), 114.0 (2C, C$_{arPMB}$), 100.7 (C-1$_C$, $^1$J$_{CH}$=171.7 Hz), 98.0 (C-1$_D$, $^1$J$_{CH}$=170.1 Hz), 55.2 (CH$_{3PMB}$).

HRMS (ESI$^+$): m/z 763.3458 (calcd for C$_{44}$H$_{52}$O$_{10}$Na [M+Na]$^+$: m/z 763.3449).

4-O-Benzyl-2-O-levulinoyl-3-O-para-methoxybenzyl-α/β-L-rhamnopyranosyl trichloroacetimidate (119)

The hemiacetal (10.0 g, 21.16 mmol) obtained from the known allyl glycoside 9,[26] levulinoylated at position 2. was dissolved in anhyd. DCE (42 mL) and stirred under an Ar atmosphere. Trichloroacetonitrile (10.6 mL, 105.8 mmol) and DBU (0.95 mL, 6.3 mmol) were added at rt. The reaction mixture was purified as such by flash chromatography (Chex/EtOAc 7:3 to 1:1+1% Et$_3$N) to give a 7.5:1 α/β mixture of trichloroacetimidate 119 (12.66 g, 97%) as a light yellow oil (a/3 ratio 7.5:1).

$^1$H NMR (CDCl$_3$), δ 8.67 (s, 1H, NH), 7.41-7.26 (m, 7H, H$_{Ar}$), 6.89-6.84 (m, 2H, 8.7 Hz, H$_{ArPMB}$), 6.19 (d, 1H, J$_{1,2}$=1.9 Hz, H-1), 5.47 (dd, 1H, J$_{2,3}$=3.3 Hz, H-2), 4.94 (d, 1H, J=10.9 Hz, H$_{Bn}$), 4.66 (d, 1H, J=10.9 Hz, H$_{Bn}$), 4.65 (d, 1H, H$_{Bn}$), 4.51 (d, 1H, H$_{Bn}$), 3.98 (dd, 1H, J$_{3,4}$=9.6 Hz, H-3), 3.94 (dq, 1H, J$_{4,5}$=9.4 Hz, H-5), 3.82 (s, 3H, CH$_{3PMB}$), 3.50 (pt, 1H, H-4), 2.84-2.72 (m, 4H, CH$_{2Lev}$), 2.22 (s, 3H, CH$_{3Lev}$), 1.36 (d, 3H, J$_{5,6}$=6.2 Hz, H-6).

$^{13}$C NMR (CDCl$_3$), δ 206.3 (CO$_{Lev}$), 171.9 (CO$_{2Lev}$), 160.1 (C=NH), 159.4 (C$_{IVArPMB}$), 138.1 (C$_{IVAr}$), 130.0-127.9 (8C, 7C$_{Ar}$, C$_{IVArPMB}$),), 113.8 (2C, C$_{ArPMB}$), 95.1 (C-1), 90.8 (CCl$_3$), 79.2 (C-4), 76.6 (C-3), 75.6 (C$_{Bn}$), 71.5 (C$_{PMB}$), 70.7 (C-5), 67.8 (C-2), 55.3 (CH$_{3PMB}$), 38.0 (COCH$_{2Lev}$), 29.9 (CH$_{3Lev}$), 28.1 (CO$_2$CH$_{2Lev}$), 18.0 (C-6).

4-O-Benzyl-3-O-para-methoxybenzyl-2-O-levulinoyl-α/β-L-rhamnopyranosyl N-phenyltrifluoroacetimidate (166)

The hemiacetal (5.0 g, 10.58 mmol) obtained from the known allyl glycoside 9,[26] levulinoylated at position 2, was dissolved in acetone (36 mL). N-(phenyl)trifluoroacetimidoyl chloride (4.39 g, 21.2 mmol) and Cs$_2$CO$_3$ (3.79 g, 11.6 mmol) were added to the solution. The mixture was stirred for 4 h at rt. The reaction mixture was filtered and concentrated. The residue was purified by flash chromatography (Chex/EtOAc 9:1 to 7:3+1% Et$_3$N) to give a 5:1 α/β mixture of N-phenyltrifluoroacetimidate 166 (6.70 g, 98%) as a light yellow oil.

$^1$H NMR (CDCl$_3$), δ 7.42-6.81 (m, 14H, H$_{Ar}$), 6.17 (bs, 1H, H-1), 5.46 (bs, 1H, H-2), 4.94 (d, 1H, J=10.6 Hz, H$_{Bn}$), 4.70-4.62 (m, 2H, H$_{Bn}$), 4.53 (d, 1H, J=10.6 Hz, H$_{Bn}$), 3.98 (dd, 1H, J$_{2,3}$=3.3 Hz, J$_{3,4}$=9.6 Hz, H-3), 3.90 (dq, 1H, J$_{4,5}$=9.1 Hz, J$_{5,6}$=6.1 Hz, H-5), 3.83 (s, 3H, CH$_{3PMB}$), 3.49 (pt, 1H, H-4), 2.82-2.69 (m, 4H, CH$_{2Lev}$), 2.21 (s, 3H, CH$_{3Lev}$), 1.32 (d, 3H, H-6).

$^{13}$C NMR (CDCl$_3$, partial), δ 206.2 (CO$_{Lev}$), 171.8 (CO$_{2Lev}$), 159.4 (C$_{IVArPMB}$), 143.3, 138.1 (2C, C$_{IVAr}$), 130.0-

119.4 (13C, 12C$_{Ar}$, C$_{IVArPMB}$), 113.8 (2C, C$_{ArPMB}$), 93.9 (C-1), 79.2 (C-4), 76.9 (C-3), 75.6 (C$_{Bn}$), 71.7 (C$_{PMB}$), 70.4 (C-5), 67.8 (C-2), 55.3 (CH$_{3PMB}$), 38.0 (COCH$_{2Lev}$), 29.9 (CH$_{3Lev}$), 28.0 (CO$_2$CH$_{2Lev}$), 18.0 (C-6).

Allyl (benzyl 2,3-di-O-benzyl-β-D-galactopyranosyluronate)-(1→3)-4,6-di-O-benzyl-2-deoxy-2-trichloroacetamido-β-D-galactopyranoside (242)

TEMPO (171 mg, 1.10 mmol) and BAIB (4.41 g, 13.69 mmol) were added to a solution of diol 241 (4.86 g, 5.48 mmol) in DCM/H$_2$O (2:1, 99 mL) vigorously stirred at rt. After 1.5 h, the reaction was quenched by addition of a 10% aq. NaHSO$_3$ solution. The biphasic mixture was diluted with DCM, and the layers were separated. The aq. phase was acidified with a 10% aq. HCl solution and re-extracted twice with DCM. The combined organic extracts were washed with brine, dried by passing through a phase separator filter and concentrated. Benzyl bromide (2.4 mL, 21.9 mmol, 4.0 equiv.) and KHCO$_3$ (2.12 g, 21.9 mmol, 4.0 equiv.) were added to the crude intermediate in dry DMF (82 mL) and the reaction mixture was stirred under an Ar atmosphere for 16 h. The reaction mixture was diluted with water and EtOAc. The layers were separated and the organic phase was washed with brine, dried over anhyd. Na$_2$SO$_4$, filtered and evaporated. The residue was purified by flash chromatography (Tol/EtOAc 9:1 to 85:15) to give the benzyl uronate 242 (4.25 g, 78%) as a white solid.

$^1$H NMR (CDCl$_3$), δ 7.44-7.24 (m, 25H, H$_{Ar}$), 6.86 (d, 1H, J$_{NH,2}$=6.7 Hz, NH), 5.88 (m, 1H, CH=$_{All}$), 5.27 (m, 1H, J$_{trans}$=17.3 Hz, J$_{gem}$=1.5 Hz, =CH$_{2All}$), 5.26 (bs, 2H, H$_{CO2Bn}$), 5.18 (m, 1H, J$_{cis}$=10.4 Hz, =CH$_{2All}$), 5.05 (d, 1H, J$_{1,2}$=8.3 Hz, H-1$_B$), 5.01 (d, 1H, J=11.8 Hz, H$_{Bn}$), 4.79 (d, 1H, J=11.6 Hz, H$_{Bn}$), 4.74 (d$_{po}$, 1H, J=11.9 Hz, H$_{Bn}$), 4.73 (bs$_o$, 2H, H$_{Bn}$), 4.71 (d$_{po}$, 1H, J=11.9 Hz, H$_{Bn}$), 4.68 (dd$_{po}$, 1H, J$_{2,3}$=11.1 Hz, J$_{3,4}$=3.1 Hz, H-3$_B$), 4.52 (d$_{po}$, 1H, J=11.9 Hz, H$_{Bn}$), 4.49 (d$_{po}$, 1H, J$_{1,2}$=7.7 Hz, H-1$_A$), 4.46 (d, 1H, J=11.9 Hz, H$_{Bn}$), 4.39-4.33 (m, 2H, H$_{All}$, H-4$_A$), 4.25 (d, 1H, H-4$_B$), 4.12-4.05 (m, 2H, H$_{All}$, H-5$_A$), 3.76-3.67 (m, 2H, H-2$_B$, H-5$_B$), 3.67-3.61 (m, 2H, H-2$_A$, H-6a$_B$), 3.53 (dd$_{po}$, 1H, J$_{5,6b}$ 5.9 Hz, J$_{6a,6b}$=10.9 Hz, H-6b$_B$), 3.50 (dd$_{po}$, 1H, J$_{2,3}$=9.2 Hz, J$_{3,4}$=3.4 Hz, H-3$_A$), 2.32 (bs, 1H, OH-4$_A$).

$^{13}$C NMR (CDCl$_3$) partial, δ 167.3 (C-6$_A$), 162.1 (NHCO), 103.7 (C-1$_A$), 97.5 (C-1$_B$), 92.2 (CCl$_3$), 67.1 (C$_{CO2Bn}$).

HRMS (ESI$^+$): m/z 1012.2621 (calcd for C$_{52}$H$_{54}$Cl$_3$NO$_{12}$Na [M+Na]$^+$: m/z 1012.2609).

(Benzyl 2,3-di-O-benzyl-4-O-levulinoyl-β-D-galactopyranosyluronate)-(1→3)-4,6-di-O-benzyl-2-deoxy-2-trichloroacetamido-α-D-galactopyranosyl trichloroacetimidate (246)

Levulinic acid (1.03 mL, 10.09 mmol), DCC (1.87 g, 9.08 mmol) and DMAP (123 mg, 1.01 mmol,) were added to a solution of uronate 242 (5.00 g, 5.04 mmol) in anhyd. DCM (50 mL). The solution was stirred under an Ar atmosphere for 16 h. The reaction mixture was filtered through a pad of Celite®, diluted with DCM and washed successively with a 10% aq. HCl solution, a satd. aq. NaHCO$_3$ solution and brine, dried by passing through a phase separator filter and concentrated. The residue was purified by flash chromatography (Tol/EtOAc 9:1 to 85:15) to give the fully protected disaccharide 244 (4.99 g, 91%) as a light yellow solid.

1,5-Cyclooctadienebis(methyldiphenylphosphine)-iridium hexafluorophosphate (194 mg, 230 μmol) was dissolved in anhyd. THF (60 mL). Hydrogen was bubbled through the solution for 15 min, and the resulting yellow solution was concentrated to dryness. The residue was taken up in anhyd. THF (92 mL), and a solution of the fully protected disaccharide 244 (4.99 g, 4.58 mmol) in anhyd. THF (92 mL) was added. The mixture was stirred for 2 h at rt under an Ar atmosphere. A solution of iodine (2.33 g, 9.16 mmol) in THF/H$_2$O (4:1, 110 mL,) was added, and stirring went on for 2 h at rt. The reaction was quenched by the addition of a freshly prepared solution of 10% aq. sodium bisulfite. The mixture was concentrated to ⅓ volume under reduced pressure and the aq. phase was extracted three times with DCM. The combined organic layers were washed with brine, dried by passing through a phase separator filter and evaporated to dryness. The resulting oil was purified by flash chromatography (Tol/EtOAc 7:3) to give the corresponding hemiacetal 245 (4.80 g, qqtive) in a 6.7:1 α/β ratio as a light yellow foam.

Trichloroacetonitrile (193 μL, 1.92 mmol) and DBU (17 μL, 0.12 mmol) were successively added to a solution of the resulting hemiacetal (245, 403 mg, 380 μmol) in anhyd. DCM (7.7 mL). The mixture was stirred for 30 min at rt under an Ar atmosphere. Following concentration to ⅓ volume (reduced pressure, rt) the reaction mixture was directly purified by flash chromatography (Chex/EtOAc 7:3+1% Et$_3$N) to give trichloroacetimidate 246 (412 mg, 91%) in a 12:1 α/β ratio as a white foam. The α isomer had:

$^1$H NMR (CDCl$_3$), δ 8.74 (s, 1H, =NH), 7.44-7.22 (m, 25H, H$_{Ar}$), 6.75 (d, 1H, J$_{NH,2}$=8.7 Hz, NH), 6.55 (d, 1H, J$_{1,2}$=3.6 Hz, H-1$_B$), 5.85 (bdd, 1H, H-4$_A$), 5.20 (d, 1H, J=11.8 Hz, H$_{CO2Bn}$), 5.16 (d, 1H, H$_{CO2Bn}$), 5.12 (d, 1H, J=11.8 Hz, H$_{Bn}$), 4.96 (ddd, 1H, J$_{2,3}$=11.1 Hz, H-2$_B$), 4.90 (d, 1H, J=12.2 Hz, H$_{Bn}$), 4.75-4.68 (m, 4H, 3H$_{Bn}$, H-1$_A$), 4.60 (bd, 1H, H-4$_B$), 4.50-4.46 (m, 2H, H$_{Bn}$), 4.42 (d, 1H, J=11.7 Hz, H$_{Bn}$), 4.27 (d, 1H, J$_{4,5}$=1.2 Hz, H-5$_A$), 4.22 (t, 1H, J$_{5,6a}$=J$_{5,6b}$=6.4 Hz, H-5$_B$), 4.15 (dd, 1H, J$_{2,3}$=11.0 Hz, J$_{3,4}$=2.7 Hz, H-3$_B$), 3.65-3.60 (m, 4H, H-6a$_B$, H-6b$_B$, H-2$_A$, H-3$_A$), 2.57-2.37 (m, 4H, CH$_{2Lev}$), 1.99 (s, 3H, CH$_{3Lev}$).

$^{13}$C NMR (CDCl$_3$) partial, δ 205.7 (CO$_{Lev}$), 171.2 (CO$_{2Lev}$), 165.9 (C-6$_A$), 161.9 (NHCO), 160.2 (C=NH), 104.5 (C-1$_A$), 95.3 (C-1$_B$), 92.3 (CCl$_{3C(O)NH}$), 91.0 (CCl$_{3OC(NH)}$), 67.7 (C$_{CO2Bn}$), 37.8 (CH$_{2Lev}$), 29.5 (CH$_{3Lev}$), 27.9 (CH$_{2Lev}$).

Benzyl 2,3-di-O-benzyl-4-O-levulinoyl-β-D-galactopyranosyluronate-(1→3)-4,6-di-O-benzyl-2-deoxy-2-trichloroacetamido-α/β-D-galactopyranosyl N-phenyltrifluoroacetimidate (247)

Hemiacetal 245 obtained from acceptor 242 as described above (5.67 g, 5.40 mmol) was dissolved in acetone (59 mL). N-(phenyl)trifluoroacetimidoyl chloride (2.24 g, 10.8 mmol) and Cs$_2$CO$_3$ (1.94 g, 5.94 mmol) were added and the mixture was stirred for 1.5 h at rt. The reaction mixture was filtered and the filtrate was concentrated. The residue was purified by flash chromatography (Chex/EtOAc 8:2 to 7:3+1% Et$_3$N) to give donor 247 (5.38 g, 89%) in a 13:1 α/β ratio as a white foam.

$^1$H NMR (CDCl$_3$), δ 7.43-7.22 (m, 27H, H$_{Ar}$), 7.10 (m, 1H, H$_{Ar}$), 6.76 (d, 2H, J=7.6 Hz, H$_{Ar}$), 6.72 (d, 1H, J$_{NH,2}$=8.2 Hz, NH-2$_B$), 6.52 (bs, 1H, H-1$_B$), 5.87 (dd, 1H, J$_{3,4}$=2.8 Hz, J$_{4,5}$=1.2 Hz, H-4$_A$), 5.23 (d, 1H, J=11.8 Hz, H$_{CO2Bn}$), 5.18 (d, 1H, H$_{CO2Bn}$), 5.07 (d, 1H, J=11.6 Hz, H$_{Bn}$), 4.89 (d, 1H, J=12.1 Hz, H$_{Bn}$), 4.84 (m, 1H, H-2$_B$), 4.75 (d, 1H, J=11.0 Hz, H$_{Bn}$), 4.73 (d$_{po}$, 1H, J=12.6 Hz, H$_{Bn}$), 4.71 (bs$_o$, 1H, H$_{Bn}$), 4.69 (d, 1H, J$_{1,2}$=6.0 Hz, H-1$_A$), 4.55 (bd, 1H, H-4$_B$), 4.52 (d, 1H, J=11.7 Hz, H$_{Bn}$), 4.50 (d, 1H, J=11.0 Hz, H$_{Bn}$), 4.46 (d, 1H, J=11.7 Hz, H$_{Bn}$), 4.29 (d, 1H, H-5$_A$), 4.18-4.12

(m, 2H, H-5$_B$, H-3$_B$), 3.68-3.59 (m, 3H, H-6a$_B$, H-2$_A$, H-3$_A$), 3.54 (dd, 1H, J$_{5,6b}$=6.3 Hz, J$_{6a,6b}$=9.8 Hz, H-6b$_B$), 2.61-2.39 (m, 4H, CH$_{2Lev}$), 2.00 (s, 3H, CH$_{3Lev}$).

$^{13}$C NMR (CDCl$_3$), δ 205.7 (CO$_{Lev}$), 171.3 (CO$_{2Lev}$), 165.9 (C-6$_A$), 162.0 (NHCO), 143.1, 138.7, 138.1, 138.0, 137.3, 135.0 (6C, C$_{IVAr}$), 129.0-119.2 (30C, C$_{Ar}$), 104.4 (C-1$_A$), 94.2 (C-1$_B$), 92.3 (CCl$_3$), 78.6 (C-2$_A$), 77.3, 77.2 (2C, C-3$_B$, C-3$_A$), 75.8 (C-4$_B$), 75.0, 74.8, 73.4 (3C, C$_{Bn}$), 72.5 (C-5$_A$), 72.4 (C-5$_B$), 72.2 (C$_{Bn}$), 68.9 (C-6$_B$), 67.7 (C$_{CO2Bn}$), 67.5 (C-4$_A$), 50.7 (C-2$_B$), 37.8 (CH$_{2Lev}$), 29.5 (CH$_{3Lev}$), 27.9 (CH$_{2Lev}$).

Allyl (3,4-di-O-benzyl-2-O-levulinoyl-α-L-rhamnopyranosyl)-(1→4)-(benzyl 2,3-di-O-benzyl-β-D-galactopyranosyluronate)-(1→3)-4,6-di-O-benzyl-2-deoxy-2-trichloroacetamido-β-D-galactopyranoside (277)

A mixture of acceptor 242 (7.26 g, 7.32 mmol), known 3,4-di-O-benzyl-2-O-levulinoyl-α-L-rhamnopyranosyl trichloroacetimidate[28] (5.59 g, 9.52 mmol), and powdered MS 4 (10.9 g) in anhyd. toluene (146 mL) was stirred at rt under an Ar atmosphere for 1 h. The reaction mixture was cooled to −10° C. and TMSOTf (66 μL, 370 μmol) was added. After 20 min, the reaction was quenched with Et$_3$N. Solids were filtered and the filtrate was concentrated to dryness. The residue was purified by flash chromatography (Tol/EtOAc 9:1 to 8:2) to give trisaccharide 277 (9.19 g, 89%) as a white foam.

$^1$H NMR (CDCl$_3$), δ 7.43-7.10 (m, 35H, H$_{Ar}$), 6.90 (d, 1H, J$_{NH,2}$=6.7 Hz, NH), 5.89 (m, 1H, CH=$_{All}$), 5.46 (dd, 1H, J$_{1,2}$=1.9 Hz, J$_{3,4}$=3.0 Hz, H-2$_D$), 5.28 (m$_o$, 1H, J$_{trans}$=17.2 Hz, J$_{gem}$=1.5 Hz, =CH$_{2All}$), 5.27 (d$_o$, 1H, H$_{CO2Bn}$), 5.19 (d$_o$, 1H, H-1$_D$), 5.18 (m$_o$, 1H, J$_{cis}$=10.4 Hz, =CH$_{2All}$), 5.15 (d, 1H, J=12.2 Hz, H$_{CO2Bn}$), 5.04 (d, 1H, J$_{1,2}$=8.3 Hz, H-1$_B$), 4.96 (d, 1H, J=11.7 Hz, H$_{Bn}$), 4.84 (d, 1H, J=11.2 Hz, H$_{Bn}$), 4.82 (s, 2H, H$_{Bn}$), 4.76 (s, 2H, H$_{Bn}$), 4.67 (dd$_{po}$, 1H, J$_{2,3}$=10.9 Hz, J$_{3,4}$=3.3 Hz, H-3$_B$), 4.66 (d$_o$, 1H, J=10.9 Hz, H$_{Bn}$), 4.58 (d, 1H, J=11.1 Hz, H$_B$), 4.53 (d, 1H, J$_{1,2}$=7.6 Hz, H-1$_A$), 4.49-4.44 (m, 2H, H$_{Bn}$, H-4$_A$), 4.42 (d, 1H, J=12.0 Hz, H$_{Bn}$), 4.37 (m$_{po}$, 1H, H$_{All}$), 4.33 (d$_{po}$, 1H, J 10.7 Hz, H$_{Bn}$), 4.24 (bd, 1H, H-4$_B$), 4.13-4.07 (m, 2H, H$_{All}$, H-5$_A$), 3.95 (d, 1H, J 10.8 Hz, H$_{Bn}$), 3.77 (dq$_{po}$, 1H, J$_{4,5}$=9.8 Hz, H-5$_D$), 3.77-3.67 (m, 4H, H-3$_D$, H-2$_B$, H-2$_A$, H-5$_B$), 3.60 (dd, 1H, J$_{5,6a}$=6.6 Hz, J$_{6a,6b}$ 10.0 Hz, H-6a$_B$), 3.52 (dd, 1H, J$_{2,3}$=9.7 Hz, J$_{3,4}$=2.8 Hz, H-3$_A$), 3.38-3.32 (m, 2H, H-6b$_B$, H-4$_D$), 2.71-2.61 (m, 4H, CH$_{2Lev}$), 2.16 (s, 3H, CH$_{3Lev}$), 1.33 (d, 3H, J$_{5,6}$=6.2 Hz, H-6$_D$).

$^{13}$C NMR (CDCl$_3$) partial, δ 206.1 (CO$_{Lev}$), 171.5 (CO$_{2Lev}$), 167.0 (C-6$_A$), 162.2 (NHCO), 103.9 (C-1$_A$, $^1$J$_{CH}$=163.6 Hz), 98.9 (C-1$_D$, $^1$J$_{CH}$=170.6 Hz), 97.5 (C-1$_B$, J$_{CH}$=163.2 Hz), 92.3 (CCl$_3$), 67.4 (C$_{CO2Bn}$), 57.0 (C-2$_B$), 38.1 (COCH$_{2Lev}$), 29.8 (CH$_{3Lev}$), 28.2 (CO$_2$CH$_{2Lev}$).

HRMS (ESI$^+$): m/z 1436.4559 (calcd for C$_{77}$H$_{82}$Cl$_3$NO$_{18}$Na [M+Na]$^+$: m/z 1436.4495).

(3,4-Di-O-benzyl-2-O-levulinoyl-α-L-rhamnopyranosyl)-(1→4)-(benzyl 2,3-di-O-benzyl-β-D-galactopyranosyluronate)-(1→3)-4,6-di-O-benzyl-2-deoxy-2-trichloroacetamido-α/β-D-galactopyranosyl N-phenyltrifluoroacetimidate (283)

1,5-Cyclooctadienebis(methyldiphenylphosphine)-iridium hexafluorophosphate (91 mg, 0.11 mmol) was dissolved in anhyd. THF (43 mL) and hydrogen was bubbled through the solution for 15 min (H-cube, full H$_2$ mode). The resulting yellow solution was evaporated to dryness. The residue was taken up in anhyd. THF (43 mL) and poured to a solution of allyl glycoside 277 (3.05 g, 2.15 mmol) in anhyd. THF (43 mL). The mixture was stirred under Ar at rt for 2 h. A solution of iodine (1.09 g, 4.31 mmol) in THF/H$_2$O (4:1, 52 mL) was added, and the mixture was stirred for 1.5 h at rt. The reaction was quenched with 10% aq. sodium bisulfite. The mixture was concentrated to ⅓ volume and the aq. phase was extracted twice with EtOAc. The organic layers were pooled, washed with brine, dried over anhyd. Na$_2$SO$_4$, filtered and concentrated to dryness. The residue was purified by flash chromatography (Tol/EtOAc 7:3) to give the corresponding hemiacetal 281 (2.84 g, 96%) as a light yellow foam. (α/β, 7.5:1).

This hemiacetal (2.74 g, 2.0 mmol) was dissolved in acetone (20 mL). N-(phenyl)trifluoroacetimidoyl chloride (827 mg, 3.98 mmol) followed by Cs$_2$CO$_3$ (714 mg, 2.19 mmol) were added to the solution. The mixture was stirred for 2 h at rt. More Cs$_2$CO$_3$ (649 mg, 2.0 mmol) was added. After 1 h, the reaction mixture was filtered and concentrated. The residue was purified by flash chromatography (Chex/EtOAc 65:35 to 6:4+1% Et$_3$N) to give a 7:1 α/β mixture of N-phenyltrifluoroacetimidate 283 (3.00 g, 97%) as a light yellow foam.

$^1$H NMR (CDCl$_3$), δ 7.63-7.05 (m, 38H, H$_{Ar}$), 6.74 (d, 2H, J=7.5 Hz, H$_{Ar}$), 6.68 (d, 1H, J$_{NH,2}$=8.3 Hz, NH), 6.50 (bs, 1H, H-1$_B$), 5.38 (dd, 1H, J$_{1,2}$=2.0 Hz, J$_{2,3}$=3.1 Hz, H-2$_D$), 5.26 (d, 1H, J=12.0 Hz, H$_{CO2Bn}$), 5.10 (d$_o$, 1H, H-1$_D$), 5.11 (d$_{po}$, 1H, H$_{CO2Bn}$), 4.98 (d, 1H, J=11.6 Hz, H$_{Bn}$), 4.91 (d, 1H, J=12.2 Hz, H$_{Bn}$), 4.86-4.71 (m, 5H, H-2$_B$, 4H$_{Bn}$), 4.64 (d, 1H, J$_{1,2}$=7.5 Hz, H-1$_A$), 4.55 (d, 1H, J=11.1 Hz, H$_{Bn}$), 4.53 (d, 1H, J=11.6 Hz, H$_{Bn}$), 4.48 (d$_{po}$, 1H, J$_{3,4}$=3.2 Hz, H-4$_B$), 4.47 (d$_o$, 1H, J=11.7 Hz, H$_{Bn}$), 4.45 (bd$_o$, 1H, H-4$_A$), 4.41 (d, 1H, J=12.1 Hz, H$_{Bn}$), 4.23 (d, 1H, J=10.6 Hz, H$_{Bn}$), 4.16 (d, 1H, 1$_{4,5}$=0.8 Hz, H-5$_A$), 4.12-4.05 (m, 2H, H-5$_B$, H-3$_B$), 3.81 (d, 1H, J=10.7 Hz, H$_{Bn}$), 3.77 (dd$_{po}$, 1H, J$_{2,3}$=9.5 Hz, H-2$_A$), 3.73 (dq$_{po}$, 1H, 1$_{4,5}$=9.6 Hz, H-5$_D$), 3.63 (dd, 1H, J$_{2,3}$=3.2 Hz, J$_{3,4}$=9.4 Hz, H-3$_D$), 3.59 (dd$_{po}$, 1H, 1$_{3,4}$=2.7 Hz, H-3$_A$), 3.56 (dd$_{po}$, 1H, J$_{5,6a}$=6.7 Hz, J$_{6a,6b}$=10.3 Hz, H-6a$_B$), 3.36 (dd, 1H, J$_{5,6b}$=5.2 Hz, H-6b$_B$), 3.31 (pt, 1H, H-4$_D$), 2.71-2.59 (m, 4H, CH$_{2Lev}$), 2.15 (s, 3H, CH$_{3Lev}$), 1.30 (d, 3H, J$_{5,6}$=6.2 Hz, H-6$_D$).

$^{13}$C NMR (CDCl$_3$), δ 206.1 (CO$_{Lev}$), 171.4 (CO$_{2Lev}$), 166.8 (C-6$_A$), 161.9 (NHCO), 104.9 (C-1$_A$), 99.0 (C-1$_D$), 94.0 (C-1$_B$), 92.3 (CCl$_3$), 67.6 (C$_{CO2Bn}$), 38.1 (COCH$_{2Lev}$), 29.8 (CH$_{3Lev}$), 28.2 (CO$_2$CH$_{2Lev}$).

Allyl (4-O-benzyl-3-O-para-methoxybenzyl-2-O-levulinoyl-α-L-rhamnopyranosyl)-(1→2)-(3,4-di-O-benzyl-α-L-rhamnopyranosyl)-(1→4)-(benzyl 2,3-di-O-benzyl-β-D-galactopyranosyluronate)-(1→3)-4,6-di-O-benzyl-2-deoxy-2-trichloroacetamido-β-D-galactopyranoside (XX)

To a solution of the fully protected trisaccharide 277 (8.84 g, 6.24 mmol) in anhyd. pyridine (52 mL) stirred at 0° C. under an Ar atmosphere was added dropwise AcOH (35 mL) followed by hydrazine monohydrate (1.52 mL, 31.2 mmol). The reaction mixture was stirred for 1 h allowing the cooling bath to reach rt. Following addition of DCM and water, the two layers were separated and the aq. one was re-extracted twice with DCM. The combined organic extracts were washed with brine, dried by passing through a phase separator filter and volatiles were evaporated. The residue was purified by flash chromatography (Chex/EtOAc 75:25 to 7:3) to give the corresponding acceptor (7.56 g, 92%) as a white foam.

A mixture of this acceptor (7.03 g, 5.34 mmol), trichloroacetimidate donor 119 (3.96 g, 6.42 mmol), and powdered MS 4 (10.6 g) in anhyd. toluene (134 mL) was stirred at rt under an Ar atmosphere for 1 h. The reaction mixture was cooled to −10° C. and TMSOTf (48 µL, 267 µmol) was added. After 30 min, the reaction was quenched with Et$_3$N. Solids were filtered and the filtrate was concentrated to dryness. The residue was purified by flash chromatography (Tol/EtOAc 95:5 to 8:2) to give tetrasaccharide 279 (8.66 g, 91%) as a white foam.

$^1$H NMR (CDCl$_3$), δ 7.45-7.11 (m, 42H, H$_{Ar}$), 6.89-6.84 (m, 3H, 2H$_{ArPMB}$, NH), 5.88 (m, 1H, CH=$_{All}$), 5.49 (dd, 1H, J$_{1,2}$=1.8 Hz, H-2$_C$), 5.31 (d, 1H, J$_{1,2}$=1.6 Hz, 14-1$_D$), 5.26 (d$_{po}$, 1H, J=12.1 Hz, H$_{CO2Bn}$), 5.25 (m$_{po}$, 1H, J$_{trans}$ 17.2 Hz, J$_{gem}$=1.5 Hz, =CH$_{2All}$), 5.17 (m, 1H, J$_{cis}$=10.4 Hz, =CH$_{2All}$), 5.13 (d, 1H, H$_{CO2Bn}$), 5.03 (d, 1H, J$_{1,2}$=8.5 Hz, H-1$_B$), 4.97 (d$_{po}$, 1H, J=11.6 Hz, H$_{Bn}$), 4.96 (bs$_o$, 1H, H-1$_C$), 4.90 (d, 1H, J=10.9 Hz, H$_{Bn}$), 4.82 (d, 1H, J=11.0 Hz, H$_{Bn}$), 4.79 (d$_{po}$, 1H, J=12.4 Hz, H$_{Bn}$), 4.77 (bs$_o$, 2H, H$_{Bn}$), 4.68-4.61 (m, 6H, 5H$_{Bn}$, H-3$_B$), 4.58 (d, 1H, J=11.7 Hz, H$_{Bn}$), 4.49 (d, 1H, J$_{1,2}$=7.6 Hz, H-1$_A$), 4.47 (d, 1H, J=11.9 Hz, H$_{Bn}$), 4.43 (d, 1H, J=12.1 Hz, H$_{Bn}$), 4.40 (bd, 1H, H-4$_A$), 4.36 (m, 1H, H$_{All}$), 4.25 (d, 1H, J$_{3,4}$=3.0 Hz, H-4$_B$), 4.22 (d, 1H, J=11.4 Hz, H$_{Bn}$), 4.14 (d, 1H, J=11.4 Hz, H$_{Bn}$), 4.12-4.04 (m, 3H, H$_{All}$, H-2$_D$), 4.04 (d, 1H, J$_{4,5}$=0.6 Hz, H-5$_A$), 3.87 (dd, 1H, J$_{2,3}$=3.2 Hz, J$_{3,4}$=9.1 Hz, H-3$_C$), 3.83 (dq, 1H, 1$_{4,5}$=9.4 Hz, J$_{5,6}$=6.2 Hz, H-5$_C$), 3.78 (s, 3H, CH$_{3PMB}$), 3.73-3.63 (m, 5H, H-5$_D$, H-3$_D$, H-2$_B$, H-2$_A$, H-5$_B$), 3.61 (dd, 1H, J$_{5,6a}$=6.6 Hz, J$_{6a,6b}$=10.0 Hz, H-6a$_B$), 3.47 (dd$_{po}$, 1H, J$_{2,3}$=9.7 Hz, J$_{3,4}$=2.7 Hz, H-3$_A$), 3.45 (pt$_{po}$, 1H, H-4$_C$), 3.39 (dd, 1H, J$_{5,6b}$=5.5 Hz, H-6b$_B$), 3.37 (pt, 1H, H-4$_D$), 2.79-2.66 (m, 4H, CH$_{2Lev}$), 2.19 (s, 3H, CH$_{3Lev}$), 1.32 (d, 3H, J$_{5,6}$=6.2 Hz, H-6$_D$), 1.22 (d, 3H, H-6$_C$).

$^{13}$C NMR (CDCl$_3$) partial, δ 206.1 (CO$_{Lev}$), 171.7 (CO$_{2Lev}$), 167.0 (C-6$_A$), 162.1 (NHCO), 159.4 (C$_{IVArPMP}$), 113.9 (2C, C$_{ArPMB}$), 103.9 (C-1$_A$), 100.7 (C-1$_C$), 100.2 (C-1$_D$), 97.5 (C-1$_B$), 92.3 (CCl$_3$), 67.4 (C$_{CO2Bn}$), 55.2 (CH$_{3PMB}$), 38.2 (COCH$_{2Lev}$), 29.8 (CH$_{3Lev}$), 28.3 (CO$_2$CH$_{2Lev}$).

HRMS (ESI$^+$): m/z 1792.6085 (calcd for C$_{98}$H$_{106}$Cl$_3$NO$_{23}$Na [M+Na]$^+$: m/z 1792.6119).

(4-O-Benzyl-3-O-para-methoxybenzyl-2-O-levulinoyl-α-L-rhamnopyranosyl)-(1→2)-(3,4-di-O-benzyl-α-L-rhamnopyranosyl)-(1→4)-(benzyl 2,3-di-O-benzyl-β-D-galactopyranosyluronate)-(1→3)-4,6-di-O-benzyl-2-deoxy-2-trichloroacetamido-α/β-D-galactopyranosyl N-phenyltrifluoroacetimidate (284)

Cyclooctadienebis(methyldiphenylphosphine)-iridium hexafluorophosphate (97 mg, 0.11 mmol) was dissolved in anhyd. THF (46 mL) and hydrogen was bubbled through the solution for 15 min (H-cube, full H$_2$ mode). The resulting yellow solution was evaporated to dryness. The residue was taken up in anhyd. THF (46 mL) and poured to a solution of the allyl glycoside 279 (4.05 g, 2.29 mmol) in anhyd. THF (46 mL). The mixture was stirred under Ar at rt for 3.5 h. A solution of iodine (1.16 g, 4.57 mmol) in THF/H$_2$O (4:1, 55 mL) was added, and the mixture was stirred for 1.5 h at rt. The reaction was quenched with 10% aq. sodium bisulfite. The mixture was concentrated to ⅓ volume and the aq. phase was extracted twice times with EtOAc. The organic layers were pooled, washed with brine, dried over anhyd. Na$_2$SO$_4$, filtered and concentrated to dryness. The residue was purified by flash chromatography (Tol/EtOAc 75:25 to 6:4) to give the coresponding hemiacetal (3.85 g, 97%) as a light yellow solid (α/β, 5:1).

This hemiacetal (3.73 g, 2.15 mmol) was dissolved in acetone (43 mL). N-(phenyl)trifluoroacetimidoyl chloride (893 mg, 4.30 mmol) followed by Cs$_2$CO$_3$ (1.40 g, 4.30 mmol) were added to the solution. The mixture was stirred for 2 h at rt. The reaction mixture was filtered and concentrated. The residue was purified by flash chromatography (Chex/EtOAc 75:25 to 6:4+1% Et$_3$N) to give a 5:1 α/β mixture of N-phenyltrifluoroacetimidate 284 (3.66 g, 89%) as a white foam.

$^1$H NMR (CDCl$_3$), δ 7.46-7.05 (m, 45H, H$_{Ar}$), 6.87-6.82 (m, 2H, H$_{ArPMB}$), 6.77-6.72 (m, 2H, H$_{Ar}$), 6.67 (d, 1H, J$_{NH,2}$=8.3 Hz, NH), 6.50 (bs, 1H, H-1$_B$), 5.47 (dd, 1H, J$_{1,2}$=1.9 Hz, J$_{2,3}$=3.1 Hz, H-2$_C$), 5.27 (s$_o$, 1H, H-1$_D$), 5.26 (d, 1H, J=12.1 Hz, H$_{CO2Bn}$), 5.11 (d, 1H, H$_{CO2BN}$), 5.03 (d, 1H, J=11.4 Hz, H$_{Bn}$), 4.94-4.85 (m, 3H, 2H$_{Bn}$, H-2$_B$), 4.84-4.72 (m, 4H, 3H$_{Bn}$, H-1$_C$), 4.65 (2d$_o$, 2H, J=11.5 Hz, H$_{Bn}$), 4.63-4.55 (m, 4H, 3H$_{Bn}$, H-1$_A$), 4.51 (bd, 1H, J$_{3,4}$=2.4 Hz, H-4$_B$), 4.50-4.42 (m, 4H, H$_{Bn}$), 4.41 (hd$_{po}$, 1H, J$_{3,4}$=3.6 Hz, H-4$_A$), 4.13-4.06 (m, 4H, H$_{Bn}$, H-5$_B$, H-5$_A$, H-3$_B$), 4.04 (d, 1H, J=11.6 Hz, H$_{Bn}$), 3.94-3.89 (m, 2H, H-2$_D$, H-3$_C$), 3.81 (dq, 1H, J$_{4,5}$=9.4 Hz, J$_{5,6}$=6.3 Hz, H-5$_C$), 3.77 (s, 3H, CH$_{3PMB}$), 3.73 (dd, 1H, J$_{1,2}$=7.5 Hz, J$_{2,3}$=10.0 Hz, H-2$_A$), 3.67 (dq, 1H, J$_{4,5}$=9.4 Hz, J$_{5,6}$=6.2 Hz, H-5$_D$), 3.62-3.52 (m, 3H, H-3$_D$, H-6a$_B$, H-3$_A$), 3.43-3.33 (m, 3H, H-4$_C$, H-4$_D$, H-6b$_B$), 2.77-2.67 (m, 4H, CH$_{2Lev}$), 2.19 (s, 3H, CH$_{3Lev}$), 1.29 (d, 3H, H-6$_D$), 1.20 (d, 3H, H-6$_C$).

$^{13}$C NMR (CDCl$_3$) partial, δ 206.1 (CO$_{Lev}$), 171.6 (CO$_{2Lev}$) 166.8 (C-6$_A$), 162.0 (NHCO), 159.2 (C$_{IVArPMB}$), 143.1 (C=NPh), 113.7 (2C, C$_{ArPMB}$), 105.0 (C-1$_A$), 100.1 (C-1$_D$), 99.2 (C-1$_C$), 94.3 (C-1$_B$), 92.3 (CCl$_3$), 67.5 (C$_{CO2Bn}$), 55.2 (CH$_{3PMB}$), 38.1, (COCH$_{2Lev}$), 29.8 (CH$_{3Lev}$), 28.2 (CO$_2$CH$_{2Lev}$).

Allyl (4-O-benzyl-3-O-para-methoxybenzyl-α-L-rhamnopyranosyl)-(1→2)-(3,4-di-O-benzyl-α-L-rhamnopyranosyl)-(1→4)-(benzyl 2,3-di-O-benzyl-β-D-galactopyranosylurortate)-(1→3)-4,6-di-O-benzyl-2-deoxy-2-trichloroacetamido-β-D-galactopyranoside (280)

AcOH (20 mL), followed by hydrazine monohydrate (443 µL, 9.12 mmol), was added dropwise to a solution of 279 (3.23 g, 1.82 mmol) in anhyd. pyridine (30 mL) stirred at 0° C. under an Ar atmosphere. The reaction mixture was stirred for 1 h allowing the cooling bath to reach it Following addition of DCM and water, the two layers were separated and the aq. one was re-extracted twice with DCM. The combined organic extracts were washed with brine, dried by filtration through a phase separator filter and volatiles were evaporated. The residue was purified by flash chromatography (Chex/EtOAc 75:25 to 65:35) to give alcohol 280 (2.87 g, 94%) as a white foam.

$^1$H NMR (CDCl$_3$), δ 7.42-7.10 (m, 42H, H$_{Ar}$), 6.91-6.87 (m, 2H, J=8.6 Hz, H$_{ArPMB}$), 6.86 (d, 1H, J$_{NH,2}$=6.8 Hz, NH), 5.88 (m, 1H, CH=$_{All}$), 5.31 (d, 1H, J$_{1,2}$=1.6 Hz, H-1$_D$), 5.26 (d$_{po}$, 1H, J=12.1 Hz, H$_{CO2Bn}$), 5.25 (m$_{po}$, 1H, J$_{trans}$=17.2 Hz, J$_{gem}$=1.5 Hz, =CH$_{2All}$), 5.17 (m, 1H, J$_{cis}$=10.4 Hz, =CH$_{2All}$), 5.13 (d, 1H, H$_{CO2Bn}$), 5.03 (d, 1H, J$_{1,2}$=8.5 Hz, H-1$_B$), 4.97 (d$_{po}$, 1H, J=11.6 Hz, H$_{Bn}$), 4.96 (bs$_o$, 1H, H-1$_C$), 4.90 (d, 1H, J=10.9 Hz, H$_{Bn}$), 4.82 (d, 1H, J=11.0 Hz, H$_{Bn}$), 4.79 (d$_{po}$, 1H, J=12.4 Hz, H$_{Bn}$), 4.77 (bs$_o$, 2H, H$_{Bn}$), 4.68-4.61 (m, 6H, 5H$_{Bn}$, H-3$_B$), 4.58 (d, 1H, J=11.7 Hz, H$_{Bn}$), 4.49 (d, 1H, 42=7.6 Hz, H-1$_A$), 4.47 (d, 1H, J=11.9 Hz, H$_{Bn}$), 4.43 (d, 1H, J=12.1 Hz, H$_{Bn}$), 4.40 (bd, 1H, H-4$_A$), 4.36 (m, 1H, H$_{All}$), 4.25 (d, 1H, J$_{3,4}$=3.0 Hz, H-4$_B$), 4.22 (d, 1H, J=11.4 Hz, H$_{Bn}$), 4.14 (d, 1H, J=11.4 Hz, H$_{Bn}$), 4.12-4.04 (m, 3H, H$_{All}$, H-2$_C$, H-2$_D$), 4.04 (d, 1H, J$_{4,5}$=0.6 Hz, H-5$_A$), 3.87 (dd, 1H, J$_{2,3}$=3.2 Hz, J$_{3,4}$=9.1 Hz, H-3$_C$), 3.83 (dq, 1H, J$_{4,5}$=9.4 Hz, H-5$_C$), 3.78 (s, 3H, CH$_{3PMB}$), 3.73-3.63 (m, 5H, H-5$_D$, H-3$_D$, H-2$_B$, H-2$_A$, H-5$_B$), 3.61 (dd, 1H, J$_{5,6a}$=6.6 Hz, J$_{6a,6b}$=10.0 Hz, H-6$_B$), 3.47 (dd$_{po}$, 1H, J$_{2,3}$=9.7 Hz, J$_{3,4}$=2.7 Hz, H-3$_A$), 3.45 (pt$_{po}$, 1H, J$_{3,4}$=9.3 Hz, J$_{4,5}$ 9.4 Hz, H-4$_C$), 3.39 (dd, 1H, J$_{5,6b}$=5.5 Hz, H-6b$_B$), 3.37 (pt, 1H, H-4$_D$), 2.39 (bs, 1H, OH-2$_C$), 1.32 (d, 3H, J$_{5,6}$=6.2 Hz, H-6$_D$), 1.22 (d, 1H, J$_{5,6}$=6.2 Hz, H-6$_C$).

$^{13}$C NMR (CDCl$_3$) partial, δ 167.0 (C-6$_A$), 162.1 (NHCO), 159.4 (C$_{IVArPMB}$), 113.9 (2C, C$_{ArPMB}$), 103.9 (C-1$_A$), 100.7 (C-1$_C$), 100.2 (C-1$_D$), 97.5 (C-1$_B$), 92.3 (CCl$_3$), 67.4 (C$_{CO2Bn}$), 55.2 (CH$_{3PMB}$). HRMS (ESI$^+$): m/z 1694.5691 (calcd for C$_{93}$H$_{100}$Cl$_3$NO$_{21}$Na [M+Na]$^+$: m/z 1694.5751).

Convergent Synthesis of Fully Protected Precursors to SF6, SF6a, and/or *E. coli* O147 O-Antigen Fragments Using the Building Blocks Shown in Table 1.

Selected Examples:

Protected pentasaccharide ABCDA (248). Taking advantage of the design of proper building blocks, the fully protected 248 is obtained in one single step in high yield, upon glycosylation of acceptor 169 with donor (Scheme 8).

Benzyl (benzyl 2,3-di-O-benzyl-4-O-levulinoyl-β-D-galactopyranosyluronate)-(1→3)-(4,6-di-O-benzyl-2-deoxy-2-trichloroacetamido-β-D-galactopyranosyl)-(1→2)-(4-O-benzyl-3-O-para-methoxybenzyl-α-L-rhamnopyranosyl)-(1→2)-(3,4-di-O-benzyl-α-L-rhamnopyranosyl)-(1→4)-(allyl 2,3-di-O-benzyl-β-D-galactopyranosid)uronate (248)

A mixture of trisaccharide acceptor 169 (2.15 g, 1.81 mmol), disaccharide donor 247 (2.65 g, 2.17 mmol) and freshly activated 4 powdered MS (5.4 g) in anhyd. DCM (36.2 mL) was stirred for 1 h at rt under an Ar atmosphere, then at −78° C. TMSOTf (16.4 µL, 91 µmol) was added and the reaction mixture was stirred at that temperature for 20 min. The reaction was quenched with Et$_3$N. The suspension was filtered and the filtrate was concentrated. The residue was purified by flash chromatography (Tol/EtOAc 95:5 to 85:5) to give pentasaccharide 248 (3.47 g, 86%) as a white foam.

$^1$H NMR (CDCl$_3$), δ 7.47-7.43 (m, 2H, H$_{Ar}$), 7.41-7.02 (m, 53H, H$_{Ar}$), 7.16 (m, 1H, H$_{Ar}$), 7.08 (m, 1H, H$_{Ar}$), 7.03 (d, 1H, J$_{NH,2}$=6.8 Hz, NH), 6.82 (d, 2H, J=8.7 Hz, H$_{ArPMB}$),

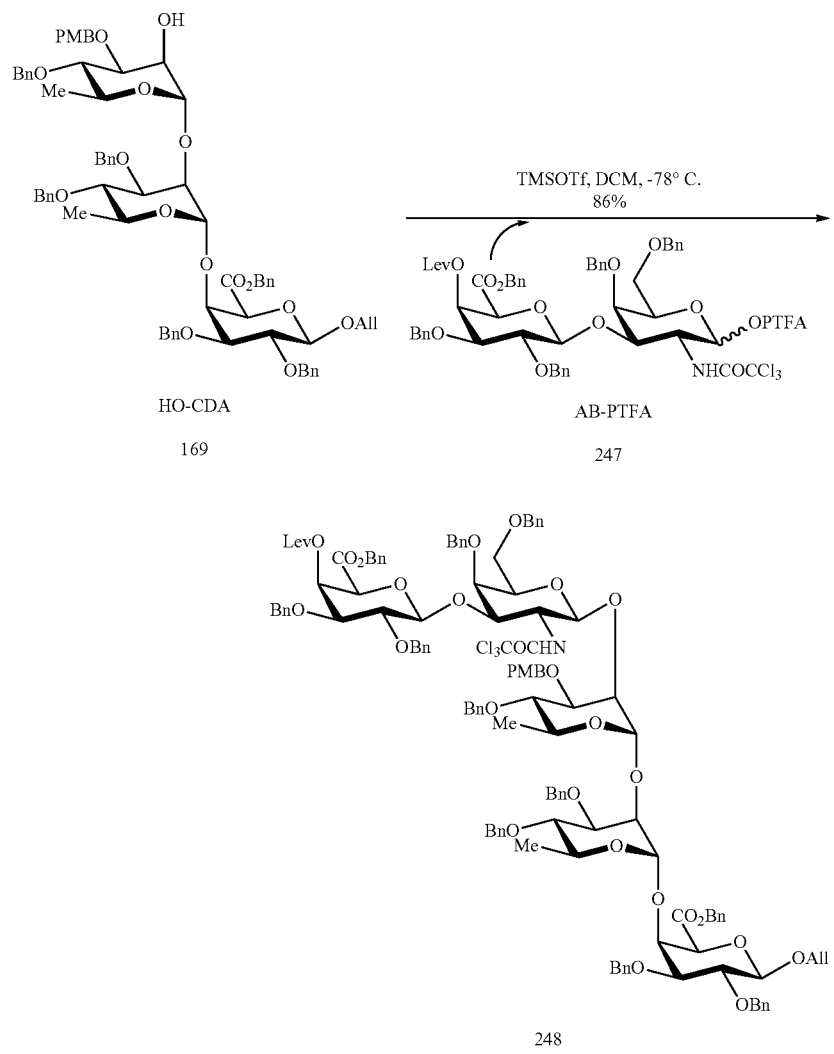

Scheme 8

5.98 (m, 1H, CH=$_{All}$), 5.82 (bd, 1H, H-4$_A$), 5.35 (m, 1H, J$_{trans}$=17.2 Hz, J$_{gem}$=1.6 Hz, CH$_{2All}$), 5.27 (d, 1H, J$_{1,2}$=1.4 Hz, H-1$_D$), 5.27-5.19 (m, 4H, H-1$_B$, =CH$_{2All}$, 2H$_{CO2Bn}$), 5.18 (d$_{po}$, 1H, J=11.9 Hz, H$_{CO2Bn}$), 5.10 (d$_{po}$, 1H, J=12.1 Hz, H$_{CO2Bn}$), 5.08 (d, 1H, J=11.4 Hz, H$_{Bn}$), 5.00 (d, 1H, J$_{1,2}$=1.2 Hz, H-1$_C$), 4.92 (d, 1H, J=10.9 Hz, H$_{Bn}$), 4.91 (d, 1H, J 10.9 Hz, H$_{Bn}$), 4.87 (d, 1H, J=11.7 Hz, H$_{Bn}$), 4.82 (d, 1H, J=11.1 Hz, H$_{Bn}$), 4.80-4.69 (m, 6H, 5H$_{Bn}$, H-3$_B$), 4.66-4.59 (m, 4H, H-1$_A$, 3H$_{Bn}$), 4.57-4.46 (m, 6H, 5H$_{Bn}$, H$_{All}$), 4.38-4.33 (m, 3H, H-1$_A$, H-4$_A$, H-4$_B$), 4.28 (d, 1H, J=11.8 Hz, H$_{Bn}$), 4.22 (d, 1H, J$_{4,5}$=1.0 Hz, H-5$_A$), 4.19 (d$_{po}$, 1H, J=11.7 Hz, H$_{Bn}$), 4.15 (m$_o$, 1H, H$_{All}$), 4.08 (pt, 1H, H-2$_C$), 4.01 (pt, 1H, H-2$_D$), 3.99 (s, 1H, H-5$_A$), 3.86 (dd$_{po}$, 1H, J$_{2,3}$=2.9 Hz, H-3$_C$), 3.85-3.78 (m, 2H, H-2$_B$, H-3$_D$), 3.78 (dq$_{pc}$, 1H, J$_{4,5}$=9.5 Hz, H-5$_C$), 3.71-3.61 (m, 6H, H-5$_D$, CH$_{3PMB}$, H-2$_A$, H-5$_B$), 3.59-3.52 (m, 3H, H-6a$_B$, H-2$_{A'}$, H-3$_A$), 3.49 (dd, 1H, J$_{2,3}$=9.8 Hz, J$_{3,4}$=2.8 Hz, H-3$_{A'}$), 3.43 (pt, 1H, J$_{3,4}$=9.5 Hz, H-4$_C$), 3.38 (dd, 1H, J$_{5,6b}$=5.2 Hz, J$_{6a,6b}$=9.0 Hz, H-6b$_B$), 3.32 (pt, 1H, J$_{3,4}$=J$_{4,5}$=9.4 Hz, H-4$_D$), 2.59-2.41 (m, 4H, CH$_{2Lev}$), 2.00 (s, 3H, CH$_{3Lev}$), 1.28 (d, 3H, J$_{5,6}$=6.2 Hz, H-6$_D$), 1.20 (d, 3H, J$_{5,6}$=6.2 Hz, H-6$_C$).

$^{13}$C NMR (CDCl$_3$), δ 205.9 (CO$_{Lev}$), 171.3 (CO$_{2Lev}$), 167.3, 166.2 (2C, C-6$_A$, C-6$_{A'}$), 161.7 (NHCO), 113.7 (2C, C$_{ArPMB}$), 103.6 (C-1$_{A'}$, $^1$J$_{CH}$=163.2 Hz), 102.6 (C-1$_A$, $^1$J$_{CH}$=155.6 Hz), 101.2 (C-1$_D$, $^1$J$_{CH}$=176.2 Hz), 100.2 (C-1$_C$, $^1$J$_{CH}$=173.5 Hz), 98.9 (C-1$_B$, $^1$J$_{CH}$=162.4 Hz), 92.6 (CCl$_3$), 67.5, 67.3 (2C, C$_{CO2Bn}$), 55.1 (CH$_{3PMB}$), 37.9 (COCH$_{2Lev}$), 29.5 (CH$_{3Lev}$), 28.0 (CO$_2$CH$_{2Lev}$).

HRMS (ESI$^+$): m/z 2238.8015 (calcd for C$_{125}$H$_{132}$Cl$_3$NO$_{29}$Na [M+Na]$^+$: m/z 2238.7849).

Protected heptasaccharide DABCDAB (294). Taking advantage of the design of proper building blocks, the fully protected 294 is obtained in one single step in high yield, upon glycosylation of the tetrasaccharide acceptor 280 with the trisaccharide donor 283 (Scheme 9).

Scheme 9

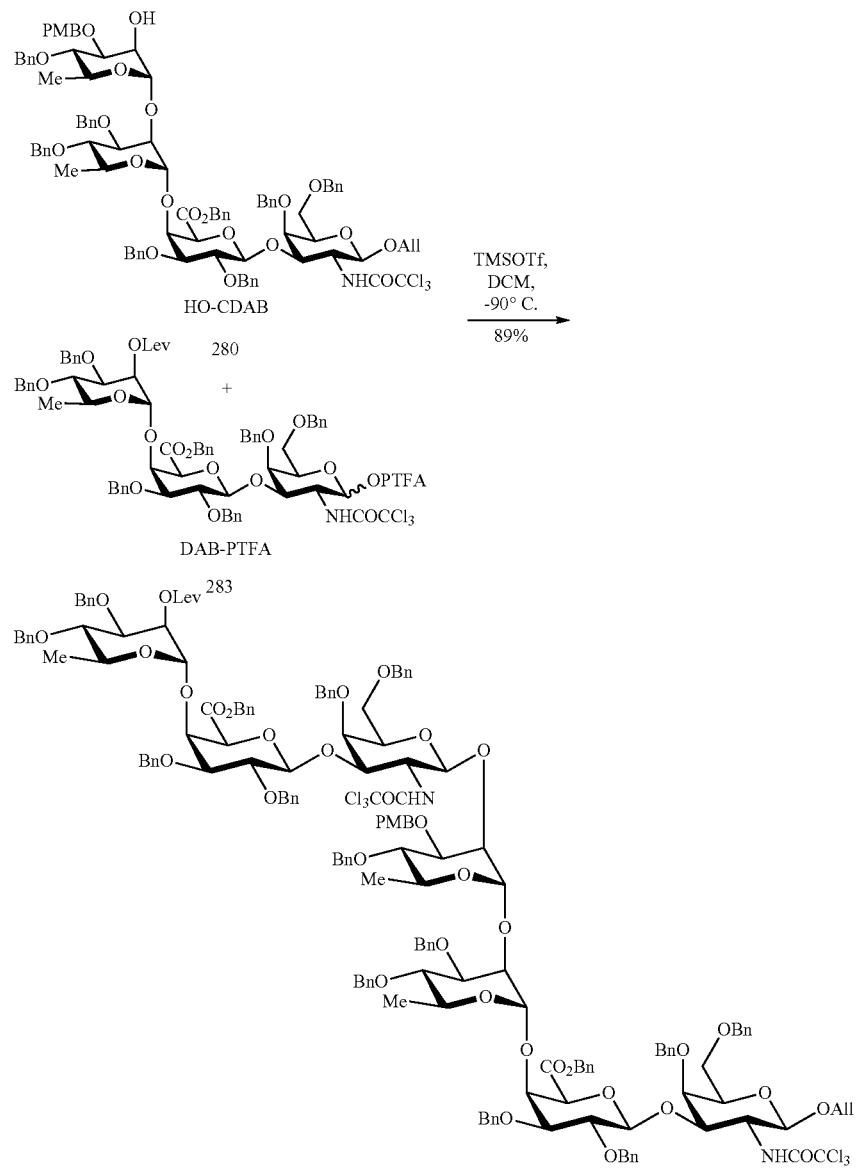

Allyl (3,4-di-O-benzyl-2-O-levulinoyl-α-L-rhamn-opyranosyl)-(1→4)-(benzyl 2,3-di-O-benzyl-β-D-galactopyranosyluronate)-(1→3)-(4,6-di-O-benzyl-2-deoxy-2-trichloroacetamido-β-D-galactopyranosyl)-(1→2)-(4-O-benzyl-3-O-para-methoxybenzyl-α-L-rhamnopyranosyl)-(1→2)-(3,4-di-O-benzyl-α-L-rhamnopyranosyl)-(1→4)-(benzyl 2,3-di-O-benzyl-β-D-galactopyranosyluronate)-(1→3)-4,6-di-O-benzyl-2-deoxy-2-trichloroacet-amido-β-D-galactopyranoside (294)

A mixture of tetrasaccharide acceptor 280 (0.50 g, 0.30 mmol), trisaccharide donor 283 (0.65 g, 0.42 mmol), and powdered 4 MS (1.25 g) in anhyd. DCM (7.5 mL) was stirred at rt under an Ar atmosphere for 1 h. The suspension was cooled to −90° C., and TMSOTf (2.7 µL, 15 µmol) was added. The reaction mixture was stirred for 30 min allowing the cooling bath to reach −78° C. and $Et_3N$ was added to quench the reaction. The suspension was filtered and the filtrate was concentrated to dryness. The residue was purified by flash chromatography (Tol/EtOAc 88:12 to 8:2) to give heptasaccharide 294 (0.81 g, 89%) as a white foam.

$^1$H NMR (CDCl$_3$), δ 7.41-6.95 (m, 78H, 77H$_{Ar}$, NH-2$_{B'}$), 6.82 (d, 1H, $J_{NH,2}$=6.7 Hz, NH-2$_B$), 6.81-6.78 (m, 2H, H$_{ArPMB}$), 5.87 (m, 1H, CH=$_{All}$), 5.42 (dd, 1H, $J_{1,2}$=1.9 Hz, $J_{2,3}$=3.0 Hz, H-2$_{D'}$), 5.29-5.20 (m, 5H, H-1$_D$, =CH$_{2All}$, 2H$_{CO2Bn}$, H-1$_{B'}$), 5.16 (m, 1H, $J_{cis}$=10.4 Hz, $J_{gem}$=1.5 Hz, =CH$_{2All}$), 5.14 (d, 1H, $J_{1,2}$=1.7 Hz, H-1$_{D'}$), 5.11 (d, 1H, J=12.2 Hz, H$_{CO2Bn}$), 5.10 (d, 1H, J=12.1 Hz, H$_{CO2Bn}$), 5.02 (d$_{po}$, 1H, $J_{1,2}$=8.2 Hz, H-1$_B$), 4.01 (d$_{po}$, 1H, J=11.6 Hz, H$_{Bn}$), 4.96 (d, 1H, $J_{1,2}$=1.4 Hz, H-1$_C$), 4.93 (2d$_o$, 2H, H$_{Bn}$), 4.88 (d, 1H, J=11.8 Hz, H$_{Bn}$), 4.81 (d, 1H, J=11.1 Hz, H$_{Bn}$), 4.79 (d, 1H, J=12.1 Hz, H$_{Bn}$), 4.78-4.68 (m, 7H, H-3$_{B'}$, 6H$_{Bn}$), 4.66-4.51 (m, 10H, 8H$_{Bn}$, H-1$_{A'}$, H-3$_B$), 4.49-4.39 (m, 5H, 3H$_{Bn}$, H-1$_A$, H-4$_{A'}$), 4.37-4.32 (m, 2H, H$_{All}$, H-4$_A$), 4.31 (bd, 1H, $J_{3,4}$=3.0 Hz, H-4$_{B'}$), 4.26 (d, 1H, J=10.8 Hz, H$_{Bn}$), 4.21-4.16 (m, 3H, H-4$_B$, 2H$_{Bn}$), 4.11-4.04 (m, 5H, H-2$_C$, H-5$_{A'}$, H$_{All}$, 2H$_{Bn}$), 3.98 (bs, 1H, H-5$_A$), 3.93 (pt, 1H, H-2$_D$), 3.88-3.80 (m, 3H, H-3$_C$, H-2$_{B'}$, H$_{Bn}$), 3.79-3.56 (m, 14H, H-5$_C$, H-5$_D$, H-2$_{A'}$, H-3$_{D'}$, H-3$_D$, CH$_{3PMB}$, H-2$_B$, H-6a$_B$, H-2$_A$, H-5$_B$, H-5$_D$, H-5$_{B'}$), 3.49 (dd, 1H, $J_{2,3}$=9.7 Hz, $J_{3,4}$=2.8 Hz, H-3$_{A'}$), 3.49-3.40 (m, 2H, H-4$_C$, H-3$_A$), 3.40-3.34 (m, 2H, H-6b$_B$, H-6a$_{B'}$), 3.33-3.26 (m, 3H, H-4$_D$, H-6b$_{B'}$, H-4$_{D'}$), 2.70-2.60 (m, 4H, CH$_{2Lev}$), 2.14 (s, 3H, CH$_{3Lev}$), 1.30 (d, 3H, $J_{5,6}$=6.2 Hz, H-6$_{D'}$), 1.29 (d, 3H, $J_{5,6}$=6.2 Hz, H-6$_D$), 1.20 (d, 3H, $J_{5,6}$=6.2 Hz, H-6$_C$).

$^{13}$C NMR (CDCl$_3$) partial, δ 206.1 (CO$_{Lev}$), 171.4 (CO$_{2Lev}$) 166.9 (2C, C-6$_A$, C-6$_{A'}$) 162.1 (NHCO-2$_B$), 161.7 (NHCO-2$_{B'}$), 159.2 (C$_{IVPMB}$), 130.7 (C$_{IVPMB}$), 113.7 (2C, C$_{ArPMB}$), 104.0 (C-1$_{A'}$), 103.8 (C-1$_A$), 101.0 (C-1$_C$), 100.4 (C-1$_D$), 99.0 (C-1$_{D'}$), 98.8 (C-1$_{B'}$), 97.5 (C-1$_B$), 92.7, 92.2 (2C, CCl$_3$), 67.4, 67.3 (2C, C$_{CO2Bn}$), 55.1 (CH$_{3PMB}$), 38.1 (COCH$_{2Lev}$), 29.8 (CH$_{3Lev}$), 28.2 (CO$_2$CH$_{2Lev}$).

HRMS (ESI$^+$): m/z 1536.4961 (calcd for $C_{167}H_{176}Cl_6N_2O_{38}Na_2$ [M+2Na]$^{2+}$: m/z 1536.4913).

Protected Octasaccharide (CDAB)$_2$ (300) and Dodecasaccharide (CDAB)$_3$ (302): Example of an Iterative Process.

As illustrated in the following, the building blocks listed in Table 1 are advantageously involved in an iterative process for the synthesis of structures larger than two repeating units. At least three glycosylation steps are required to reach the corresponding oligo- or polysaccharides. In this regard, tetrasaccharide CDAB-PTFA (284) was identified as crucial in the elongation process. It was designed to act as a donor and potential acceptor, and for that reason its 2$_C$-OH is masked with an orthogonal protecting group, namely a levulinoyl ester (Lev). Interestingly, the key tetrasaccharide 284 can thus be used repeatedly according to an iterative glycosylation/delevulinoylation process to reach the desired oligo- or polysaccharide length. Indeed, when performed at −90° C. under controlled conditions, the condensation of the HO-CDAB acceptor (280) and CDAB-PTFA donor (284) gave the fully protected (CDAB)$_2$ octasaccharide (300) in high yield. Hydrazynolysis of the levulinoyl ester located at position 2 of the non reducing end residue gave the octasaccharide acceptor HO-(CDAB)$_2$ (301), which was set to react with the same CDAB-PTFA donor (284), again at −90° C., to give the fully protected dodecasaccharide (CDAB)$_3$ in high yield (302). Please note that the reaction temperature is critical to ensure the required glycosylation. Dodecasaccharide 302 is thus obtained in 3 high yielding steps by appropriate combination of two out of the eight newly available building blocks (Scheme 10).

Scheme 10

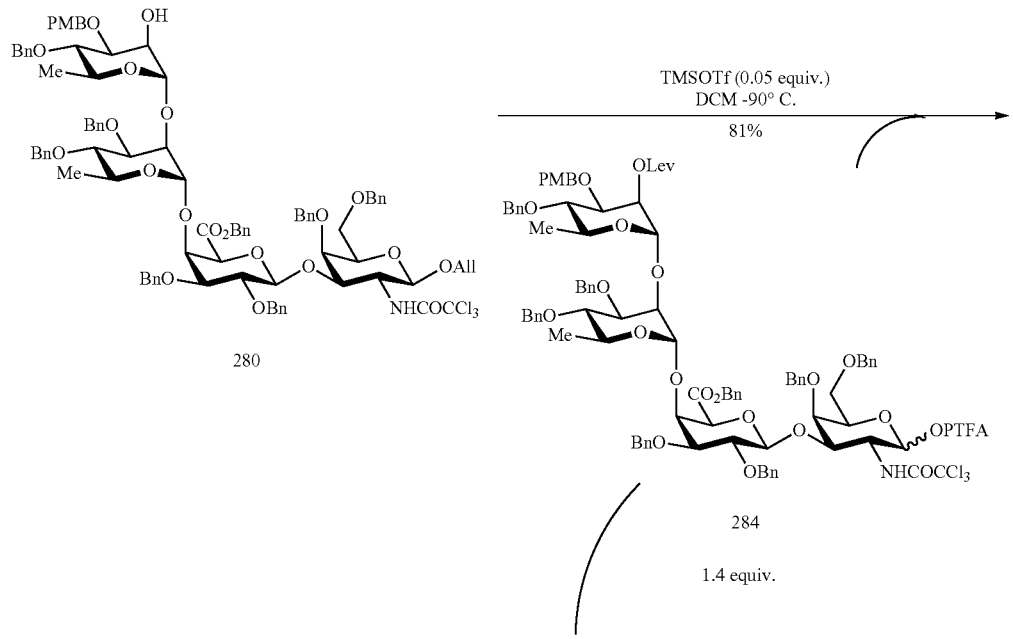

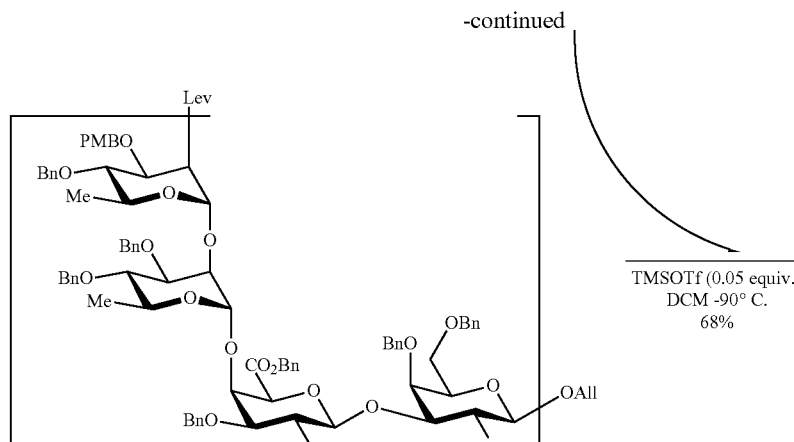

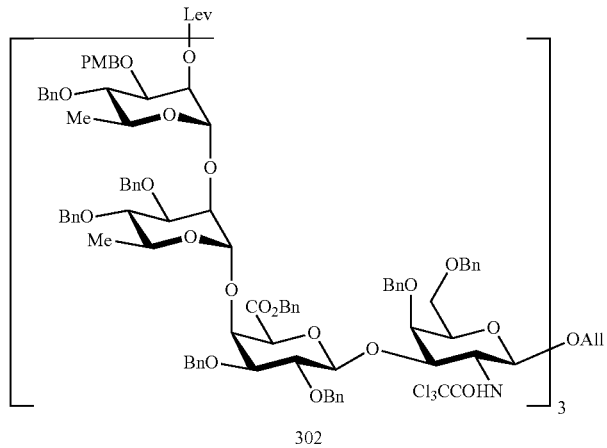

Allyl (4-O-benzyl-3-O-para-methoxybenzyl-2-O-levulinoyl-α-L-rhamnopyranosyl)-(1→2)-(3,4-di-O-benzyl-α-L-rhamnopyranosyl)-(1→4)-(benzyl 2,3-di-O-benzyl-β-D-galactopyranosyluronate)-(1→3)-(4,6-di-O-benzyl-2-deoxy-2-trichloroacetamido-β-D-galactopyranosyl)-(1→2)-(4-O-benzyl-3-O-para-methoxybenzyl-α-L-rhamnopyranosyl)-(1→2)-(3,4-di-O-benzyl-α-L-rhamnopyranosyl)-(1→4)-(benzyl 2,3-di-O-benzyl-β-D-galactopyranosyluronate)-(1→3)-4,6-di-O-benzyl-2-deoxy-2-trichloroacetamido-β-D-galactopyranoside (300)

A mixture of tetrasaccharide acceptor 280 (1.40 g, 0.84 mmol), tetrasaccharide donor 284 (2.23 g, 1.17 mmol), and powdered 4 MS (3.5 g) in anhyd. DCM (29 mL) was stirred at rt under an Ar atmosphere for 1 h. The suspension was cooled to −90° C., and TMSOTf (7.6 µL, 42 µmol) was added. The reaction mixture was stirred for 30 min allowing the cooling bath to reach −78° C. and Et$_3$N was added to quench the reaction. The suspension was filtered and the filtrate was concentrated to dryness. The residue was purified by flash chromatography (SiO$_2$ 20-40 µm, Tol/EtOAc 92:8 to 8:2) to give octasaccharide 300 (2.28 g, 81%) as a white foam.

$^1$H NMR (CDCl$_3$), δ 7.41-6.95 (m, 85H, 84H$_{Ar}$, NH-2$_{B'}$), 6.87-6.74 (m, 5H, 4H$_{ArPMB}$, NH-2$_B$), 5.87 (m, 1H, CH=$_{All}$), 5.46 (dd, 1H, J$_{1,2}$=1.9 Hz, J$_{2,3}$=3.1 Hz, H-2$_{C'}$), 5.28-5.20 (m, 6H, H-1$_D$, H-1$_{D'}$, =CH$_{2All}$, 2H$_{CO2Bn}$, H-1$_{B'}$), 5.16 (m, 1H, J$_{cis}$=10.4 Hz, J$_{gem}$=1.5 Hz, =CH$_{2All}$), 5.16-5.08 (m, 2H, H$_{CO2Bn}$), 5.04 (d, 1H, J=12.2 Hz, H$_{Bn}$), 5.03 (d, 1H, J$_{1,2}$=8.3 Hz, H-1$_B$), 4.96 (d, 1H, J$_{1,2}$=1.2 Hz, H-1$_C$), 4.95-4.86 (m, 4H, H$_{Bn}$), 4.81 (d$_{po}$, 1H, J=10.5 Hz, H$_{Bn}$), 4.79-4.71 (m, 7H, H-1$_{C'}$, 6H$_{Bn}$), 4.69 (dd$_{po}$, 1H, J$_{2,3}$=10.9 Hz, J$_{3,4}$=10.9 Hz, H-3$_{B'}$), 4.67-4.56 (m, 10H, H-3$_B$, 9H$_{Bn}$), 4.54 (d$_{po}$, 1H, J$_{1,2}$=7.5 Hz, H-1$_{A'}$), 4.53 (d, 1H, J=11.0 Hz, H$_{Bn}$), 4.49-4.39 (m, 5H, 4H$_{Bn}$, H-1$_A$), 4.38-4.30 (m, 4H, H-4$_{A'}$, H-4$_A$, H$_{All}$, H-4$_{B'}$), 4.21-4.16 (m, 3H, 2H$_{Bn}$, H-4$_B$), 4.21-4.04 (m, 6H, H-2$_{C'}$, H$_{All}$, 4H$_{Bn}$), 4.04 (bs, 1H, H-5$_{A'}$), 3.98 (bs, 1H, H-5$_A$), 3.96-3.93 (m, 2H, H-2$_D$, H-2$_{D'}$), 3.91 (ddpo, 1H, J$_{2,3}$=3.2 Hz, J$_{3,4}$=9.4 Hz, H-3$_{C'}$), 3.86-3.74 (m, 7H, H-3$_C$, H-2$_{B'}$, H-5$_C$, H-5$_{C'}$, CH$_{3PMB}$), 3.70-3.56 (m, 13H, H-5$_D$, H-2$_{A'}$, H-3$_{D'}$, H-3$_D$, CH$_{3PMB}$, H-2$_B$, H-6a$_B$, H-2$_A$, H-5$_B$, H-5$_D$, H-5$_{B'}$), 3.46-3.25 (m, 9H, H-3$_{A'}$, H-3$_A$, H-4$_{C'}$, H-6b$_B$, H-6a$_B$, H-4$_D$, H-6b$_{B'}$, H-4$_{D'}$), 2.76-2.66 (m, 4H, CH$_{2Lev}$), 2.18 (s, 3H, CH$_{3Lev}$), 1.29 (d, 3H, J$_{5,6}$=6.2 Hz, H-6$_D$), 1.28 (d, 3H, J$_{5,6}$=6.2 Hz, H-6$_D$), 1.20 (2d$_o$, 6H, J$_{5,6}$=6.2 Hz, H-6$_C$, H-6$_{C'}$).

$^{13}$C NMR (CDCl$_3$) partial, δ 206.1 (CO$_{Lev}$), 171.6 (CO$_{2Lev}$), 166.9 (2C, C-6$_A$, C-60), 162.1 (NHCO-2$_B$), 161.7 (NHCO-2$_B$), 159.2 (2C, C$_{IVPMB}$), 130.6, 130.3 (2C, $C_{IVPMB}$), 113.7 (4C, $C_{ArPMB}$), 103.9 (C-$1_{A'}$), 103.8 (C-$1_A$), 101.0 (C-$1_C$), 100.4 (C-$1_D$), 100.1 (C-$1_{D'}$), 99.2 (C-$1_{C'}$), 98.8 (C-$1_{B'}$), 97.5 (C-$1_B$), 92.7, 92.2 (2C, CCl$_3$), 67.3 (2C, $C_{CO2Bn}$), 55.2, 55.1 (2C, $C_{H3PMB}$), 38.1 (COCH$_{2LEV}$), 29.8 (CH$_{3Lev}$), 28.2 (CO$_2$CH$_{2Lev}$).

HRMS (ESI$^+$): m/z 1714.5948 (calcd for $C_{188}H_{200}Cl_6N_2O_{43}Na_2$ [M+2Na]$^{2+}$: m/z 1714.5725).

Allyl (4-O-benzyl-3-O-para-methoxybenzyl-α-L-rhamnopyranosyl)-(1→2)-(3,4-di-O-benzyl-α-L-rhamnopyranosyl)-(1→4)-(benzyl 2,3-di-O-benzyl-β-D-galactopyranosyluronate)-(1→3)-(4,6-di-O-benzyl-2-deoxy-2-trichloroacetamido-β-D-galactopyranosyl)-(1→2)-(4-O-benzyl-3-O-para-methoxybenzyl-α-L-rhamnopyranosyl)-(1→2)-(3,4-di-O-benzyl-α-L-rhamnopyranosyl)-(1→4)-(benzyl 2,3-di-O-benzyl-β-D-galactopyranosyluronate)-(1→3)-4,6-di-O-benzyl-2-deoxy-2-trichloroacetamido-β-D-galactopyranoside (301)

To a solution of the fully protected 300 (1.31 g, 0.39 mmol) in anhyd. pyridine (9.6 mL) stirred at 0° C. under an Ar atmosphere was added dropwise AcOH (6.4 mL) followed by hydrazine monohydrate (94 μL, 1.93 mmol). The reaction mixture was stirred for 1.5 h allowing the cooling bath to reach rt. Following addition of DCM and water, the two layers were separated and the aq. one was re-extracted twice with DCM. The combined organic extracts were washed with brine, dried by passing through a phase separator filter and volatiles were evaporated. The residue was purified by flash chromatography (Tol/EtOAc 9:1 to 75:25) to give alcohol 301 (1.05 mg, 82%) as a white foam.

$^1$H NMR (CDCl$_3$), δ 7.41-6.94 (m, 85H, 84H$_{Ar}$, NH-$2_{B'}$), 6.90-6.86 (m, 2H, H$_{ArPMB}$), 6.84 (d, 1H, $J_{NH,2}$=6.7 Hz, NH-$2_B$), 6.82-6.78 (m, 2H, H$_{ArPMB}$), 5.87 (m, 1H, CH$_{=All}$), 5.29-5.20 (m, 6H, H-$1_D$, H-$1_{D'}$, =CH$_{2All}$, 2H$_{CO2Bn}$, H-$1_{B'}$), 5.16 (m, 1H, $J_{cis}$ 10.4 Hz, $J_{gem}$ =1.5 Hz, =CH$_{2All}$), 5.16-5.09 (m, 2H, H$_{CO2Bn}$), 5.04 (d, 1H, J=11.4 Hz, H$_{Bn}$), 5.03 (d, 1H, $J_{1,2}$=8.3 Hz, H-$1_B$), 4.96 (d, 1H, $J_{1,2}$=1.4 Hz, H-$1_C$), 4.95-4.86 (m, 5H, H-$1_{C'}$, H$_{Bn}$), 4.83-4.68 (m, 8H, 7H$_{Bn}$, H-$3_{B'}$), 4.68-4.51 (m, 13H, 11H$_{Bn}$, H-$3_B$, H-$1_{A'}$), 4.49-4.40 (m, 4H, 3H$_{Bn}$, H-$1_A$), 4.39-4.31 (m, 4H, H-$4_{A'}$, H-$4_A$, H$_{All}$, H-$4_{B'}$), 4.22-4.16 (m, 3H, 2H$_{Bn}$, H-$4_B$), 5.14 (d, 1H, J=11.2 Hz, H$_{Bn}$), 4.12-4.04 (m, 7H, H-$2_C$, H$_{All}$, 3H$_{Bn}$, H-$2_{C'}$, H-$5_{A'}$), 4.00 (pt$_{po}$, 1H, H-$2_{D'}$), 3.99 (s$_o$, 1H, H-$5_A$), 3.94 (pt, 1H, H-$2_D$), 3.88-3.74 (m, 8H, H-$3_{C'}$, H-$3_C$, H-$2_{B'}$, H-$5_C$, H-$5_{C'}$, CH$_{3PMB}$), 3.72-3.56 (m, 13H, H-$5_{D'}$, H-$2_{A'}$, H-$3_{D'}$, H-$3_D$, CH$_{3PMB}$, H-$2_B$, H-6a$_B$, H-$2_A$, H-$5_B$, H-$5_D$, H-$5_{B'}$), 3.48-3.26 (m, 9H, H-$3_{A'}$, H-$4_C$, H-$3_A$, H-$4_{C'}$, H-6b$_B$, H-6a$_{B'}$, H-$4_D$, H-6b$_{B'}$, H-$4_{D'}$), 2.37 (bs, 1H, OH-$2_{C'}$), 1.30 (d$_{po}$, 3H, $J_{5,6}$=6.2 Hz, H-$6_D$*), 1.29 (d$_{po}$, 3H, $J_{5,6}$=6.2 Hz, H-$6_{D'}$*), 1.21 (d, 3H, $J_{5,6}$=6.2 Hz, H-$6_C$*), 1.20 (d, 3H, $J_{5,6}$=6.2 Hz, H-$6_{C'}$*).

$^{13}$C NMR (CDCl$_3$) partial, δ 166.9 (2C, C-$6_A$, C-$6_{A'}$), 162.1 (NHCO-$2_B$), 161.7 (NHCO-$2_{B'}$), 159.4, 159.2 (2C, $C_{IVPMB}$), 130.7, 130.2 (2C, $C_{IVPMB}$), 113.9, 113.7 (4C, $C_{ArPMB}$), 104.0 (C-$1_{A'}$), 103.8 (C-$1_A$), 101.0 (C-$1_C$), 100.7 (C-$1_{C'}$), 100.4 (C-$1_D$), 100.3 (C-$1_{D'}$), 98.8 (C-$1_{B'}$), 97.4 (C-$1_B$), 92.7, 92.2 (2C, CCl$_3$), 67.2 (2C, $C_{CO2Bn}$), 55.2, 55.1 (2C, CH$_{3PMB}$).

HRMS (ESI$^+$): m/z 1665.5668 (calcd for $C_{183}H_{194}Cl_6N_2O_{41}Na_2$ [M+2Na]$^{2+}$: m/z 1665.5542).

Allyl (4-O-benzyl-3-O-para-methoxybenzyl-2-O-levulinoyl-α-L-rhamnopyranosyl)-(1→2)-(3,4-di-O-benzyl-α-L-rhamnopyranosyl)-(1→4)-(benzyl 2,3-di-O-benzyl-β-D-galactopyranosyluronate)-(1→3)-(4,6-di-O-benzyl-2-deoxy-2-trichloroacetamido-β-D-galactopyranosyl)-(1→2)-(4-O-benzyl-3-O-para-methoxybenzyl-α-L-rhamnopyranosyl)-(1→2)-(3,4-di-O-benzyl-α-L-rhamnopyranosyl)-(1→4)-(benzyl 2,3-di-O-benzyl-β-D-galactopyranosyluronate)-(1→3)-(4,6-di-O-benzyl-2-deoxy-2-trichloroacetamido-β-D-galactopyranosyl)-(1→2)-(4-O-benzyl-3-O-para-methoxybenzyl-α-L-rhamnopyranosyl)-(1→2)-(3,4-di-O-benzyl-α-L-rhamnopyranosyl)-(1→4)-(benzyl 2,3-di-O-benzyl-β-D-galactopyranosyluronate)-(1→3)-4,6-di-O-benzyl-2-deoxy-2-trichloroacetamido-β-D-galactopyranoside (302)

A mixture of octasaccharide acceptor 301 (153 g, 46 μmol), tetrasaccharide donor 284 (121 mg, 64 μmol), and powdered 4 MS (375 mg) in anhyd. DCM (1.6 mL) was stirred at rt under an Ar atmosphere for 1 h. The suspension was cooled to −90° C., and TMSOTf (0.4 μL, 2 μmol) was added. The reaction mixture was stirred for 30 min allowing the cooling bath to reach −78° C. and Et$_3$N was added to quench the reaction since a TLC control (Tol/acetone 9:1) showed the presence of a new major compound (rf=0.24) and that no acceptor (rf=0.19) nor donor (rf=0.41) remained. The suspension was filtered over and the filtrate was concentrated to dryness. The residue was purified by flash chromatography (SiO$_2$ 20-40 μm, Tol/EtOAc 92:8 to 8:2) to give dodecasaccharide 302 (156 mg, 68%) as a white foam.

$^1$H NMR (CDCl$_3$), 7.42-6.94 (m, 129H, 126H$_{Ar}$, NH-$2_{B''}$, NH-$2_{B'}$, NH-$2_B$), 6.87-6.77 (m, 6H, H$_{ArPMB}$), 5.87 (m, 1H, CH$_{=All}$), 5.48 (dd, 1H, $J_{1,2}$=1.7 Hz, $J_{2,3}$=3.1 Hz, H-$2_{C''}$), 5.29-5.15 (m, 10H, H-$1_D$, H-$1_{D''}$, H-$1_{D'}$, =CH$_{2All}$, 3H$_{CO2Bn}$, H-$1_{B''}$, =CH$_{2All}$), 5.13-5.07 (m, 3H, H$_{CO2Bn}$), 5.05 (d, 1H, J=11.2 Hz, H$_{Bn}$), 5.03 (d, 1H, $J_{1,2}$=8.4 Hz, H-$1_B$), 5.00 (d, 1H, J=11.3 Hz, H$_{Bn}$), 4.98-4.88 (m, 7H, H-$1_C$, H-$1_{C'}$, 5H$_{Bn}$), 4.87-4.67 (m, 14H, H-$1_{C''}$, H-$3_{B''}$, H-$3_{B'}$, 11H$_{Bn}$), 4.68-4.39 (m, 25H, H-$3_B$, H-$1_{A''}$, H-$1_A$, H-$1_{A'}$, 21H$_{Bn}$), 4.38-4.31 (m, 5H, H-$4_{A''}$, H-$4_{A'}$, H-$4_A$, H$_{All}$, H-$4_{B'}$*), 4.28 (d, 1H, $J_{3,4}$=3.2 Hz, H-$4_{B'}$*), 4.22-4.16 (m, 4H, 3H$_{Bn}$, H-$4_B$), 4.16-3.98 (m, 13H, H-$2_C$, H$_{All}$, H-$2_{C'}$ H-$5_{A''}$, H-$5_{A'}$, H-$5_A$, 7H$_{Bn}$), 3.97-3.90 (m, 3H, H-$2_D$, $2_{D''}$, H-$3_{C''}$), 3.89 (pt, 1H, H-$2_{D'}$), 3.87-3.74 (m, 10H, H-$3_{C'}$, H-$3_C$, H-$2_{B'}$, H-$2_{B''}$, H-$5_C$, H-$5_{C'}$, H-$5_{C''}$, CH$_{3PMB}$), 3.71-3.55 (m, 20H, H-$5_D$, H-$5_{D'}$, H-$5_{D''}$, H-$2_B$, H-$5_B$, H-$5_{B'}$, H-$5_{B''}$, H-$2_A$, H-$2_{A'}$, H-$2_{A''}$, H-$3_D$, H-$3_{D'}$, H-$3_{D''}$, 2CH$_{3PMB}$, H-6a$_B$), 3.47-3.24 (m, 14H, H-$3_{A'}$, H-$3_{A''}$, H-$4_C$, H-$3_A$, H-$4_C$, H-$4_{C''}$, H-6b$_B$, H-6a$_{B'}$, H-6a$_{B''}$, H-$4_D$, H-6b$_{B''}$, H-6b$_{D'}$, H-$4_{D'}$), 2.77-2.67 (m, 4H, CH$_{2Lev}$), 2.12 (s, 3H, CH$_{3Lev}$), 1.32-1.29 (m, 9H, H-$6_D$, H-$6_{D'}$, H-$6_{D''}$), 1.23-1.19 (m, 9H, H-$6_C$, H-$6_{C'}$, H-$6_{C''}$).

$^{13}$C NMR (CDCl$_3$) partial, δ 206.2 (CO$_{LEV}$), 171.7 (CO$_{2Lev}$), 166.9 (3C, C-$6_A$, C-$6_{A'}$, C-$6_{A''}$), 162.1 (NHCO-$2_B$), 161.7 (2C, NHCO-$2_{B'}$, NHCO-$2_{B''}$), 159.2, 159.1 (3C, $C_{IVPMB}$), 130.7, 130.2 (3C, $C_{IVPMB}$), 113.9, 113.7 (6C, $C_{ArPMB}$), 103.9-103.8 (3C, C-$1_A$, C-$1_{A'}$, C-$1_{A''}$), 101.0 (2C, C-$1_C$, C-$1_{C'}$), 100.4, 100.2 (3C, C-$1_D$, C-$1_{D'}$, C-$1_{D''}$), 99.2 (C-$1_{C''}$), 98.8 (C-$1_{B''}$, C-$1_{B'}$), 97.4 (C-$1_B$), 92.6, 92.2 (3C, CCl$_3$), 67.4-67.3 (3C, $C_{CO2Bn}$), 55.2, 55.1 (3C, CH$_{3PMB}$), 38.2 (COCH$_{2Lev}$), 29.9 (CH$_{3Lev}$), 28.2 (CO$_2$CH$_{2Lev}$).

II. Antigenicity of the Oligo- and/or Polysaccharides of the Invention

A. Materials and Methods

1) Production and Characterization of mAbs Specific for S. flexneri Serotype 6 LPS Mice were immunized with heat-killed bacteria prepared with the strain *Shigella flexneri* serotype 6 (SF6) named Sc544. Briefly, mice were immunized first intraperitoneally (i.p.) with $10^8$ heat-killed bacteria mixed with incomplete Freund adjuvant, then twice i.p. with $10^8$ heat-killed bacteria without adjuvant at one month interval. Immunogenicity was measured by ELISA (as described for the identification of the appropriate concentration of IgG to use for IC50 measurement) against SF6 LPS purified from the strain SF6 Sc544 according to Westphal O and Jann K (Methods Carbohydr. Chem. 5 83 (1965)). Mice displaying an anti-LPS SF6 antibody response were then submitted to an intravenous (i.v.) injection boost 3 days prior to be sacrificed for spleen recovery to perform cell fusion for the obtention of hybridoma, as described in Phalipon A. et al (J. Immunol. 176 1686 (2006)).

Hybridoma were selected from the supernatant of the cell culture issued from the fusion by ELISA against purified SF6 LPS. Positive hybridoma were used for the production of a large amount of the corresponding mAb, that was purified by G-protein chromatography. Thus, the hybridoma A22-4' secreting the monoclonal antibody mIgG A22-4' was deposited at the Collection Nationale de Culture de Microorganismes (CNCM, Paris, France) according to the Budapest Treaty under number I-4813, on Oct. 28, 2013.

2) ELISA for IC50 Measurements

The binding of the available mIgG A22-4' to the synthetic oligosaccharides was measured as previously described (Phalipon A. et al (J. Immunol. 176 1686 (2006)). Briefly, the mIgG concentration to be used was defined in the first step. To do so, a standard curve was established for mIgG A22-4'. The mIgG was incubated at different concentrations, overnight at 4° C., on microtiter plates coated with SF6 LPS purified from the strain SF6 Sc544 at a concentration of 2.5 m/mL in a carbonate buffer (pH 9.6), then with PBS-BSA 1% for 30 min at 4° C. After washing with PBS-Tween 20 (0.05%), alkaline phosphatase conjugated anti-mouse IgG was added at a dilution of 1/5,000 (Sigma-Aldrich) for 1 h at 37° C. After washing with PBS-Tween 20 (0.05%), the substrate was added (12 mg of p-nitrophenyl phosphate in 1.2 mL of 1 M Tris-HCl buffer (pH 8.8) and 10.8 mL of 5 M NaCl). Once the color developed, the plate was read at 405 nm Dynatech MR400 microplate reader). A standard curve OD=f([Ab]) was fitted to the quadratic equation $Y=aX2+bX+c$, where Y is the OD and X is the Ab concentration. A correlation factor ($r^2$) of 0.99 was routinely obtained. The mIgG A22-4' concentration to be used in the second step for measuring the IC50, which is defined as the concentration of oligosaccharides required to inhibit 50% of mIgG binding to LPS, was chosen as follows. It corresponds to the minimal concentration of mAb which gives the maximal OD on the standard curve.

Then for IC50 measurement, the mIgG A22-4', used at the concentration of 0.025 μg/ml, was incubated overnight at 4° C. with different concentrations of the oligosaccharides to be tested in PBS-BSA 1%. The maximum concentration tested was 2.5 mM for all oligosaccharides. Then, measurement of unbound mIgG was performed as described above using microtiter plates coated with purified SF6 LPS. The mAb concentration was deduced from the standard curve. A 100% unbound mIgG concentration was defined for the mAb incubated in the same conditions but without any oligosaccharide. Finally, a curve corresponding to % unbound mIgG=f([oligosaccharide]) allows to calculate the IC50 for each oligosaccharide tested.

B. Results

The binding of mIgG A22-4' to the synthetic and oligo- or polysaccharides was evaluated in inhibition ELISA (Table B)

| Synthetic Oligosaccharides tested as propyl glycoside | IC$_{50}$ (mM)[#] |
|---|---|
| CDAB | 0.016 |
| $_{Ac}$CDAB | 0.036 |
| $_{Ac}$CDAB$_{Ac}$C | ≤0.5 |
| CDABCDA | 0.015 |
| CDABCDAB | 0.004 |
| BCDAB | 0.025 |
| BCDABC | ≤0.5 |
| BCDABCDA | 0.018 |
| DABCDAB | 0.053 |
| ABCDAB | 0.019 |

[#] "≤" corresponds to values inferior to but close to the mentionned value.

REFERENCES

[1] K. Hygge Blakeman, A. Weintraub, G. Widmalm, *Eur. J. Biochem.* 1998, 251, 534-537.

[2] M. M. Levine, *Vaccine* 2006, 24, 3865-3873.

[3] S. K. Niyogi, *J. Microbiol.* 2005, 43, 133-143.

[4] L. von Seidlein, D. R. Kim, M. Ali, H. Lee, X. Wang, V. D. Thiem, G. Canh do, W. Chaicumpa, M. D. Agtini, A. Hossain, Z. A. Bhutta, C. Mason, O. Sethabutr, K. Talukder, G. B. Nair, J. L. Deen, K. Kotloff, J. Clemens, *PLoS Med.* 2006, 3, e353.

[5] a) M. M. Levine, K. L. Kotloff, E. M. Barry, M. F. Pasetti, M. B. Sztein, *Nat. Rev. Microbiol.* 2007, 5, 540-553; b) M. N. Kweon, *Curr. Opin. Infect. Dis.* 2008, 21, 313-318.

[6] K. L. Kotloff, J. P. Winickoff, B. Ivanoff, J. D. Clemens, D. L. Swerdlow, P. J. Sansonetti, G. K. Adak, M. M. Levine, *Bull. World Health Organ.* 1999, 77, 651-666.

[7] a) C. Ferreccio, V. Prado, A. Ojeda, M. Cayyazo, P. Abrego, L. Guers, M. M. Levine, *Am. J. Epidemiol.* 1991, 134, 614-627; b) 3. H. Passwell, S. Ashkenzi, Y. Banet-Levi, R. Ramon-Saraf, N. Farzam, L. Lerner-Geva, H. Even-Nir, B. Yerushalmi, C. Y. Chu, J. Shiloach, J. B. Robbins, R. Schneerson, I. S. S. Grp, *Vaccine* 2010, 28, 2231-2235.

[8] F. R. Noriega, F. M. Liao, D. R. Maneval, S. Ren, S. B. Formal, M. M. Levine, *Infect. Immun.* 1999, 67, 782-788.

[9] a) D. A. Simmons, E. Romanowska, *J. Med. Microbiol.* 1987, 23, 289-302; b) A. V. Perepelov, M. E. Shekht, B. Liu, S. D. Shevelev, V. A. Ledov, S. N. Senchenkova, V. L. Lvov, A. S. Shashkov, L. Feng, P. G. Aparin, L. Wang, Y. A. Knirel, *FEMS Immunol. Med. Microbiol.* 2012, DOI: 10.1111/j.1574-1695X.2012.01000.x.

[10] H. L. DuPont, R. B. Hornick, M. J. Snyder, J. P. Libonati, S. B. Formal, E. J. Gangarosa, *J. Infect. Dis.* 1972, 125, 12-16.

[11] a) A. Phalipon, M. Tanguy, C. Grandjean, C. Guerreiro, F. Belot, D. Cohen, P. J. Sansonetti, L. A. Mulard, *J. Immunol.* 2009, 182, 2241-2247; b) M. Wacker, C. Waechter, in WO 2011/062625 A1, Vol. WO 2011/062625 A1 (Ed.: Glycovaxyn), CH, 2011, pp. 1-156.

[12] R. W. Kaminski, E. V. Oaks, *Expert Rev. Vaccines* 2009, 8, 1693-1704.

[13] a) P. Costantino, R. Rappuoli, F. Berti, *Expert Opin Drug Discov* 2011, 6, 1045-1066; b) E. Jessouroun, I. A. Freitas Brasileiro Da Silveira, C. Chagas Bastos, C. E. Frasch, C. H. Lee, in US 2007/0110762 A1, Vol. US

[14] G. T. Hermanson, *Bioconjugate techniques, 2nd Edition*, Academic Press Inc., San Diego, 2008.

[15] A. Fattom, R. Schneerson, D. C. Watson, W. W. Karakawa, D. Fitzgerald, I. Pastan, X. Li, J. Shiloach, D. A. Bryla, J. B. Robbins, *Infect Immun* 1993, 61, 1023-1032.

[16] a) G. S. Bixler, Jr., R. Eby, K. M. Demiody, R. M. Woods, R. C. Seid, S. Pillai, *Adv Exp Med Biol* 1989, 251, 175-180; b) P. Costantino, S. Viti, A. Podda, M. A. Velmonte, L. Nencioni, R. Rappuoli, *Vaccine* 1992, 10, 691-698.

[17] J. Kim, F. J. Michon, in WO 2005/000346 A1, Vol. WO 2005/000346 A1, USA, 2005.

[18] J. H. Passwell, S. Ashkenazi, E. Harley, D. Miron, R. Ramon, N. Farzam, L. Lerner-Geva, Y. Levi, C. Chu, J. Shiloach, J. B. Robbins, R. Schneerson, *Pediatr Infect Dis J* 2003, 22, 701-706.

[19] P. R. Paradiso, D. A. Hagerman, D. V. Madore, H. Keyserling, J. King, K. S. Reisinger, M. M. Blatter, E. Rothstein, H. H. Bernstein, J. Hackell, *Pediatrics* 1993, 92, 827-832.

[20] D. Vahnori, A. Pessi, E. Bianchi, G. Corradin, *J Immunol* 1992, 149, 717-721.

[21] J. Alexander, J. Sidney, S. Southwood, J. Ruppert, C. Oseroff, A. Maewal, K. Snoke, H. M. Serra, R. T. Kubo, A. Sette, et al., *Immunity* 1994, 1, 751-761.

[22] S. Kaeothip, P. Pornsuriyasak, N. P. Rath, A. V. Demchenko, *Org Lett* 2009, 11, 799-802.

[23] A. F. Bongat, M. N. Kamat, A. V. Demehenko, *J Org Chem* 2007, 72, 1480-1483.

[24] a) P. J. Kocienski, *Protecting groups*, 3rd ed., Thieme, Stuttgart, 2004; b) P. G. M. Wuts, T. W. Greene, *Greene's protective groups in organic synthesis*, 4th ed., Wiley-Interscience, Hoboken, N.J.; Chichester, 2007.

[25] A. V. Demchenko, *Handbook of chemical glycosylation: advances in stereoselectivity and therapeutic relevance*, Wiley-VCH, Weinheim; Chichester, 2008.

[26] M. K. Gurjar, A. S. Mainkar, *Tetrahedron* 1992, 48, 6729-6738.

[27] S. Kramer, B. Nolting, A. J. Ott, C. Vogel, *J. Carbohydr. Chem.* 2000, 19, 891-921.

[28] J. Boutet, L. A. Mulard, *Eur. J. Org. Chem.* 2008, 5526-5542.

[29] P. Westerduin, P. E. de Haan, M. J. Dees, J. H. van Boom, *Carbohydrate Research* 1988, 180, 195-205.

[30] F. Belot, J. C. Jacquinet, *Carbohydr. Res.* 1996, 290, 79-86.

[31] B. M. Pinto, D. G. Morissette, D. R. Bundle, *J. Chem. Soc. Perkin Trans.* 1 1987, 9-14.

The invention claimed is:

1. A vaccine composition comprising a physiologically acceptable vehicle and a conjugate comprising an oligo- or polysaccharide selected from the group consisting of:

$(X)_x\text{-}\{BCDA\}_n\text{-}(Y)_y$ $(X)_x\text{-}\{CDAB\}_n\text{-}(Y)_y$ $(X)_x\text{-}\{DABC\}_n\text{-}(Y)_y$ $(X)_x\text{-}\{ABCD\}_n\text{-}(Y)_y$ wherein:
n is an integer comprised between 2 and 10,
A is a beta-d-Galacturonic acid (1,3) residue,
B is a N-acetyl-beta-d-Galactosamine (1,2) residue,
C is independently, at each occurrence, an alpha-I-Rhamnose (1,2) residue, wherein at most one of its 3c or 4c positions is OAc (i.e O—C(=O)CH$_3$), provided that there is at least one occurrence of C wherein the 3c position is not OAc, and provided that when C is a non reducing end residue, its 2c position may be acetylated or not,
D is an alpha-I-Rhamnose (1,4) residue,
x and y are independently selected among 0 and 1,
X and Y are independently selected among A, B, C, D, AB, BC, CD, DA, ABC, BCD, CDA, DAB,
provided that the ratio of 3C-OAc/4C-OAc is greater than 1,
said oligo- or polysaccharide being bound to a carrier.

2. The vaccine composition according to claim 1, wherein the oligo- or polysaccharide is liable to be bound by an anti-SF6 and/or anti-SF6a antibody.

3. The vaccine composition according to claim 1, wherein said oligo- or polysaccharide is selected from the group consisting of:

$\{BCDP\}_n,$ $\{CDAB\}_n,$ $\{DABC\}_{n, \text{and}}$ $\{ABCD\}_n$ wherein A, B, C, and D are as defined in claim 1 and n is an integer comprised between 2 and 10.

4. The vaccine composition according to claim 1, wherein n is comprised between 2 and 6.

5. The vaccine composition according to claim 1, wherein the carrier is selected among a protein or a peptide comprising at least one T-helper epitope, or a derivative thereof.

6. The vaccine composition according to claim 5, wherein the carrier is a *Shigella* protein able to induce a protective immune response against several *Shigella* serotypes.

7. The vaccine composition according to claim 1, wherein the carrier is tetanus toxoid or a fragment thereof.

8. The vaccine composition according to claim 1, wherein the carrier is a liposome.

9. The vaccine composition according to claim 1, wherein the oligo- or polysaccharide is bound to the carrier via a spacer which does not contain any carbohydrate residue.

10. The vaccine composition according to claim 1, wherein the oligo- or polysaccharide to carrier ratio is comprised between 1:1 and 30:1.

11. The vaccine composition according to claim 1, wherein the oligo- or polysaccharide is $\{CDAB\}_n$, wherein A, B, C, and D are as defined in claim 1 and n is an integer comprised between 2 and 10.

12. The vaccine composition of claim 1, further comprising an immunogen which affords protection against another pathogen, such as for example, *S. flexneri* serotype 1 b, 2a and 3a, members of other *Shigella* species such as *S. sonnei* and *S. dysenteriae* type 1, or pathogens responsible for diarrhoeal disease in humans.

13. The vaccine composition according to claim 1, which is formulated for parenteral, oral, intranasal, intradermal, subcutaneous or transcutaneous administration.

14. A vaccine composition comprising a physiologically acceptable vehicle and a conjugate comprising an oligo- or polysaccharide (Ia) selected from the group consisting of:

$(X)_x\text{-}\{BCDA\}_n\text{-}(Y)_y\text{-}OQ$ $(X)_x\text{-}\{CDAB\}_n\text{-}(Y)_y\text{-}OQ$ $(X)_x\text{-}\{DABC\}_n\text{-}(Y)_y\text{-}OQ$ $(X)_x\text{-}\{ABCD\}_n\text{-}(Y)_y\text{-}OQ$ Wherein:
A, B, C, D, X, Y, x, y and n are as defined in claim 1, provided that the ratio of 3C-OAc/4C-OAc is greater than 1,
O is the $C_1$ oxygen atom of the reducing end residue of the oligo- or polysaccharide,
Q is H, or a group LZ,
L is a divalent $C_1$-$C_{12}$ alkyl or alkenyl chain optionally interrupted by one or more heteroatoms, notably selected from an oxygen atom, a sulphur atom or a nitrogen atom, said nitrogen and sulphur atoms being optionally oxidized, and the nitrogen atom being optionally involved in an acetamide bond, and
Z is a terminal reactive function, optionally protected, able to form a covalent bond with a carrier and/or a solid support.

15. The vaccine composition of claim 14, wherein Z is Hal, biotin, $C_2$-$C_6$ alkenyl, $C_2$-$C_6$ alkynyl, azido, alkoxy, epoxyde, acetal, C(=O)H, $SR_1$, $NH_2$ or NHC(=O)$CH_2$Hal,
$R_1$ being H, C(=O)$CH_3$ or $SR_2$, and
$R_2$ being a $C_1$-$C_6$ alkyl, a $C_6$-$C_{10}$ aryl, or a 5 to 7 membered heteroaryl, such as pyridyl, or any group allowing to convert $SSR_2$ into SH.

16. The vaccine composition according to claim 14, which is immobilized on a solid support.

17. A vaccine composition comprising a physiologically acceptable vehicle and a conjugate comprising an oligo or polysaccharide (Ib) selected from the group consisting of:

$(X)_x\text{-}\{BCDA\}_n\text{-}(Y)_y\text{-}W$ $(X)_x\text{-}\{CDAB\}_n\text{-}(Y)_y\text{-}W$ $(X)_x\text{-}\{DABC\}_n\text{-}(Y)_y\text{-}W$ $(X)_x\text{-}\{ABCD\}_n\text{-}(Y)_y\text{-}W$ Wherein:
A is a beta-d-Galacturonic (1,3) acid residue,
B is a N-protected-beta-d-Galactosamine (1,2) residue, wherein said N-protecting group is an acetyl group, or a precursor thereof such as a N-trichloroacetyl group,
C is an alpha-l-Rhamnose (1,2) residue, wherein at most one of 3c or 4c is OAc,
D is an alpha-l-Rhamnose (1,4) residue,
x and y are independently selected among 0 and 1,
n is an integer comprised between 2 and 10,
X and Y are independently selected among A, B, C, D, AB, BC, CD, DA, ABC, BCD, CDA, DAB,
provided that the ratio of 3C-OAc/4C-OAc is greater than 1,
wherein each OH and/or $CO_2H$ group of said residues are optionally protected by a protecting group,
W is $OR^i$, $SR^{ii}$ or Hal, wherein said O, S and Hal are the $C_1$ heteroatom of the reducing end residue of the oligo- or polysaccharide chain, S being optionally oxidized,
$R^i$ is H, a hydroxyl protecting group, an anomeric hydroxyl activating group, or a LZ group, L and Z being as defined above for formula (Ia),
$R^{ii}$ is $C_1$-$C_{12}$ alkyl, $C_6$-$C_{10}$ aryl, an imidate leading preferably to S-thiazolinyl (STaz) or S-benzoxazolyl (SBox).

18. An oligosaccharide which is selected from the group consisting of:
Benzyl (4-O-benzyl-3-O-para-methoxybenzyl-α-l-rhamnopyranosyl)-(1→2)-(3,4-di-O-benzyl-α-l-rhamnopyranosyl)-(1→4)-(allyl 2,3-di-O-benzyl-β-d-galactopyranosid)uronate,
Allyl (4-O-benzyl-3-O-para-methoxybenzyl-α-l-rhamnopyranosyl)-(1→2)-(3,4-di-O-benzyl-α-l-rhamnopyranosyl)-(1→4)-(benzyl 2,3-di-O-benzyl-β-d-galactopyranosyluronate)-(1→3)-4,6-di-O-benzyl-2-deoxy-2-trichloroacetamido-β-d-galactopyranoside,
3,4,6-Tri-O-benzyl-2-deoxy-2-trichloroacetamido-α/β-d-galactopyranosyl N-phenyltrifluoroacetimidate,
Allyl (2,3-di-O-benzyl-β-d-galactopyranosyl)-(1→3)-4,6-di-O-benzyl-2-deoxy-2-trichloroacetamido-β-d-galactopyranoside,
Allyl (benzyl 2,3-di-O-benzyl-β-d-galactopyranosyluronate)-(1→3)-4,6-di-O-benzyl-2-deoxy-2-trichloroacetamido-β-d-galactopyranoside,
Allyl (benzyl 2,3-di-O-benzyl-4-O-levulinoyl-β-d-galactopyranosyluronate)-(1→3)-4,6-di-O-benzyl-2-deoxy-2-trichloroacetamido-β-d-galactopyranoside,
(Benzyl 2,3-di-O-benzyl-4-O-levulinoyl-β-d-galactopyranosyluronate)-(1→3)-4,6-di-O-benzyl-2-deoxy-2-trichloroacetamido-α/β-d-galactopyranose,
Benzyl 2,3-di-O-benzyl-4-O-levulinoyl-β-d-galactopyranosyluronate-(1→3)-4,6-di-O-benzyl-2-deoxy-2-trichloroacetamido-α/β-d-galactopyranosyl N-phenyltrifluoroacetimidate,
Benzyl 2,3-di-O-benzyl-4-O-levulinoyl-β-d-galactopyranosyluronate-(1→3)-4,6-di-O-benzyl-2-deoxy-2-trichloroacetamido-α/β-d-galactopyranosyl trichloroacetimidate,
(3,4-Di-O-benzyl-2-O-levulinoyl-α-l-rhamnopyranosyl)-(1→4)-(benzyl 2,3-di-O-benzyl-β-d-galactopyranosyluronate)-(1→3)-4,6-di-O-benzyl-2-deoxy-2-trichloroacetamido-α/β-d-galactopyranosyl N-phenyltrifluoroacetimidate,
(4-O-Benzyl-3-O-para-methoxybenzyl-2-O-levulinoyl-α-l-rhamnopyranosyl)-(1→2)-(3,4-di-O-benzyl-α-l-rhamnopyranosyl)-(1→4)-(benzyl 2,3-di-O-benzyl-β-d-galactopyranosyluronate)-(1→3)-4,6-di-O-benzyl-2-deoxy-2-trichloroacetamido-αβ-d-galactopyranosyl N-phenyltrifluoroacetimidate.

\* \* \* \* \*

UNITED STATES PATENT AND TRADEMARK OFFICE
CERTIFICATE OF CORRECTION

| | | |
|---|---|---|
| PATENT NO. | : 10,376,593 B2 | Page 1 of 1 |
| APPLICATION NO. | : 14/438750 | |
| DATED | : August 13, 2019 | |
| INVENTOR(S) | : Laurence Mulard et al. | |

It is certified that error appears in the above-identified patent and that said Letters Patent is hereby corrected as shown below:

On the Title Page

Item (73), add the Assignees:
--INSTITUT PASTEUR, Paris (FR); CENTRE NATIONAL DE LA RECHERCHE SCIENTIFIQUE, Paris (FR); INSTITUT NATIONAL DE LA SANTE ET DE LA RECHERCHE MEDICALE (INSERM), Paris (FR); UNIVERSITE PARIS DESCARTES, Paris (FR)--

Signed and Sealed this
Twenty-first Day of January, 2020

Andrei Iancu
*Director of the United States Patent and Trademark Office*